United States Patent
Hughey et al.

(10) Patent No.: US 10,335,405 B1
(45) Date of Patent: *Jul. 2, 2019

(54) NON-BURST RELEASING PHARMACEUTICAL COMPOSITION

(71) Applicant: PATHEON SOFTGELS INC, High Point, NC (US)

(72) Inventors: Justin R. Hughey, Asheboro, NC (US); Chue Hue Yang, Greensboro, NC (US)

(73) Assignee: Patheon Softgels, Inc., High Point, NC (US)

( * ) Notice: Subject to any disclaimer, the term of this patent is extended or adjusted under 35 U.S.C. 154(b) by 2 days.

This patent is subject to a terminal disclaimer.

(21) Appl. No.: 15/585,212

(22) Filed: May 3, 2017

Related U.S. Application Data

(60) Provisional application No. 62/331,595, filed on May 4, 2016.

(51) Int. Cl.
  *A61K 9/48* (2006.01)
  *A61K 31/485* (2006.01)

(52) U.S. Cl.
  CPC .......... *A61K 31/485* (2013.01); *A61K 9/4808* (2013.01); *A61K 9/4858* (2013.01); *A61K 9/4866* (2013.01)

(58) Field of Classification Search
  CPC .. A61K 31/485; A61K 9/4808; A61K 9/4858; A61K 9/4866
  See application file for complete search history.

(56) References Cited

U.S. PATENT DOCUMENTS

| | | | |
|---|---|---|---|
| 4,828,836 A | 5/1989 | Miller | |
| 4,861,598 A | 8/1989 | Oshlack | |
| 4,970,075 A | 11/1990 | Oshlack | |
| 5,266,331 A | 11/1993 | Oshlack | |
| 5,273,760 A | 12/1993 | Oshlack | |
| 5,286,493 A | 2/1994 | Oshlack | |
| 5,472,943 A | 12/1995 | Crain | |
| 5,478,577 A | 12/1995 | Kaiko | |
| 5,529,787 A | 6/1996 | Ayer | |
| 5,549,912 A | 8/1996 | Kaiko | |
| 5,656,295 A | 8/1997 | Oshlack | |
| 5,672,360 A | 9/1997 | Kaiko | |
| 5,702,725 A | 12/1997 | Chadha | |
| 5,914,131 A | 6/1999 | Ayer | |
| 5,958,452 A | 9/1999 | Oshlack | |
| 5,965,161 A | 10/1999 | Oshlack | |
| 6,228,398 B1 | 5/2001 | Rekhi | |
| 6,228,863 B1 | 5/2001 | Kaiko | |
| 6,261,599 B1 | 7/2001 | Huang | |
| 6,277,384 B1 | 8/2001 | Kaiko | |
| 6,335,033 B2 | 1/2002 | Oshlack | |
| 6,375,957 B1 | 4/2002 | Kaiko | |
| 6,475,494 B2 | 11/2002 | Kaiko | |
| 6,488,963 B1 | 12/2002 | McGinity | |
| 6,627,635 B2 | 9/2003 | Kaiko | |
| 6,685,964 B1 | 2/2004 | Bartholomaeus | |
| 6,696,066 B2 | 2/2004 | Kaiko | |
| 6,696,088 B2 | 2/2004 | Oshlack | |
| 6,706,281 B2 | 3/2004 | Oshlack | |
| 6,713,488 B2 | 3/2004 | Wang | |
| 6,733,783 B2 | 5/2004 | Oshlack | |
| 6,734,188 B1 | 5/2004 | Rhodes | |
| 6,743,442 B2 | 6/2004 | Huang | |
| 6,893,661 B1 | 5/2005 | Odidi | |
| 6,902,742 B2 | 6/2005 | Rekhi | |
| 7,129,248 B2 | 10/2006 | Hong | |
| 7,141,250 B2 | 11/2006 | Wright | |
| 7,144,587 B2 | 12/2006 | Wright | |
| 7,157,103 B2 | 1/2007 | Sackler | |
| 7,172,767 B2 | 2/2007 | Kaiko | |
| 7,201,920 B2 | 4/2007 | Wadgaonkar | |
| 7,276,250 B2 | 10/2007 | McCall | |
| 7,332,182 B2 | 2/2008 | Sackler | |
| 7,384,653 B2 | 6/2008 | Carpanzano | |
| 7,399,488 B2 | 7/2008 | Kibanov | |
| 7,419,686 B2 | 9/2008 | Kaiko | |
| 7,476,402 B2 | 1/2009 | Wadgaonkar | |
| 7,510,726 B2 | 3/2009 | Wadgaonkar | |
| 7,510,727 B2 | 3/2009 | Oshlack | |
| 7,514,100 B2 | 4/2009 | Oshlack | |
| 7,674,798 B2 | 3/2010 | Hong | |
| 7,674,799 B2 | 3/2010 | Hong | |
| 7,674,800 B2 | 3/2010 | Hong | |
| 7,682,633 B2 | 3/2010 | Boehm | |
| 7,682,634 B2 | 3/2010 | Boehm | |
| 7,683,072 B2 | 3/2010 | Hong | |
| 7,691,877 B2 | 4/2010 | Tran | |
| 7,696,208 B2 | 4/2010 | Kyle | |
| 7,727,557 B2 | 6/2010 | Sackler | |

(Continued)

OTHER PUBLICATIONS

Ananthapadmanabhan and Goddard, "Aqueous biphase formation in polyethylene oxide-inorganic salt systems," Langmuir 3(1):25-31 (1987).

*Primary Examiner* — Snigdha Maewall
(74) *Attorney, Agent, or Firm* — Brinks Gilson & Lione

(57) ABSTRACT

Described herein are controlled release oral pharmaceutical compositions and methods for making the same. These pharmaceutical compositions provide a non-burst release of one or more active pharmaceutical ingredients. In particular, a non-burst controlled release oral pharmaceutical composition comprising a capsule and an abuse deterrent controlled release matrix comprising one or more active pharmaceutical ingredients are described.

13 Claims, 12 Drawing Sheets

(56) References Cited

U.S. PATENT DOCUMENTS

| | | | |
|---|---|---|---|
| 7,740,881 | B1 | 6/2010 | Kaiko |
| 7,749,542 | B2 | 7/2010 | Kaiko |
| 7,771,707 | B2 | 8/2010 | Hirsh |
| 7,776,314 | B2 | 8/2010 | Kugelmann |
| 7,776,861 | B2 | 8/2010 | Sun |
| 7,790,201 | B2 | 9/2010 | Raman |
| 7,790,215 | B2 | 9/2010 | Oshlack |
| 7,815,934 | B2 | 10/2010 | Boehm |
| 7,842,307 | B2 | 11/2010 | Wright |
| 7,842,311 | B2 | 11/2010 | Oshlack |
| 7,846,476 | B2 | 12/2010 | Oshlack |
| 7,858,119 | B1 | 12/2010 | Odidi |
| 7,862,833 | B2 | 1/2011 | Moe |
| 7,906,141 | B2 | 3/2011 | Ziegler |
| 7,914,818 | B2 | 3/2011 | Wright |
| 7,943,173 | B2 | 5/2011 | Wright |
| 7,943,174 | B2 | 5/2011 | Oshlack |
| 7,981,439 | B2 | 7/2011 | Wadgaonkar |
| 8,017,148 | B2 | 9/2011 | Sackler |
| 8,030,310 | B2 | 10/2011 | Kyle |
| 8,075,872 | B2 | 12/2011 | Kugelmann |
| 8,101,630 | B2 | 1/2012 | Wadgaonkar |
| 8,105,631 | B2 | 1/2012 | Kaiko |
| 8,114,383 | B2 | 2/2012 | Kugelmann |
| 8,114,384 | B2 | 2/2012 | Bartholomaus |
| 8,142,811 | B2 | 3/2012 | Oshlack |
| 8,158,156 | B2 | 4/2012 | Boehm |
| 8,178,560 | B2 | 5/2012 | Sun |
| 8,182,836 | B2 | 5/2012 | Mehta |
| 8,192,722 | B2 | 6/2012 | Kugelmann |
| 8,231,898 | B2 | 7/2012 | Oshlack |
| 8,231,901 | B2 | 7/2012 | Wright |
| 8,236,328 | B2 | 8/2012 | Curatolo |
| 8,236,351 | B2 | 8/2012 | Oshlack |
| 8,298,577 | B2 | 10/2012 | Moe |
| 8,298,579 | B2 | 10/2012 | Abreu |
| 8,309,060 | B2 | 11/2012 | Arkenau Maric |
| 8,309,122 | B2 | 11/2012 | Baichwal |
| 8,323,889 | B2 | 12/2012 | Kugelmann |
| 8,329,216 | B2 | 12/2012 | Baichwal |
| 8,337,888 | B2 | 12/2012 | Wright |
| 8,357,399 | B2 | 1/2013 | Oshlack |
| 8,361,499 | B2 | 1/2013 | Oshlack |
| 8,377,480 | B2 | 2/2013 | Raman |
| 8,383,152 | B2 | 2/2013 | Galia |
| 8,409,616 | B2 | 4/2013 | Wadgaonkar |
| 8,420,056 | B2 | 4/2013 | Kugelmann |
| 8,425,933 | B2 | 4/2013 | Mehta |
| 8,445,018 | B2 | 5/2013 | Habib |
| 8,445,023 | B2 | 5/2013 | Dargelas |
| 8,449,909 | B2 | 5/2013 | Kilbanov |
| 8,465,774 | B2 | 6/2013 | Wright |
| 8,518,443 | B2 | 8/2013 | Wright |
| 8,524,275 | B2 | 9/2013 | Oshlack |
| 8,529,948 | B1 | 9/2013 | Wright |
| 8,551,520 | B2 | 10/2013 | Oshlack |
| 8,557,291 | B2 | 10/2013 | Hirsh |
| 8,586,088 | B2 | 11/2013 | Oshlack |
| 8,597,681 | B2 | 12/2013 | Park |
| 8,623,418 | B2 | 1/2014 | Tang |
| 8,637,540 | B2 | 1/2014 | Wadgaonkar |
| 8,637,548 | B2 | 1/2014 | Sun |
| 8,647,667 | B2 | 2/2014 | Oshlack |
| 8,652,497 | B2 | 2/2014 | Sackler |
| 8,652,515 | B2 | 2/2014 | Sackler |
| 8,652,529 | B2 | 2/2014 | Dargelas |
| 8,658,631 | B1 | 2/2014 | Devarakonda |
| 8,673,355 | B2 | 3/2014 | Kaiko |
| 8,685,443 | B2 | 4/2014 | Boehm |
| 8,685,444 | B2 | 4/2014 | Boehm |
| 8,703,186 | B2 | 4/2014 | Mehta |
| 8,703,196 | B2 | 4/2014 | Curatolo |
| 8,715,721 | B2 | 5/2014 | Oshlack |
| 8,741,885 | B1 | 6/2014 | Devarakonda |
| 8,758,813 | B2 | 6/2014 | Rariy |
| 8,758,825 | B2 | 6/2014 | Wright |
| 8,790,694 | B2 | 7/2014 | Shelby |
| 8,808,737 | B2 | 8/2014 | Ahdieh |
| 8,808,740 | B2 | 8/2014 | Huang |
| 8,808,741 | B2 | 8/2014 | McKenna |
| 8,815,287 | B2 | 8/2014 | Wright |
| 8,815,289 | B2 | 8/2014 | McKenna |
| 8,821,929 | B2 | 9/2014 | McKenna |
| 8,822,487 | B2 | 9/2014 | Kaiko |
| 8,822,489 | B2 | 9/2014 | Wadgaonkar |
| 8,822,687 | B2 | 9/2014 | Hong |
| 8,834,925 | B2 | 9/2014 | McKenna |
| 8,840,928 | B2 | 9/2014 | Varanasi |
| 8,846,086 | B2 | 9/2014 | McKenna |
| 8,846,090 | B2 | 9/2014 | Broegmann |
| 8,846,091 | B2 | 9/2014 | Broegmann |
| 8,846,104 | B2 | 9/2014 | Boehm |
| 8,858,963 | B1 | 10/2014 | Devarakonda |
| 8,877,247 | B2 | 11/2014 | Boehm |
| 8,883,204 | B2 | 11/2014 | Masselink |
| 8,894,987 | B2 | 11/2014 | McKenna |
| 8,894,988 | B2 | 11/2014 | McKenna |
| 8,901,113 | B2 | 12/2014 | Hall Yung |
| 8,911,719 | B2 | 12/2014 | McKenna |
| 8,920,836 | B2 | 12/2014 | Whitelock |
| 8,932,630 | B1 | 1/2015 | Kaiko |
| 8,936,808 | B1 | 1/2015 | Kaiko |
| 8,936,812 | B2 | 1/2015 | Oshlack |
| 8,951,555 | B1 | 2/2015 | Oshlack |
| 8,969,369 | B2 | 3/2015 | Kao |
| 8,975,273 | B2 | 3/2015 | Oshlack |
| 8,980,291 | B2 | 3/2015 | Oshlack |
| 8,980,319 | B2 | 3/2015 | Park |
| 8,992,975 | B2 | 3/2015 | Shelby |
| 9,023,401 | B1 | 5/2015 | Oshlack |
| 9,034,377 | B2 | 5/2015 | Wright |
| 9,044,398 | B2 | 6/2015 | Klibanov |
| 9,044,402 | B2 | 6/2015 | Overgard |
| 9,044,435 | B2 | 6/2015 | Wright |
| 9,050,335 | B1 | 6/2015 | Devarakonda |
| 9,056,051 | B2 | 6/2015 | Kao |
| 9,056,052 | B1 | 6/2015 | Oshlack |
| 9,056,107 | B1 | 6/2015 | Oshlack |
| 9,060,940 | B2 | 6/2015 | Oshlack |
| 9,060,976 | B2 | 6/2015 | Wright |
| 9,073,933 | B2 | 7/2015 | Hong |
| 9,084,729 | B2 | 7/2015 | Kao |
| 9,084,816 | B2 | 7/2015 | McKenna |
| 9,095,614 | B2 | 8/2015 | McKenna |
| 9,095,615 | B2 | 8/2015 | McKenna |
| 9,101,661 | B2 | 8/2015 | McKenna |
| 9,101,668 | B2 | 8/2015 | Oshlack |
| 9,132,096 | B1 | 9/2015 | Sidwell |
| 9,149,436 | B2 | 10/2015 | Oshlack |
| 9,149,533 | B2 | 10/2015 | Guido |
| 9,155,717 | B2 | 10/2015 | Sackler |
| 9,161,937 | B2 | 10/2015 | Kao |
| 9,168,252 | B2 | 10/2015 | Kao |
| 9,198,861 | B2 | 12/2015 | Dhanarajan |
| 9,198,863 | B2 | 12/2015 | Oshlack |
| 9,205,055 | B2 | 12/2015 | Oshlack |
| 9,205,056 | B2 | 12/2015 | Oshlack |
| 9,205,082 | B2 | 12/2015 | Kaiko |
| 9,216,176 | B2 | 12/2015 | Habib |
| 9,265,760 | B2 | 2/2016 | Hartman |
| 9,301,918 | B2 | 4/2016 | Raman |
| 9,326,982 | B1 | 5/2016 | Hartman |
| 9,333,201 | B1 | 5/2016 | Hartman |
| 9,339,499 | B2 | 5/2016 | Hartman |
| 9,433,582 | B2 | 9/2016 | Shelby |
| 2001/0033865 | A1 | 10/2001 | Oshlack |
| 2001/0036476 | A1 | 11/2001 | Huang |
| 2001/0038856 | A1 | 11/2001 | Ayer |
| 2002/0004509 | A1 | 1/2002 | Kaiko |
| 2002/0006438 | A1 | 1/2002 | Oshlack |
| 2002/0013301 | A1 | 1/2002 | Kaiko |
| 2002/0058050 | A1 | 5/2002 | Kaiko |
| 2002/0058673 | A1 | 5/2002 | Kaiko |
| 2002/0192277 | A1 | 12/2002 | Oshlack |

(56) References Cited

U.S. PATENT DOCUMENTS

| | | |
|---|---|---|
| 2003/0026839 A1 | 2/2003 | Oshlack |
| 2003/0031712 A1 | 2/2003 | Kaiko |
| 2003/0035837 A1 | 2/2003 | Kaiko |
| 2003/0044458 A1 | 3/2003 | Carpanzano |
| 2003/0044464 A1 | 3/2003 | Ziegler |
| 2003/0065002 A1 | 4/2003 | Kao |
| 2003/0068371 A1 | 4/2003 | Wright |
| 2003/0068392 A1 | 4/2003 | Sackler |
| 2003/0069263 A1 | 4/2003 | Wright |
| 2003/0073714 A1 | 4/2003 | Wright |
| 2003/0104063 A1 | 6/2003 | Curatolo |
| 2003/0124185 A1 | 7/2003 | Wright |
| 2003/0157167 A1 | 8/2003 | Baichwal |
| 2003/0157168 A1 | 8/2003 | Wright |
| 2003/0190358 A1 | 10/2003 | Oshlack |
| 2003/0190362 A1 | 10/2003 | Oshlack |
| 2004/0047907 A1 | 3/2004 | Oshlack |
| 2004/0052731 A1 | 3/2004 | Fleming |
| 2004/0058946 A1 | 3/2004 | Rariy |
| 2004/0081694 A1 | 4/2004 | Oshlack |
| 2004/0086561 A1 | 5/2004 | Kaiko |
| 2004/0170680 A1 | 9/2004 | Oshlack |
| 2004/0185096 A1 | 9/2004 | Oshlack |
| 2004/0202717 A1 | 10/2004 | Mehta |
| 2004/0234600 A1 | 11/2004 | Ayer |
| 2004/0266807 A1 | 12/2004 | Oshlack |
| 2005/0031546 A1 | 2/2005 | Bartholomaus |
| 2005/0063909 A1 | 3/2005 | Carpanzano |
| 2005/0089568 A1 | 4/2005 | Oshlack |
| 2005/0112067 A1* | 5/2005 | Kumar ................. A61K 9/2009 424/10.1 |
| 2005/0112188 A1* | 5/2005 | Eliaz ................... A61K 9/0004 424/450 |
| 2005/0192309 A1 | 9/2005 | Kaiko |
| 2005/0214368 A1 | 9/2005 | Odidi |
| 2005/0222188 A1 | 10/2005 | Hong |
| 2005/0236741 A1 | 10/2005 | Bartholomaeus |
| 2005/0245483 A1 | 11/2005 | Spitzley |
| 2005/0245556 A1 | 11/2005 | Spitzley |
| 2005/0281748 A1 | 12/2005 | Hirsh |
| 2006/0002859 A1 | 1/2006 | Bartholomaus |
| 2006/0128717 A1 | 6/2006 | Sun |
| 2006/0173029 A1 | 8/2006 | Hong |
| 2006/0182801 A1 | 8/2006 | Wright |
| 2006/0193782 A1 | 8/2006 | Arkenau Maric |
| 2006/0193914 A1 | 8/2006 | Ashworth |
| 2006/0258669 A1 | 11/2006 | Kyle |
| 2006/0269604 A1 | 11/2006 | Kaiko |
| 2007/0003616 A1 | 1/2007 | Bartholomaus |
| 2007/0014732 A1 | 1/2007 | Sackler |
| 2007/0048228 A1 | 3/2007 | Kugelmann |
| 2007/0117829 A1 | 5/2007 | Hong |
| 2007/0117830 A1 | 5/2007 | Hong |
| 2007/0117831 A1 | 5/2007 | Hong |
| 2007/0122348 A1 | 5/2007 | Kaiko |
| 2007/0166234 A1 | 7/2007 | Wadgaonkar |
| 2007/0179169 A1 | 8/2007 | Hong |
| 2007/0183979 A1 | 8/2007 | Arkenau Maric |
| 2007/0183980 A1 | 8/2007 | Kugelmann |
| 2007/0197478 A1 | 8/2007 | Tran |
| 2007/0207089 A1 | 9/2007 | Abreu |
| 2007/0237832 A1 | 10/2007 | Kaiko |
| 2007/0237833 A1 | 10/2007 | Kaiko |
| 2007/0259045 A1 | 11/2007 | McKenna |
| 2007/0264327 A1 | 11/2007 | Wadgaonkar |
| 2007/0298103 A1 | 12/2007 | Hayes |
| 2008/0031963 A1 | 2/2008 | Kaiko |
| 2008/0069881 A1 | 3/2008 | Kao |
| 2008/0069891 A1 | 3/2008 | Hamed |
| 2008/0132532 A1 | 6/2008 | Wright |
| 2008/0166405 A1 | 7/2008 | Mehta |
| 2008/0199530 A1 | 8/2008 | Fleming |
| 2008/0247959 A1 | 10/2008 | Arkenau Maric |
| 2008/0260819 A1 | 10/2008 | Hirsh |
| 2008/0292694 A1 | 11/2008 | Kaiko |
| 2008/0292700 A1 | 11/2008 | Nghiem |
| 2008/0311049 A1 | 12/2008 | Kugelmann |
| 2008/0311187 A1 | 12/2008 | Ashworth |
| 2008/0312264 A1 | 12/2008 | Bartholomaus |
| 2008/0317854 A1 | 12/2008 | Bartholomaeus |
| 2009/0004292 A1 | 1/2009 | Wadgaonkar |
| 2009/0005408 A1 | 1/2009 | Bartholomaus |
| 2009/0011024 A1 | 1/2009 | Curatolo |
| 2009/0022790 A1 | 1/2009 | Flath |
| 2009/0081290 A1 | 3/2009 | McKenna |
| 2009/0148517 A1 | 6/2009 | Chasin |
| 2009/0202629 A1 | 8/2009 | Oshlack |
| 2009/0202634 A1 | 8/2009 | Galia |
| 2009/0227615 A1 | 9/2009 | Hong |
| 2009/0238868 A1 | 9/2009 | Mehta |
| 2009/0253730 A1 | 10/2009 | Wadgaonkar |
| 2009/0297617 A1* | 12/2009 | Rariy ................... A61K 9/1617 424/490 |
| 2010/0028389 A1 | 2/2010 | Merrill |
| 2010/0098771 A1 | 4/2010 | Mehta |
| 2010/0151028 A1 | 6/2010 | Kugelmann |
| 2010/0152449 A1 | 6/2010 | Hong |
| 2010/0172974 A1 | 7/2010 | Chasin |
| 2010/0209351 A1 | 8/2010 | Sackler |
| 2010/0209514 A1 | 8/2010 | Sackler |
| 2010/0216829 A2 | 8/2010 | Tewari |
| 2010/0240675 A1 | 9/2010 | Kyle |
| 2010/0260834 A1 | 10/2010 | Hirsh |
| 2010/0273730 A1* | 10/2010 | Hsu ..................... A61K 9/1075 514/49 |
| 2010/0291203 A1 | 11/2010 | Kaiko |
| 2010/0331369 A1 | 12/2010 | Sun |
| 2011/0038927 A1 | 2/2011 | Oshlack |
| 2011/0071192 A1 | 3/2011 | Sun |
| 2011/0077238 A1 | 3/2011 | Hall Yung |
| 2011/0104214 A1 | 5/2011 | Oshlack |
| 2011/0142943 A1 | 6/2011 | Saim |
| 2011/0150989 A1 | 6/2011 | Dhanarajan |
| 2011/0200681 A1 | 8/2011 | Kraling |
| 2011/0207762 A1 | 8/2011 | Hong |
| 2011/0230510 A1 | 9/2011 | Wright |
| 2011/0256226 A1 | 10/2011 | Wright |
| 2011/0262532 A1 | 10/2011 | Oshlack |
| 2011/0287095 A1 | 11/2011 | Park |
| 2011/0300217 A1 | 12/2011 | Ayer |
| 2012/0034171 A1 | 2/2012 | Kugelmann |
| 2012/0087982 A1 | 4/2012 | Wadgaonkar |
| 2012/0088786 A1 | 4/2012 | Hayes |
| 2012/0107250 A1 | 5/2012 | Kugelmann |
| 2012/0108621 A1 | 5/2012 | Broegmann |
| 2012/0141583 A1 | 6/2012 | Hahn |
| 2012/0164220 A1 | 6/2012 | Huang |
| 2012/0165359 A1 | 6/2012 | Kaiko |
| 2012/0183612 A1 | 7/2012 | Broegmann |
| 2012/0201761 A1 | 8/2012 | Sackler |
| 2012/0225122 A1 | 9/2012 | Vega Zepeda |
| 2012/0225901 A1 | 9/2012 | Smith |
| 2012/0251637 A1 | 10/2012 | Kugelmann |
| 2012/0252832 A1 | 10/2012 | Kao |
| 2012/0263788 A1 | 10/2012 | Oshlack |
| 2012/0288567 A1 | 11/2012 | Wright |
| 2012/0295988 A1 | 11/2012 | Curatolo |
| 2013/0004575 A1 | 1/2013 | Jackson |
| 2013/0005977 A1 | 1/2013 | Hong |
| 2013/0017255 A1 | 1/2013 | Osvaldo |
| 2013/0045960 A1 | 2/2013 | Fleming |
| 2013/0090349 A1 | 4/2013 | Geisler |
| 2013/0122087 A1 | 5/2013 | Hillman |
| 2013/0122101 A1 | 5/2013 | Habib |
| 2013/0158061 A1 | 6/2013 | Oshlack |
| 2013/0165418 A1 | 6/2013 | Colucci |
| 2013/0171075 A1 | 7/2013 | Kugelmann |
| 2013/0171257 A1 | 7/2013 | Tewari |
| 2013/0172382 A1 | 7/2013 | Kao |
| 2013/0209560 A1 | 8/2013 | Hamed |
| 2013/0230596 A1 | 9/2013 | Mehta |
| 2013/0251759 A1 | 9/2013 | Bartholomuaes |
| 2013/0251796 A1 | 9/2013 | McKenna |
| 2013/0251797 A1 | 9/2013 | McKenna |

(56) References Cited

U.S. PATENT DOCUMENTS

| | | |
|---|---|---|
| 2013/0251798 A1 | 9/2013 | McKenna |
| 2013/0251799 A1 | 9/2013 | McKenna |
| 2013/0251800 A1 | 9/2013 | McKenna |
| 2013/0251801 A1 | 9/2013 | McKenna |
| 2013/0251802 A1 | 9/2013 | McKenna |
| 2013/0251812 A1 | 9/2013 | Wright |
| 2013/0259938 A1 | 10/2013 | McKenna |
| 2013/0259939 A1 | 10/2013 | McKenna |
| 2013/0259940 A1 | 10/2013 | McKenna |
| 2013/0260015 A1 | 10/2013 | McKenna |
| 2013/0273153 A1 | 10/2013 | Dhanarajan |
| 2013/0280176 A1 | 10/2013 | Diezi |
| 2013/0280177 A1 | 10/2013 | Raman |
| 2013/0289062 A1 | 10/2013 | Wadgaonkar |
| 2013/0295177 A1 | 11/2013 | Oshlack |
| 2013/0302418 A1 | 11/2013 | Oshlack |
| 2013/0309303 A1 | 11/2013 | Wright |
| 2013/0310413 A1 | 11/2013 | Kilbanov |
| 2013/0317051 A1 | 11/2013 | Oshlack |
| 2013/0320592 A1 | 12/2013 | Bartholomaus |
| 2014/0010873 A1 | 1/2014 | Overgard |
| 2014/0010875 A1 | 1/2014 | Huang |
| 2014/0011832 A1 | 1/2014 | Huang |
| 2014/0017310 A1 | 1/2014 | Castaneda |
| 2014/0024669 A1 | 1/2014 | McKenna |
| 2014/0030327 A1 | 1/2014 | McKenna |
| 2014/0031381 A1 | 1/2014 | McKenna |
| 2014/0031382 A1 | 1/2014 | Smith |
| 2014/0045877 A1 | 2/2014 | Broegmann |
| 2014/0045878 A1 | 2/2014 | Broegmann |
| 2014/0079780 A1 | 3/2014 | Kugelmann |
| 2014/0080858 A1 | 3/2014 | Kugelmann |
| 2014/0080915 A1 | 3/2014 | Kugelmann |
| 2014/0086847 A1 | 3/2014 | Kugelmann |
| 2014/0086987 A1 | 3/2014 | Park |
| 2014/0099376 A2 | 4/2014 | Wright |
| 2014/0105830 A1 | 4/2014 | Kugelmann |
| 2014/0105977 A1 | 4/2014 | Shelby |
| 2014/0105987 A1 | 4/2014 | Hirsh |
| 2014/0107146 A1 | 4/2014 | Kao |
| 2014/0112981 A1 | 4/2014 | Oshlack |
| 2014/0112984 A1 | 4/2014 | Kugelmann |
| 2014/0113926 A1 | 4/2014 | Bartholomaeus |
| 2014/0121232 A1 | 5/2014 | Rariy |
| 2014/0135355 A1 | 5/2014 | Kao |
| 2014/0155425 A1 | 6/2014 | Sackler |
| 2014/0155489 A1 | 6/2014 | Kugelmann |
| 2014/0170079 A1 | 6/2014 | Kugelmann |
| 2014/0170217 A1 | 6/2014 | Shelby |
| 2014/0187572 A1 | 7/2014 | Wright |
| 2014/0194456 A1 | 7/2014 | Kao |
| 2014/0199394 A1 | 7/2014 | Oshlack |
| 2014/0200236 A1 | 7/2014 | Kaiko |
| 2014/0213606 A1 | 7/2014 | Wright |
| 2014/0220126 A1 | 8/2014 | Overgard |
| 2014/0221416 A1 | 8/2014 | Guido |
| 2014/0249185 A1 | 9/2014 | Sun |
| 2014/0256764 A1 | 9/2014 | Abreu |
| 2014/0271840 A1 | 9/2014 | Huang |
| 2014/0275143 A1 | 9/2014 | Gupta |
| 2014/0288113 A1 | 9/2014 | Shelby |
| 2014/0294953 A1 | 10/2014 | Vega Zepeda |
| 2014/0294956 A1 | 10/2014 | Shelby |
| 2014/0296276 A1 | 10/2014 | Wright |
| 2014/0296277 A1 | 10/2014 | Broegmann |
| 2014/0322311 A1 | 10/2014 | Kugelmann |
| 2014/0322323 A1 | 10/2014 | Galia |
| 2014/0329847 A1 | 11/2014 | Ahdieh |
| 2014/0336213 A1 | 11/2014 | Wadgaonkar |
| 2014/0356294 A1 | 12/2014 | Kugelmann |
| 2014/0357658 A1 | 12/2014 | Kaiko |
| 2014/0377348 A1 | 12/2014 | Oshlack |
| 2014/0378498 A1 | 12/2014 | Devarakonda |
| 2015/0004244 A1 | 1/2015 | Varanasi |
| 2015/0005332 A1 | 1/2015 | Varanasi |
| 2015/0005335 A1 | 1/2015 | Broegmann |
| 2015/0005336 A1 | 1/2015 | Kaiko |
| 2015/0025101 A1 | 1/2015 | Kaiko |
| 2015/0028512 A1 | 1/2015 | McKenna |
| 2015/0031718 A1 | 1/2015 | Wright |
| 2015/0037409 A1 | 2/2015 | Oshlack |
| 2015/0037411 A1 | 2/2015 | McKenna |
| 2015/0037412 A1 | 2/2015 | McKenna |
| 2015/0037413 A1 | 2/2015 | McKenna |
| 2015/0056147 A1 | 2/2015 | Kugelmann |
| 2015/0080384 A1 | 3/2015 | Hall Yung |
| 2015/0110870 A1 | 4/2015 | Oshlack |
| 2015/0110879 A1 | 4/2015 | Wright |
| 2015/0118302 A1 | 4/2015 | Haswani |
| 2015/0118303 A1 | 4/2015 | Haswani |
| 2015/0140086 A1 | 5/2015 | Masselink |
| 2015/0140095 A1 | 5/2015 | Oshlack |
| 2015/0148366 A1 | 5/2015 | Whitelock |
| 2015/0148367 A1 | 5/2015 | Oshlack |
| 2015/0150978 A1 | 6/2015 | Kugelmann |
| 2015/0164808 A1 | 6/2015 | Shelby |
| 2015/0164811 A1 | 6/2015 | Bartholomaeus |
| 2015/0174121 A1 | 6/2015 | Oshlack |
| 2015/0182464 A1 | 7/2015 | Kugelmann |
| 2015/0182465 A1 | 7/2015 | Kugelmann |
| 2015/0182467 A1 | 7/2015 | Oshlack |
| 2015/0196555 A1 | 7/2015 | Guido |
| 2015/0196556 A1 | 7/2015 | Guido |
| 2015/0196557 A1 | 7/2015 | Guido |
| 2015/0202300 A1 | 7/2015 | Guido |
| 2015/0216809 A1 | 8/2015 | Oshlack |
| 2015/0216810 A1 | 8/2015 | Oshlack |
| 2015/0231086 A1 | 8/2015 | Oshlack |
| 2015/0231131 A1 | 8/2015 | Oshlack |
| 2015/0238418 A1 | 8/2015 | Oshlack |
| 2015/0238481 A1 | 8/2015 | Wright |
| 2015/0246034 A1 | 9/2015 | Devarakonda |
| 2015/0250781 A1 | 9/2015 | Habib |
| 2015/0258086 A1 | 9/2015 | Hong |
| 2015/0258087 A1 | 9/2015 | Kao |
| 2015/0258088 A1 | 9/2015 | Kao |
| 2015/0258089 A1 | 9/2015 | Oshlack |
| 2015/0258090 A1 | 9/2015 | Oshlack |
| 2015/0265537 A1 | 9/2015 | Oshlack |
| 2015/0265596 A1 | 9/2015 | Hirsh |
| 2015/0265597 A1 | 9/2015 | Hong |
| 2015/0265598 A1 | 9/2015 | Hong |
| 2015/0265599 A1 | 9/2015 | McKenna |
| 2015/0265600 A1 | 9/2015 | McKenna |
| 2015/0265601 A1 | 9/2015 | McKenna |
| 2015/0265603 A1 | 9/2015 | Wright |
| 2015/0265605 A1 | 9/2015 | Wright |
| 2015/0265607 A1 | 9/2015 | Wright |
| 2015/0290138 A1 | 10/2015 | Kugelmann |
| 2015/0297527 A1 | 10/2015 | Qi |
| 2015/0335580 A1 | 11/2015 | McKenna |
| 2015/0335582 A1 | 11/2015 | McKenna |
| 2015/0335583 A1 | 11/2015 | McKenna |
| 2015/0335584 A1 | 11/2015 | McKenna |
| 2015/0335585 A1 | 11/2015 | McKenna |
| 2015/0374628 A1 | 12/2015 | Wright |
| 2015/0374631 A1 | 12/2015 | Wright |
| 2016/0000703 A1 | 1/2016 | Micka |
| 2016/0000717 A1 | 1/2016 | Wright |
| 2016/0000718 A1 | 1/2016 | Wright |
| 2016/0000719 A1 | 1/2016 | Wright |
| 2016/0000776 A1 | 1/2016 | Wright |
| 2016/0008350 A1 | 1/2016 | Oshlack |
| 2016/0045449 A1 | 2/2016 | Lamson |
| 2016/0120810 A1 | 5/2016 | Kugelmann |
| 2016/0136152 A1 | 5/2016 | Baichwal |
| 2016/0151289 A1 | 6/2016 | Wright |
| 2016/0151290 A1 | 6/2016 | Wright |
| 2016/0151291 A1 | 6/2016 | Wright |
| 2016/0151297 A1 | 6/2016 | Wright |
| 2016/0151356 A1 | 6/2016 | Wright |
| 2016/0184299 A1 | 6/2016 | Shelby |

(56) References Cited

U.S. PATENT DOCUMENTS

| | | |
|---|---|---|
| 2016/0243041 A1 | 8/2016 | Shelby |
| 2016/0250203 A1 | 9/2016 | Haswani |
| 2016/0256392 A1 | 9/2016 | Haswani |

\* cited by examiner

NON-BURST RELEASING PHARMACEUTICAL COMPOSITION

CROSS REFERENCE TO RELATED APPLICATIONS

This application claims to priority to U.S. Provisional Patent Application No. 62/331,595, filed on May 4, 2016, which is incorporated herein in its entirety by express reference thereto.

TECHNICAL FIELD

Described herein are controlled release oral pharmaceutical compositions and methods for making the same. These pharmaceutical compositions provide a non-burst release of one or more active pharmaceutical ingredients. In particular, abuse deterrent non-burst controlled release oral pharmaceutical compositions comprising one or more active pharmaceutical ingredients are described.

BACKGROUND

Increased attention has been drawn to the recreational use and abuse of prescription pharmaceutical compositions. The abuse, or non-medicinal use, of prescription pharmaceutical compositions is an increasing problem. Accordingly, preventing the abuse of prescription pharmaceuticals through the development of abuse deterrent pharmaceutical compositions has become a high public health priority for the U.S. Food and Drug Administration (FDA). Prescription pharmaceutical compositions that are typically misused or abused fall, primarily, into three groups: (1) opioids prescribed for pain; (2) Central Nervous System (CNS) depressants prescribed for anxiety or sleep problems; and (3) stimulants, prescribed, for example, for attention deficit hyperactivity, narcolepsy, or obesity.

Methods for abusing prescription pharmaceutical compositions are varied and can include, for example, extraction, boiling, melting, volatilization, physical tampering (e.g., grinding, grating, crushing, etc.), or direct administration. For purposes of abuse, methods of administering active drug substances obtained from prescription pharmaceutical compositions or of the pharmaceutical compositions themselves are similarly diverse and include, for example, injection, smoking, snorting, swallowing, sublingual or buccal administration, chewing, or administration as an anal or vaginal suppository. Alcohol-induced "dose dumping," i.e., the rapid release of active pharmaceutical ingredients in the presence of a solvent such as ethanol, is also an abuse concern and safety issue. Other methods include rapid extraction under aqueous boiling conditions.

Many pharmaceutical formulations have an immediate "burst release" or "bolus release" of the API as the surface of the dosage from begins to rapidly dissolve. The high burst release of abuse-prone active ingredients contributes to the addictive "pleasant high" or "euphoric" effect and can also result in potentially dangerous blood plasma levels of the API (e.g., $C_{max}$) that can potentially be toxic. The burst release of active ingredients is particularly evident for monolithic controlled release drug platforms. The toxicities associated with abuse-prone drugs can be drastically increased when multiple dosages are taken simultaneously and can result in overdosing or death.

There are a number of strategies for preventing the abuse of pharmaceuticals. Physical and chemical barriers can prevent or hinder extraction of the drug or change the form of the drug making it less likely to be abused. Combinations of agonists and antagonists can be used, wherein the antagonist is only released upon product manipulation or tampering. Another strategy is to use aversive compounds that produce an unpleasant effect when the dosage form is tampered and compromized. In addition, prodrugs can be used, which are only changed into the active form of the drug in the gastrointestinal tract. The pharmaceutical industry is utilizing these strategies to develop abuse-deterrent pharmaceutical compositions in order to reduce the potential for misuse of prescription pharmaceutical compositions.

There remains a need for new abuse deterrent pharmaceutical compositions that have enhanced controlled release properties and prevent the burst release of the active pharmaceutical ingredient.

SUMMARY

Described herein are pharmaceutical compositions comprising abuse deterrent controlled release matrices comprising active pharmaceutical ingredients. The matrix is structured to both prevent a burst release of one or more active ingredients and also to prevent the physical extraction of the active pharmaceutical ingredients. The compositions described herein minimize the likelihood of tampering, "dose dumping," or the extraction of active pharmaceutical ingredients from the composition. In particular, the composition prevents the extraction of one or more active ingredients under boiling conditions.

One embodiment described herein is an abuse deterrent oral pharmaceutical composition comprising a tamper resistant controlled release matrix, wherein the tamper resistant controlled release matrix comprises a means for preventing the crushing, grating, grinding, cutting, solvating, or dissolving of the tamper resistant controlled release matrix comprising one or more active pharmaceutical ingredients. The compositions described herein reduce a burst release of the one or more active pharmaceutical ingredients. In particular, the compositions described herein further reduce the burst release of one or more active pharmaceutical ingredients under boiling conditions.

Another embodiment described herein is an abuse deterrent oral pharmaceutical composition comprising a tamper resistant controlled release matrix comprising: (a) one or more flowability enhancers; (b) one or more release modifiers; (c) one or more surfactants; and (d) one or more active pharmaceutical ingredients; wherein the matrix is resistant to tampering and prevents the burst release of the one or more active pharmaceutical ingredients and is encapsulated in a capsule shell. In one aspect described herein, the tamper resistant controlled release matrix further comprises one or more antioxidants. In another aspect described herein, the tamper resistant controlled release matrix further comprises one or more viscosity modifiers. In another aspect described herein, the flowability enhancer comprises about 35% to about 70% of the total matrix mass. In another aspect described herein, the release modifier comprises from about 20% to about 50% of the total matrix mass. In another aspect described herein, the active pharmaceutical ingredient comprises about 0.1% to about 35% of the total matrix mass. In another aspect described herein, the at least one antioxidant comprises about 0.05% to about 0.5% of the total matrix mass. In another aspect described herein, the viscosity modifier comprises about 0.5% to about 8% of the total matrix mass. In another aspect, the surfactant comprises about 0.5% to about 8% of the total matrix mass. In another aspect described herein, the ratio of the active pharmaceutical ingredient percent mass to the matrix percent mass is about 1:1000 to about 1:3.

In another aspect described herein, the surfactant comprises a non-ionic surfactant, an anionic surfactant, a zwitterionic surfactant, or a cationic surfactant or a combination thereof.

In another aspect described herein, the flowability enhancer comprises non-ionic surfactant like properties. In another aspect described herein, the flowability enhancer comprises a hydrophilic lipophilic balance of less than about 5. In another aspect described herein, the flowability enhancer comprises a medium chain mono, di, or triglyceride; or a liquid lipophilic vehicle. In another aspect described herein, the flowability enhancer comprises glyceryl monocaprylate, glyceryl monocaprylcaprate, glyceryl monolinoleate, oleic acid, or a combination thereof. In another aspect described herein, the release modifier comprises a high molecular weight polyethylene oxide, or a combination thereof.

In another aspect, the surfactant comprises a $C_6$-$C_{25}$ alkyl surfactant comprising an alkyl carboxylate, alkyl sulfate, alkyl sulfonate, an alkyl ether sulfate, or a quaternary ammonium containing surfactant or a combination thereof. In another aspect, the surfactant comprises sodium octyl sulfate, sodium lauryl sulfate (sodium dodecyl sulfate), sodium laureth sulfate, disodium laureth sulfosuccinate, sodium docusate, benzalkonium chloride, cetrimonium bromide, dimethyldioctadecylammonium chloride, or lauryl methyl gluceth-10 hydroxypropyl dimonium chloride or a combination thereof.

In another aspect described herein, the release modifier comprises a polyethylene oxide having, a carboxyvinyl polymer or a mixture thereof. In another aspect, the molecular weight of the polyethylene oxide is about 3,000,000, about 4,000,000, about 5,000,000; about 6,000,000, about 7,000,000, about 8,000,000, about 9,000,000, or about 10,000,000. In another aspect described herein, the viscosity modifier comprises polyvinyl pyrrolidone or ethylcellulose, or a combination thereof.

In another aspect described herein, the antioxidant comprises alpha tocopherol, beta tocopherol, gamma tocopherol, delta tocopherol, butylated hydroxytoluene (BHT), butylated hydroxyanisole (BHA), citric acid, ascorbic acid, carnosic acid, carnosol, rosmanol, epirosmanol, isorosmanol, methyl carnosate, rosmarinic acid, eugenol, eugenyl acetate, clove bud extract, methanolic extract, epigallocatechin gallate, epicatechin gallate, epigallocatechin, epicatechin, or a combination thereof.

In another aspect described herein, the tamper resistant controlled release matrix forms a semisolid elastic composition after being heated at a temperature of about 50° C. to about 90° C. for a period of time of about 0.1 hours to about 3 hours.

In another aspect described herein, the active pharmaceutical ingredient comprises one or more of: hydrocodone, morphine, morphine analogues, or morphine antagonists, tapentadol, codeine, morphine, methadone, fentanyl and analogs: hydrocodone hydrochloride, hydrocodone bitartrate, hydromorphone, oxymorphone, oxycodone, meperidine, propoxyphene, flunitrazepam, barbiturates, amytal, nembutal, seconal, phenobarbital; benzodiazepines, zolpidem, zaleplon, eszopiclone, amphetamines, methylphenidate, or a combination thereof. In another aspect described herein, the active pharmaceutical ingredient comprises hydrocodone, oxycodone, or a pharmaceutically acceptable salt thereof.

In another aspect described herein, the active pharmaceutical ingredient comprises hydrocodone or oxycodone and a second active pharmaceutical ingredient that reduces the symptoms of, or onset of, or prophylaxis, of a bowel dysfunction due to acute or chronic opioid use. In another aspect described herein, the second active pharmaceutical ingredient comprises a peripherally acting mu opioid receptor antagonist comprising methylnaltrexone, naltrexone, naloxone, naloxegol, alvimopan or a combination thereof. In another aspect described herein, the peripherally acting mu-opioid receptor antagonist comprises methylnaltrexone, naltrexone, naloxone or a combination thereof. In another aspect described herein, the peripherally acting mu-opioid receptor antagonist comprises naloxone. In another aspect described herein, the active pharmaceutical ingredient comprises hydrocodone and naloxone or oxycodone and naloxone. In another aspect described herein, the at least one active pharmaceutical ingredient comprises hydrocodone and naltrexone or oxycodone and naltrexone.

In another embodiment described herein, the tamper resistant controlled release matrix comprises: (a) oleic acid or glyceryl monolinoleate; (b) polyethylene oxide; (c) ethylcellulose; (d) sodium lauryl sulfate; and (e) hydrocodone or oxycodone; and optionally one or both of: (f) BHT; and (g) BHA. In another aspect described herein, the tamper resistant controlled release matrix comprises: (a) about 50% to about 65% of oleic acid or glyceryl monolinoleate; (b) about 25% to about 35% polyethylene oxide having a molecular weight of from about 3,000,000 to about 7,000,000; (c) about 1% to about 5% ethylcellulose 20 cP; and (d) about 1% to about 5% of sodium lauryl sulfate; and (e) about 1.5% to about 10% of oxycodone or hydrocodone; and optionally, one or both of: (f) about 0.25% BHT; and (g) about 0.1% BHA. In another aspect described herein, the tamper resistant controlled release matrix further comprises a peripherally acting mu-opioid receptor antagonist comprising naloxone, methyl naltrexone, or naltrexone. In another aspect described herein, the weight percentage ratio of naloxone methyl naltrexone or naltrexone to hydrocodone or oxycodone is about 15:1 to about 1:18. In another aspect described herein, the weight percentage ratio of naloxone to hydrocodone or oxycodone is about 1:2.

In another embodiment described herein, the capsule shell comprises a soft capsule shell. In another embodiment described herein, the capsule shell comprises a hard capsule shell.

In another embodiment described herein the soft capsule shell comprises one or more film forming polymers, one or more plasticizers, one or more solvents, and optionally, an opacifying agent, a coloring agent, or a pharmaceutical excipient or combinations thereof.

In one aspect described herein, the soft capsule shell comprises: (a) about 25% to about 50% of one or more film-forming polymers; (b) about 15% to about 25% of one or more plasticizers; (c) about 20% to about 40% of one or more solvents; (d) optionally, an opacifying agent, a coloring agent, a pharmaceutical excipient, or a combination thereof. In another aspect described herein, the soft capsule shell comprises: (a) about 42% of or more film-forming polymers; (b) about 20% of one or more plasticizers; (c) about 38% of one or more solvents; (d) optionally, about 0.7% of an opacifying agent; and (e) optionally, about 0.1% at least one coloring agent. In another aspect described herein, the soft capsule shell comprises gelatin, glycerol, water, and optionally, titanium oxide, and a coloring agent.

Another embodiment described herein is a method of making the tamper resistant controlled release matrix dosage form as described herein comprising the steps of (a) suspending one or more release modifiers in one or more flowability enhancers to form a first mixture and (b) adding one or more active pharmaceutical ingredients to the first mixture to form a matrix mixture that may be encapsulated in a soft capsule shell or a hard capsule shell. In one aspect, step (a) further comprises dissolving one or more viscosity modifiers in the one or more flowability enhancers.

Another embodiment described herein is a method for manufacturing a soft capsule shell and a tamper resistant controlled release matrix comprising: (a) providing a matrix comprising the composition as described herein made by the methods of manufacturing described herein; (b) providing a soft capsule gel mass described herein; (c) casting the soft capsule gel mass into films using heat-controlled drums or surfaces; (d) forming a soft capsule comprising the matrix composition using rotary die encapsulation technology; and (e) heating the formed capsules for about 0.1 hours to about 1 hour at about 50° C. to about 90° C. to form an annealed soft capsule dosage form wherein following heating, the matrix has tamper resistant controlled release properties.

Another embodiment described herein is a soft or hard capsule comprising a tamper resistant controlled release matrix produced by the methods described herein.

Another embodiment described herein is a tamper resistant oral pharmaceutical composition comprising a tamper resistant controlled release matrix comprising: (a) about 50% to about 65% of oleic acid; (b) about 25% to about 35% polyethylene oxide having a molecular weight of from about 3,000,000 to about 7,000,000; (c) about 1% to about 5% ethylcellulose 20 cP; (d) about 1% to about 5% of sodium lauryl sulfate; (e) about 1.5% to about 10% of oxycodone or hydrocodone; (f) about 0.25% BHT; and (g) about 0.1% BHA; wherein the matrix is resistant to tampering and has controlled release properties; the matrix being encapsulated in a soft capsule shell comprising: (h) about 25% to about 50% gelatin; (i) about 15% to about 25% glycerol; (j) about 20% to about 40% water; and (k) optionally, an opacifying agent, a coloring agent, a pharmaceutical excipient, or a combination thereof.

Another embodiment described herein is a tamper resistant oral pharmaceutical composition comprising a tamper resistant controlled release matrix comprising: (a) about 50% to about 65% of glyceryl monolinoleate; (b) about 25% to about 35% polyethylene oxide having a molecular weight of from about 3,000,000 to about 7,000,000; (c) about 1% to about 5% of sodium lauryl sulfate; (d) about 1.5% to about 10% of oxycodone or hydrocodone; (e) about 0.25% BHT; and (f) about 0.1% BHA; wherein the matrix is resistant to tampering and has controlled release properties; the matrix being encapsulated in a soft capsule shell comprising: (g) about 25% to about 50% gelatin; (h) about 15% to about 25% glycerol; (i) about 20% to about 40% water; and (j) optionally, an opacifying agent, a coloring agent, a pharmaceutical excipient, or a combination thereof.

In one aspect described herein, the tamper resistant controlled release matrix further comprises a peripherally acting mu-opioid receptor antagonist comprising naloxone, methyl naltrexone, or naltrexone. In another aspect described herein, the weight percentage ratio of naloxone, methyl naltrexone or naltrexone to hydrocodone or oxycodone is about 15:1 to about 1:18. In another aspect described herein, the weight percentage ratio of naloxone to hydrocodone or oxycodone is about 1:2.

Another embodiment described herein is a method for treating, reducing the symptoms or onset of, or prophylaxis of pain stemming from diabetic neuropathy, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica or granuloma annulare comprising administering to a subject in need thereof the pharmaceutical composition as described herein. In one aspect described herein, the administration is sufficient to achieve a reduction of pain relative to baseline in the subject without substantially inducing one or more of opioid induced bowel disfunction (OIBD) comprising constipation (opioid induced constipation; OIC), anorexia, nausea and vomiting, gastrooesophageal reflux, delayed digestion, abdominal pain, flatulence, bloating, hard stools, incomplete evacuation or straining during bowel movements.

Another embodiment described herein is a method for delivering about a 10 mg to about a 80 mg dose of oxycodone or about 10 mg to about 80 mg of hydrocodone comprising administering to a subject a pharmaceutical composition comprising oxycodone or hydrocodone and other pharmaceutically acceptable excipients in a tamper resistant matrix in a soft gel capsule, the method capable of achieving one or more of the following pharmacokinetic parameters: (a) a mean plasma oxycodone $T_{max}$ of about 1 hours to about 8 hours; (b) a mean plasma oxycodone $C_{max}$ of about 10 ng/mL to about 150 ng/mL; (c) a mean plasma oxycodone $AUC_{0 \to \infty}$ of about 100 h·mg/L to about 1000 h·mg/L; (d) a mean plasma hydrocodone $T_{max}$ of about 3 hours to about 8 hours; (e) a mean plasma hydrocodone $C_{max}$ of about 10 ng/mL to about 120 ng/mL; (f) a mean plasma hydrocodone $AUC_{0 \to \infty}$ of about 100 h·mg/L to about 1600 h·mg/L.

In one aspect described herein, the method further comprises delivering a dose of a peripherally acting mu opioid receptor antagonist comprising naloxone, methyl naltrexone, or naltrexone. In another aspect described herein, the weight percentage ratio of naloxone methyl naltrexone or naltrexone to hydrocodone or oxycodone is about 15:1 to about 1:18. In another aspect described herein, the weight percentage ratio of naloxone to hydrocodone or oxycodone is about 1:2.

In another aspect described herein, the administration of the compositions described herein is sufficient to achieve a reduction of pain relative to baseline in the subject without substantially inducing one or more of opioid induced bowel disfunction (OIBD) comprising constipation (opioid induced constipation), anorexia, nausea and vomiting, gastrooesophageal reflux, delayed digestion, abdominal pain, flatulence, bloating, hard stools, incomplete evacuation, or straining during bowel movements.

In another aspect described herein, the administration of the compositions described herein provides an improvement of bowel function during pain therapy, comprising an improvement of the mean bowel function score of at least about 5, at least about 8, at least about 10, or at least about 15 after steady state administration to human patients, wherein the mean bowel function score is measured with a numerical analog scale ranging from 0 to 100. In another aspect described herein, the administration of the compositions described herein provides an improvement of bowel function during pain therapy comprising an improvement in a number of spontaneous bowel movements per week over a time course of about 1 week to about 4 weeks. In another aspect, the improvement in the number of spontaneous bowel movements per week comprises between 1 and 5 additional spontaneous bowel movements per week. In another aspect described herein, the pharmaceutical composition comprises the tamper resistant controlled release matrix as described herein.

In another aspect described herein, the pharmaceutical composition exhibits an in vitro dissolution rate at pH 1.2, of about 35% to about 95% after about 60 minutes to about 480 minutes. In another aspect described herein, the pharmaceutical composition exhibits an in vitro dissolution rate at pH 1.2, of less than about 20% after about 60 minutes to about 480 minutes. In another aspect described herein, the pharmaceutical composition exhibits an in vitro dissolution rate under boiling conditions of less than about 35% to about 60% after about 10 minutes to about 45 minutes. In another aspect described herein, the pharmaceutical composition exhibits an in vitro dissolution rate in an aqueous alcohol solution or distilled water of less than about 20% to about 50% after about 30 minutes to about 360 minutes.

Another embodiment described herein is method for reducing the ability of a subject to extract an active pharmaceutical ingredient from a pharmaceutical dosage form though crushing, grating, grinding, cutting, or solvating or dissolving the matrix comprising: providing the abuse deterrent composition as described herein, wherein the composition is resistant to crushing, grating, grinding, cutting, solvation, or dissolution. In one aspect described herein, the pharmaceutical composition comprises a soft capsule shell or hard capsule shell as described herein.

Another embodiment described herein is a method for reducing the burst release of one or more active ingredients from a pharmaceutical composition comprising providing the pharmaceutical composition described herein.

Another embodiment described herein is a method for reducing the burst release of one or more active ingredients comprising adding one or more surfactants described herein to an abuse deterrent matrix, wherein the abuse deterrent matrix comprises: (a) one or more flowability enhancers; (b) one or more release modifiers; and (c) one or more active pharmaceutical ingredients. Another embodiment described herein is an abuse deterrent oral pharmaceutical composition comprising a tamper resistant controlled release matrix, wherein the tamper resistant controlled release matrix comprises a means for preventing the crushing, grating, grinding, cutting, solvating, or dissolving of the tamper resistant controlled release matrix comprising one or more active pharmaceutical ingredients. In another aspect, the matrix comprises a means for preventing the burst release of one or more active pharmaceutical ingredients.

Another embodiment described herein is a kit for dispensing an abuse deterrent oral pharmaceutical composition described herein comprising: (a) one or more tamper resistant controlled release dosage forms comprising a composition described herein (b) at least one receptacle comprising a tamper evident, moisture proof packaging that reduces the ability of removing the oral pharmaceutical composition comprising blister or strip packs, aluminum blister, transparent or opaque polymer blister with pouch, polypropylene tubes, colored blister materials, tubes, bottles, and bottles optionally containing a child resistant feature, optionally comprising a desiccant, such as a molecular sieve or silica gel; and (c) optionally, an insert comprising instructions or prescribing information for the active pharmaceutical ingredient.

DETAILED DESCRIPTION

Figure 1:
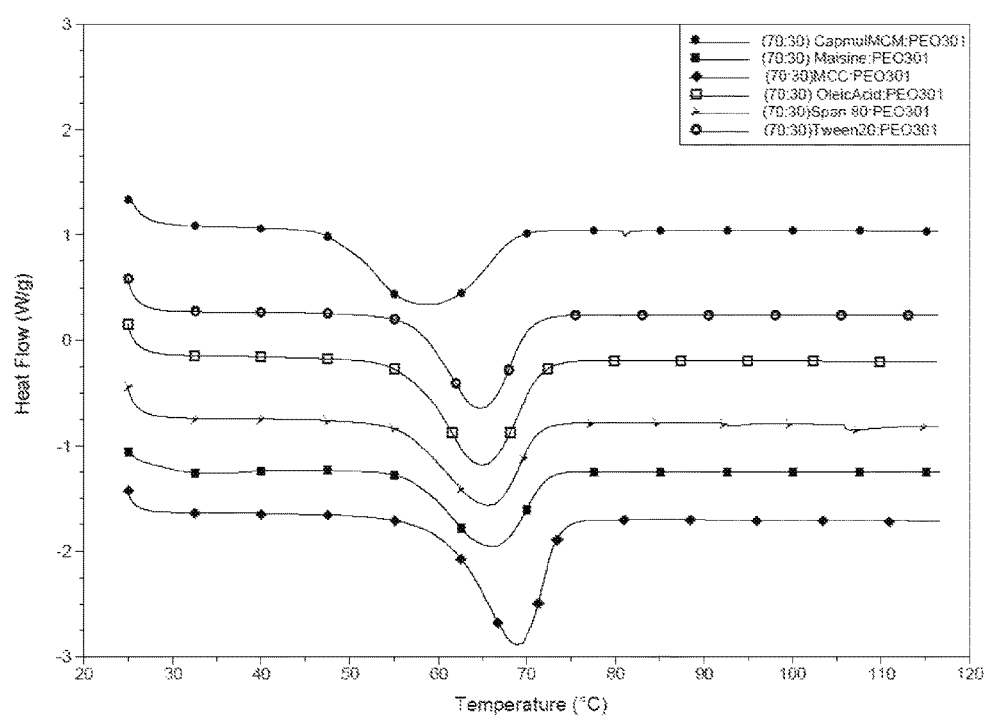
FIG. 1. Representative thermogram data demonstrating PEO melting point depression results in various flowability enhancers compared to a non-flowability enhancing excipient control.

Described herein are abuse deterrent controlled release pharmaceutical compositions. The pharmaceutical compositions described herein provide abuse deterrent matrices and methods for preparation thereof. In some embodiments, the abuse deterrent matrices described herein are a monolithic system, which have a reduced burst release effect of one or more active ingredients. In some embodiments, the abuse deterrent matrices described herein also provide for extended release profiles. Also described herein are compositions and methods for manufacturing soft or hard capsules comprising abuse deterrent controlled release pharmaceutical matrices. In some embodiments described herein, the capsule is a soft capsule. In some embodiments described herein, the soft capsule is a hard capsule. In some embodiments described herein, the soft capsule is an enteric soft capsule. In some embodiments described herein, the soft capsule is an enteric hard capsule.

The term "abuse deterrent," or "tamper resistant" as used herein, refers to a pharmaceutical composition that is resistant to intentional tampering or accessing the active pharmaceutical ingredient for recreational drug use or drug abuse.

The phrase "recreational drug use," as used herein, refers to the voluntary use of an active pharmaceutical agent or drug for a non-medical purpose to induce an effect, such as pleasure, satisfaction, euphoria, dissociation, or to enhance an experience.

The term "drug abuse," as use herein, refers to the habitual, compulsive, or recurrent use of an active pharmaceutical agent or drug, often despite negative consequences.

The term "tampering," as used herein, refers to any kind of actual or attempted physical manipulation or interference that may result in particle size reduction of a pharmaceutical composition. Tampering, as used herein also includes any actual or attempted dissolution or extraction of active pharmaceutical ingredients using solvents. Compositions that are resistant to physical tampering are formulated in such a way that the composition cannot readily reduced to a form that is suitable for abuse, such as, for example, injection or snorting, because the dosage from cannot easily be ground, grated, dissolved, extracted, or the like at any temperature. Examples of physical tampering include, but are not limited to, crushing, grinding, grating, cutting, crisping, and other methods of particle size reduction. Dissolution tampering includes actual or attempted actions to dissolve or extract active pharmaceutical ingredients using aqueous or organic solvents such as water, ethanol, isopropanol, ethyl acetate, acetone, ether, or the like, at any temperature including boiling. Tampering, as used herein, includes "dose dumping."

The term "dose dumping" or "dumping" as used herein refers to the rapid release of the entire amount or a significant fraction of an active pharmaceutical ingredient or drug. Drug abusers often intentionally pursue dumping of a drug from the dosage form.

The terms "drug", "active ingredient," "active pharmaceutical ingredient," "active pharmaceutical agent," or "API" as used herein refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

The term "anti-OIC agent" as used herein refers specifically to any agent, active ingredient, compound, substance, composition, or mixture thereof, which reduces opioid induced constipation (OIC) or one or more symptoms thereof.

The terms "dosage" or "dose" denote any form of the active ingredient formulation that contains an amount sufficient to produce a therapeutic effect with a single administration. The dosage form used herein is for oral administration. The oral dosage forms are soft capsules, enteric soft capsules, hard capsules, or enteric hard capsules.

The term "annealed" refers to a pharmaceutical composition comprising a capsule shell encapsulating a matrix fill described herein that has been heated following encapsulation to form an annealed dosage form. In some aspects, pharmaceutical compositions comprising a capsule shell encapsulating a matrix fill as described herein may be annealed at a temperature from about 50° C. to about 90° C. for about 0.1 hours to about 5 hours, including all integers within the specified ranges of temperature and time. In some aspects described herein, pharmaceutical compositions comprising a soft or hard capsule shell encapsulating a matrix fill as described herein may be annealed at a temperature of about 70° C. from about 0.15 hours to about 1 hour, including all integers within the specified range. In some aspects described herein, pharmaceutical compositions comprising a soft or hard capsule shell encapsulating a matrix fill as described herein may be annealed at a temperature of about 70° C. for about 1 hour.

The term "non-annealed" refers to a pharmaceutical composition comprising a soft or hard capsule shell encapsulating a matrix fill described herein that has not been heated following encapsulation.

The terms "active pharmaceutical ingredient load" or "drug load" as used herein refers to the quantity (mass) of the active pharmaceutical ingredient comprised in a single soft or hard capsule fill.

The term "formulation" or "composition" as used herein refers to the active pharmaceutical ingredient or drug in combination with pharmaceutically acceptable excipients. This includes orally administrable formulations as well as formulations administrable by other means.

The term "titration" as used herein refers to the incremental increase in drug dosage to a level that provides the optimal therapeutic effect.

The terms "burst release" or "bolus release" as used herein refer to an API release effect where an initial large bolus of the drug or API is released when a dosage form is placed into a dissolution medium (e.g., the gastric environment of a patient or a simulated medium). The burst release may encompass a release profile demonstrating a first order release kinetics or a period of first order release kinetics followed by zero order release. As used herein, burst release comprises releasing at least about 40% of the API within about 2 hours after ingestion by a subject or introduction into a simulated release medium.

The term "controlled release" as used herein encompasses the terms "immediate release," "modified release," "sustained release," "extended release," and "delayed release."

The terms "extended release" or "sustained release" as used herein refers to a composition that releases an active ingredient according to a desired profile over an extended period under physiological conditions or in an in vitro test. By "extended period" it is meant a continuous period of time of at least about 1 hour; about 2 hours; about 4 hours; about 6 hours; about 8 hours; about 10 hours; about 12 hours; about 14 hours; about 16 hours; about 18 hours; about 20 hours about 24 hours; or even longer; specifically, over a period of about 18 hours under physiological conditions or in an in vitro assay.

The term "modified release" as used herein refers to a composition that releases an active ingredient at a slower rate than does an immediate release formulation under physiological conditions or in an in vitro test.

The term "delayed" release" as used herein refers to a composition that releases an active ingredient after a period of time, for example minutes or hours, such that the active ingredient is not released initially. A delayed release composition may provide, for example, the release of a drug or active ingredient from a dosage form, after a certain period, under physiological conditions or in an in vitro test.

As used herein, the phrase "abuse deterrent controlled release" refers to a pharmaceutical composition comprising components or a formulation that prevents liberation of the active pharmaceutical ingredient(s) from the composition for potential abuse or dose dumping and the composition provides controlled release delivery of the active pharmaceutical ingredient upon ingestion of the composition by a subject.

The term "$C_{max}$" as used herein refers to the maximum observed blood (plasma, serum, or whole blood) concentration or the maximum blood concentration calculated or estimated from a concentration to time curve, and is expressed in units of mg/L or ng/mL, as applicable.

The term "$C_{min}$" as used herein refers to the minimum observed blood (plasma, serum, or whole blood) concentration or the minimum blood concentration calculated or estimated from a concentration to time curve, and is expressed in units of mg/L or ng/mL, as applicable.

The term "$C_{avg}$" as used herein refers to the blood (plasma, serum, or whole blood) concentration of the drug within the dosing interval, is calculated as AUC/dosing interval, and is expressed in units of mg/L or ng/mL, as applicable.

The term "$T_{max}$" as used herein refers to the time after administration at which $C_{max}$ occurs, and is expressed in units of hours (h) or minutes (min), as applicable.

The term "$AUC_{0 \to \tau}$" as used herein refers to area under the blood (plasma, serum, or whole blood) concentration versus time curve from time zero to time tau ($\tau$) over a dosing interval at steady state, where tau is the length of the dosing interval, and is expressed in units of h·mg/L or h·ng/mL, as applicable. For example, the term $AUC_{0 \to 12}$ as used herein refers to the area under the concentration versus time curve from 0 to 12 hours.

The term "$AUC_{0 \to \infty}$" as used herein refers to the area under the blood (plasma, serum, or whole blood) concentration versus time curve from time 0 hours to infinity, and is expressed in units of h·mg/L or h·ng/mL, as applicable.

The term "$AUC_{last}$" as used herein refers to the area under the blood (plasma, serum, or whole blood) concentration versus time curve at the last measurable concentration of the analyte, and is expressed in units of h·mg/L (or h·ng/mL) for at least one or more doses of the pharmaceutical compositions described herein.

The term "$AUC_{overall}$" as used herein refers to the combined area under the blood (plasma, serum, or whole blood) concentration versus time curve, and is expressed in units of h·mg/L (or h·ng/mL) for at least one or more doses of the pharmaceutical compositions described herein. In one aspect, the "$AUC_{overall}$" refers to the combined area under the blood concentration versus time curve for at least two doses of the pharmaceutical compositions described herein.

The terms "fasted-state simulated gastric fluid" or "FASSGF" and "fasted-state simulated intestinal fluid" or "FASSIF" refer to any biologically-relevant media for simulating physiological fluids under fasted (unfed) state conditions in the stomach or in the small intestine, respectively. These types of bio-relevant medias are known in the art, see, for example, International Patent Application Publication No. WO 2013/144374, which is incorporated by reference herein for its teachings thereof.

As used herein, the term "HLB" refers to the hydrophilic-lipophilic balance of the polymers described herein. The HLB may be calculated by several methodologies known in the art. For example, HLB may be calculated by the equation below:

$$HLB = 20 * M_h / M$$

where "$M_h$" is the molecular mass of the hydrophilic portion of the polymer and "M" is the molecular mass of the entire molecule. The scale ranges from 0 to 20, with a value of 0 corresponding to a complete lipophilic/hydrophobic molecule and a value of 20 corresponding to a completely hydrophilic/lipophobic molecule.

Alternatively, HLB may be obtained by calculating a value that is based on the chemical groups within the molecule according to the equation below:

$$HLB = 7 + \sum_{i=1}^{m} H_i - n \times 0.475$$

where "m" is the number of hydrophilic groups in the molecule, "$H_i$" is the value of the hydrophilic groups and "n" is the number of lipophilic groups within the molecule; See e.g., Griffin, W. C. "Classification of Surface-Active Agents by 'HLB'," *Journal of the Society of Cosmetic Chemists*, 1: 311-326 (1949); Davies, J. T. "A Quantitative Kinetic Theory of Emulsion Type, I. Physical Chemistry of the Emulsifying Agent," *Proceedings of the International Congress of Surface Activity*, 426-438 (1957), each of which are incorporated by reference herein for their teachings thereof.

The term "treating" refers to administering a therapy in an amount, manner, or mode effective to improve a condition, symptom, or parameter associated with a disorder.

The term "prophylaxis" refers to preventing or reducing the progression of a disorder, either to a statistically significant degree or to a degree detectable to one skilled in the art.

The term "substantially" as used herein means to a great or significant extent, but not completely.

The term "about" as used herein refers to any values, including both integers and fractional components that are within a variation of up to ±10% of the value modified by the term "about."

As used herein, "a" or "an" means one or more unless otherwise specified.

Terms such as "include," "including," "contain," "containing," "has," or "having," and the like, mean "comprising."

The term "or" can be conjunctive or disjunctive.

Described herein are pharmaceutical compositions comprising abuse deterrent controlled release matrices comprising active pharmaceutical ingredients. The matrix is structured to prevent or reduce the burst release and the extraction of the active pharmaceutical ingredients.

In some embodiments, the pharmaceutical composition described herein comprises a soft or hard capsule comprising an abuse deterrent controlled release matrix comprising an active pharmaceutical ingredient. In one embodiment, the active pharmaceutical ingredient is an analgesic. In another embodiment, the active pharmaceutical ingredient is an opioid analgesic.

In another embodiment, the soft or hard capsule comprising a matrix can provide controlled release properties. Such controlled release matrix fills are described in International Patent Application Publication No. WO 2005/009409 and WO 2006/096580, U.S. Patent Application Publication Nos. US 2006/0115527 and US 2007/0053868, and U.S. Pat. Nos. 8,293,270 and 8,333,989, each of which are incorporated by reference herein for such teachings. In one aspect, the soft or hard capsule and matrix can be configured to provide controlled release, extended release, sustained release, delayed release, or combinations thereof. In another aspect, the soft or hard capsule and matrix is configured to reduce or eliminate any burst release of one or more active ingredients.

In other embodiments, the pharmaceutical composition described herein comprises abuse deterrent properties. These abuse deterrent properties reduce the likelihood that the active pharmaceutical ingredient can be extracted from the composition through mechanisms, including but not limited to crushing, grating, grinding, or cutting of the capsule to expose the matrix thereby facilitating solvation or extraction of the active pharmaceutical ingredient. Exemplary and non-limiting abuse deterrent matrices useful in the pharmaceutical composition described herein may be found in PCT International Application No. PCT/US2015/024464; U.S. patent application Ser. No. 14/679,233; PCT International Application No. PCT/US2015/054443; U.S. patent application Ser. No. 14/877,208, each of which is incorporated by reference herein in their entirety. In addition, the abuse deterrent properties reduce the likelihood that the active pharmaceutical ingredient can be extracted from the composition by dissolving or extracting in ethanol solutions, dissolving in solutions having pH values from about 1 to about 12, or dissolving in household chemical compositions, including water, coffee, vinegar, cola, milk, ethanol, isopropanol, acetone, ethyl acetate, or other common solvents. In addition, the abuse deterrent properties further reduce the likelihood that the active pharmaceutical ingredient can be extracted by boiling in water or ethanol solutions.

In other embodiments described herein, the matrix comprises a lipid or lipophilic vehicle that provides a suspension or a solution of the active pharmaceutical ingredient. In one aspect, a soft or hard capsule comprising an active pharmaceutical ingredient provides controlled release of the active pharmaceutical ingredient.

In other embodiments described herein, the pharmaceutical composition provides matrix fills for the active pharmaceutical ingredient, or derivatives thereof, based on lipids or lipophilic materials. The matrices described herein have a hydrophobic (lipophilic) surface in contact with a hydrophilic soft capsule shell to minimize any potential shell-fill interactions, such as when the soft capsules are filled with hydrophilic materials. In one embodiment described herein are methods for manufacturing matrix fills comprising an abuse deterrent controlled release matrix comprising an active pharmaceutical ingredient in a soft capsule in the form of a suspension, where part or all of the active pharmaceutical ingredient is suspended within the matrix. In one embodiment described herein is a soft capsule having a shell and an abuse deterrent controlled release matrix fill, wherein the matrix includes an active pharmaceutical ingredient suspended as solid particles within the lipophilic vehicle.

In one embodiment described herein, an exemplary abuse deterrent controlled release matrix has the composition of Table 1, including all possible iterations of the specified ranges that provide 100% for the total weight percentage, including or excluding the optional colorings, flavorings, or excipients.

TABLE 1

Exemplary Abuse Deterrent Controlled Release Matrix Composition

| Component | Exemplary Components | Composition Range (%) |
|---|---|---|
| Flowability Enhancer | Mono-, di-, tri-glycerides, glyceryl monocaprylate; oleic acid; glyceryl monolinoleate (e.g., Maisine ™ 35-1) | 35-70 |
| Release Modifier | Polyethylene oxide (PEO) | 5-50 |
| Release Modifier 2 | Carboxyvinyl polymers (e.g., Carbopol ® polymers); poly(methacylic acid-co-methyl methacrylate) 1:2; hydroxy ethyl cellulose | 0-10 |
| Surfactant | Sodium lauryl sulfate; sodium octyl sulfate; sodium docusate, sodium dodecyl sulfate | 0-10 |
| Viscosity Modifier | polyvinylpyrrolidone; ethylcellulose | 0-10 |
| Antioxidant | BHT, BHA | 0-0.5 |
| Active pharmaceutical ingredient(s) | Oxycodone, hydrocodone, tapentadol | 0.1-50 |

In one embodiment, the matrix comprises one or more flowability enhancers. In one aspect, suitable flowability enhancers have surfactant like properties. Exemplary and non-limiting flowability enhancers may comprise partial triglyceride medium chain, monoglycerides, diglycerides and triglycerides, polyethylene glycol (molecular weight of about 200 or greater), medium chain triglycerides of caprylic/capric acid, glyceryl monooleate, glyceryl monostearate, glyceryl monolinoleate (e.g., Maisine™ 35-1) polyglyceryl-3-dioleate, oleoyl macrogol-6 glycerides, linoleoyl macrogol-6 glycerides. In one aspect, the flowability enhancer comprises a medium chain mono- and di-glycerides (e.g., glyceryl monocaprylate or Capmul® MCM) or. In another aspect, the flowability enhancer comprises oleic acid. In another aspect, the flowability enhancer comprises glyceryl monolinoleate.

In another embodiment, the matrix comprises one or more surfactants. In one aspect, the matrix comprises a non-ionic surfactant, an anionic surfactant, a zwitterionic surfactant, a cationic surfactant, or a combination thereof. In another aspect, the matrix comprises an ionic surfactant. Exemplary and non-limiting surfactants that may be useful in the abuse deterrent matrices described herein comprise non-ionic surfactants, such as: Pluronic® 10R5, Pluronic® 17R2, Pluronic® 17R4, Pluronic® 25R2, Pluronic® 25R4, Pluronic® 31R1, Pluronic® F 108, Pluronic® F 108 NF, Pluronic® F 108, Pluronic® F 108NF, Poloxamer 338, Pluronic® F 127, Pluronic® F 127 NF, Pluronic® F 127 NF 500 BHT Prill, Pluronic® F 127 NF Prill, Poloxamer 407, Pluronic® F 38, Pluronic® F 38 Pastille, Pluronic® F 68, Pluronic® F 68 LF Pastille, Pluronic® F 68 NF, Pluronic® F 68 NF Prill, Poloxamer 188, Pluronic® F 68 Pastille, Pluronic® F 77, Pluronic® F 77 Micropastille, Pluronic® F 87, Pluronic® F 87 NF, Pluronic® F 87 NF Prill, Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic®

L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen® 464, Alkanol® 6112, Brij® 52, Brij® 93, Brij® S2, Brij® S, Brij® 58, Brij® C10, Brij® L4, Brij® O10, Brij® O10, BRIJ® O20, Brij® S10, Brij® S20, ethylenediamine tetrakis(ethoxylate-block-propoxylate) tetrol, ethylenediamine tetrakis(ethoxylate-block-propoxylate) tetrol, ethylenediamine tetrakis(propoxylate-block-ethoxylate) tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly(ethylene glycol) sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, 2,4,7,9-tetramethyl-5-decyne-4,7-diol ethoxylate, Nonidet™ P-40, Triton™ N-101, Span® 80, Triton™ X-100, Triton™ X-114, Triton™ X-405, TWEEN® 20, TWEEN® 40, TWEEN® 60, TWEEN® 85, Zonyl® FS-300, or Zonyl® FSN.

In one embodiment, the matrix comprises one or more ionic surfactants including anionic, cationic, zwitterionic, or amphoteric surfactants. Exemplary and non-limiting anionic surfactants comprise $C_6$-$C_{25}$ alkyl surfactants, alkyl carboxylates, alkyl sulfates, alkyl sulfonates, for example, alkyl ether sulfates (e.g., having sodium and ammonium counter cations) including sodium octyl sulfate, sodium lauryl sulfate (sodium dodecyl sulfate) and sodium laureth sulfate; sulfosuccinates, such as disodium laureth sulfosuccinate, and sodium docusate. Exemplary and non-limiting cationic surfactants include quaternary ammonium salts, such as benzalkonium chloride, cetrimonium bromide, dimethyldioctadecylammonium chloride, and lauryl methyl gluceth-10 hydroxypropyl dimonium chloride. Exemplary and non-limiting zwitterionic or amphoteric hydrocarbon surfactants include, but are not limited to, those which contain in the same molecule, amino and carboxy, sulfonic, and sulfuric ester moieties, such as amine oxides, aminopropionates, sultaines, sulfobetaines, alkyl sulfobetaines, alkyl betaines, alkylamidobetaines, dihydroxyethyl glycinates, imidazoline acetates, imidazoline propionates, and imidazoline sulfonates. Commercially available zwitterionic surfactants include Chembetaine CAS (Lubrizol Inc.), Mirataine™ H2C-HA (sodium laurimino dipropionate), Miranol™ C2M-SF Conc. (sodium cocoampho propionate), Mirataine™ CB (cocamidopropyl betaine), Mirataine™ CBS (cocamidopropyl hydroxysultaine), and Miranol™.

Additional exemplary and non-limiting flowability enhancers may include higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyl dodecanol; myristyl alcohol; isopropyl myristate, isopropyl palmitate, stearic acid, stearyl alcohol, and others known in the art.

In another embodiment, the flowability enhancer has a hydrophilic lipophilic balance (HLB) ranging from about 0 to about 20. In one aspect, the flowability enhancer has an HLB value of less than 10. In another aspect, the flowability enhancer has an HLB value of between 1 and 6. In another aspect, the flowability enhancer has an HLB value of less than 5.

In another embodiment, the surfactant has a hydrophilic lipophilic balance (HLB) ranging from about 1 to about 50, including all integers within the specified range. In one aspect, the surfactant enhancer is an ionic surfactant enhancer with an HLB of greater than 20. In one aspect, the surfactant has an HLB value of about 1 to about 20. In another aspect, the surfactant has an HLB value of about 20 to about 30. In another aspect, the surfactant has an HLB value of about 20 to about 40. In another aspect, the surfactant has an HLB value of about 30 to about 40. In another aspect, the surfactant has an HLB value of about 40 to about 50. In another aspect, the surfactant has an HLB value of about 35 to about 45. In another aspect, the surfactant has an HLB value of about 35 to about 40. In another aspect, the surfactant has an HLB value of about 40 to about 45. In another aspect, the surfactant has an HLB value greater than 20. In another aspect, the surfactant has an HLB value greater than 30. In another aspect, the surfactant has an HLB value about 40 or greater. In another aspect, the surfactant has an HLB value of about 40. The HLB characteristic of surfactants and other compounds can be determined in accordance with "*Physical Pharmacy: Physical Chemical Principles in the Pharmaceutical Sciences*," Fourth Edition, pp. 371-373, A. Martin, Ed., Lippincott Williams & Wilkins, Philadelphia (1993).

In another embodiment, the matrix may further include one or more lipid or lipophilic vehicles, such as olive oil, soybean oil, sunflower oil, canola oil, palmitoleic acid, oleic acid, myristoleic acid, linoleic acid, arachidonic acid, vegetable oil, corn oil, sun flower oil, coconut oil, cocoa oil, peanut oil, almond oil, cottonseed oil, persic oil, sesame oil, squalane oil, castor oil, fish oil, paraffin oil, or mineral oil.

In another embodiment, the matrix may comprise one or more release modifiers. In one aspect, the release modifier comprises a high molecular weight polyethylene oxide or a carboxyvinyl polymer, or a combination thereof. As described herein, high molecular weight polyethylene oxide polymers have an approximate molecular weight based on viscosity or rheology ($M_v$) of at least about 600,000 to about 10,000,000 or greater. In one aspect, the release modifier may comprise a high molecular weight polyethylene oxide having a molecular weight ($M_v$) of about 600,000 to about 10,000,000, including each integer within the specified range. In another aspect, the release modifier may comprise a high molecular weight polyethylene oxide having a molecular weight ($M_v$) of about 5,000,000 to about 10,000,000, including each integer within the specified range. In another aspect, the release modifier may comprise a high molecular weight polyethylene oxide having a molecular weight ($M_v$) of about 4,000,000 to about 7,000,000, including each integer within the specified range. In another aspect, the release modifier may comprise a high molecular weight polyethylene oxide having a molecular weight ($M_v$) of about 600,000, about 700,000, about 800,000, about 900,000, about 1,000,000, about 2,000,000, about 3,000,000, about 4,000,000, about 5,000,000, about 6,000,000, about 7,000,000, about 8,000,000, about 9,000,000 or about 10,000,000. In another aspect, the release modifier may comprise a high molecular weight polyethylene oxide having a molecular weight ($M_v$) of about 4,000,000. In another aspect, the release modifier may comprise a high molecular weight polyethylene oxide having a molecular weight ($M_v$) of about 5,000,000. In another aspect, the release modifier may comprise a high molecular weight polyethylene oxide having a molecular weight ($M_v$) of about 7,000,000.

The molecular weight measurements of polyethylene oxide may be approximated using rheological measurements using a viscometer. For example, polyethylene oxide is considered to have an approximate molecular weight ($M_v$) of 600,000 when a 5% (by wt) aqueous solution of polyethylene oxide using a Brookfield viscometer Model RVF, spindle No. 2, at 2 rpm, at 25° C. shows a viscosity range of 30 to 50 mPa s (cP). Polyethylene oxide is considered to have an approximate molecular weight ($M_v$) of 1,000,000 when a 2% (by wt) aqueous solution of polyethylene oxide using a Brookfield viscometer Model RVF, spindle No. 1, at 10 rpm, at 25° C. shows a viscosity range of 400 to 800 mPa s (cP). Polyethylene oxide is considered to have an approximate molecular weight ($M_v$) of 2,000,000 when a 2% (by wt) aqueous solution of polyethylene oxide using a Brookfield viscometer Model RVF, spindle No. 3, at 10 rpm, at 25° C. shows a viscosity range of 2000 to 4000 mPa s (cP). Polyethylene oxide is considered to have an approximate molecular weight ($M_v$) of 4,000,000 when a 1% (by wt) aqueous solution of polyethylene oxide using a Brookfield viscometer Model RVF, spindle No. 2, at 2 rpm, at 25° C. shows a viscosity range of 1650 to 5500 mPa s (cP). Polyethylene oxide is considered to have an approximate molecular weight ($M_v$) of 5,000,000 when a 1% (by wt) aqueous solution of polyethylene oxide using a Brookfield viscometer Model RVF, spindle No. 2, at 2 rpm, at 25° C. shows a viscosity range of 5500 to 7500 mPa s (cP). Polyethylene oxide is considered to have an approximate molecular weight ($M_v$) of 7,000,000 when a 1% (by wt) aqueous solution of polyethylene oxide using a Brookfield viscometer Model RVF, spindle No. 2, at 2 rpm, at 25° C. shows a viscosity range of 7500 to 10,000 mPa s (cP). Polyethylene oxide is considered to have an approximate molecular weight ($M_v$) of 8,000,000 when a 1% (by wt) aqueous solution of polyethylene oxide using a Brookfield viscometer Model RVF, spindle No. 2, at 2 rpm, at 25° C. shows a viscosity range of 10,000 to 15,000 mPa s (cP). Suitable polyethylene oxide polymers with the above described viscosity and molecular weight values that are useful for the matrices described are, for example, POLYOX™ polymers, such as WSR-205, WSR-1105, WSR N-12K, WSR N-60K, WSR-301, WSR Coagulant, WSR-303, WSR 308, UCARFLOC Polymers 300, 302, 304, and 309 commercially available from Dow Chemical Co.

In another embodiment, the composition comprises one or more additional release modifiers comprising carboxyvinyl polymers (e.g., Carbopol® polymer), poly(methacylic acid-co-methyl methacrylate) 1:2 (e.g., Eudragit® S100), hydroxy ethyl cellulose, or a mixture or combination thereof.

In another embodiment, the composition comprises one or more viscosity modifiers. Suitable and non-limiting viscosity modifiers that may be present in the matrices described herein comprise methylcellulose, ethylcellulose, hydroxypropylmethyl cellulose, hydroxypropyl cellulose, hydroxyethyl cellulose, hydroxymethyl cellulose, polymethylmethacrylate, polyhydroxyethylmethacrylate, polyvinylpyrrolidone, copovidone, polyvinyl alcohol, a copolymer of polyvinylpyrrolidone and polyvinyl acetate, or combinations thereof. For example, polymers commercially available as Methocel™ K100M, Methocel™ A4M, Ethocel™ Premium LV CR, K4M Premium CR, K15M Premium CR, K100 Premium CR, E4M Premium CR, E10M Premium CR, or E4M Premium (Dow Chemical Co.), CELLOSIZE™, or WALOCEL™ CRT may be used in the abuse deterrent matrices described herein. These viscosity modifiers may comprise a viscosity of about 50 cP to about 100,000 cP, including each integer within the specified range. For example, these additional release modifiers may comprise a viscosity of about 50 cP, about 100 cP, about 200 cP, about 300 cP, about 400 cP, about 500 cP, about 750 cP, about 1,000 cP, about 1,500 cP, about 2,000 cP, about 2,500 cP, about 3,000 cP, about 3,500 cP, about 4,000 cP, about 4,500 cP, about 5,000 cP, about 6,000 cP, about 7,000 cP, about 8,000 cP, about 9,000 cP, or about 10,000 cP, about 15,000 cP, about 20,000 cP, about 30,000 cP, about 40,000 cP, about 50,000 cP, about 60,000 cP, about 70,000 cP, about 80,000 cP, about 90,000 cP, about 100,000 cP, greater than 100,000 cP, or even greater. In one embodiment, the matrix comprises hydroxylpropyl methylcellulose (e.g., Methocel™ K100M). In another embodiment, the matrix comprises ethylcellulose (e.g., Ethocel™ 20 cP). In another embodiment, the matrix comprises a polyvinylpyrrolidone (e.g., polyvinylpyrrolidone K90).

In another embodiment, the abuse-deterrent matrix may optionally comprise one or more antioxidants. Suitable antioxidants comprise tocopherols (e.g., alpha-tocopherol, beta-tocopherol, gamma-tocopherol, or delta-tocopherol), butylated hydroxytoluene (BHT), butylated hydroxyanisole (BHA), citric acid, ascorbic acid, phenolic diterpenes (e.g., carnosic acid, carnosol, rosmanol, epirosmanol, isorosmanol, or methyl carnosate), rosmarinic acid, eugenol, eugenyl acetate, clove bud extract, methanolic extract, tea catechins (e.g., epigallocatechin gallate, epicatechin gallate, epigallocatechin, or epicatechin), or combinations thereof.

In one embodiment described herein, the abuse deterrent matrix may comprise one or more flowability enhancers, one or more release modifiers, one or more active pharmaceutical ingredients, optionally one or more antioxidants, optionally one or more viscosity modifiers, optionally one or more hydrophilic vehicles, and optionally one or more other pharmaceutically acceptable excipients in a weight percentage amount of the matrix fill mass as further described herein.

In another embodiment, the one or more flowability enhancers comprises from about 40% to about 80% of the matrix fill mass, including all integers within the specified range. In one aspect, the one or more flowability enhancers comprises from about 50% to about 80% of the matrix fill mass, including all integers within the specified range. In another aspect, the one or more flowability enhancers comprises from about 50% to about 60% of the matrix fill mass, including all integers within the specified range. In another aspect, the one or more flowability enhancers comprises from about 50% to about 60% of the matrix fill mass, including all integers within the specified range. In another aspect, the one or more flowability enhancers comprises from about 40%, about 45%, about 50%, about 55%, about 60%, about 65%, about 70%, about 75%, or about 80% of the matrix fill mass.

In another embodiment, the one or more release modifiers comprises from about 5% to about 50% of the matrix fill mass, including all integers within the specified range. In one aspect, the one or more release modifiers comprises from about 5% to about 25% of the matrix fill mass, including all integers within the specified range. In one aspect, the one or more release modifiers comprises from about 10% to about 30% of the matrix fill mass, including all integers within the specified range. In one aspect, the one or more release modifiers comprises from about 20% to about 40% of the matrix fill mass, including all integers within the specified range. In one aspect, the one or more release modifiers comprises from about 25% to about 50% of the matrix fill mass, including all integers within the specified range. In another aspect, the one or more release modifiers comprises from about 25% to about 40% of the matrix fill mass, including all integers within the specified range. In another aspect, the one or more release modifiers comprises from about 25% to about 35% of the matrix fill mass, including all integers within the specified range. In another aspect, the one or more release modifiers comprises about 5%, about 10%, about 15%, about 20%, about 25%, about 30%, about 35%, about 40%, about 45%, or about 50% of the matrix fill mass.

In another embodiment, the one or more viscosity modifiers may comprise from about 0.5% to about 8% of the matrix fill mass, including all integers within the specified range. In one aspect, the one or more viscosity modifiers may comprise from about 0.5% to about 5% of the matrix fill mass, including all integers within the specified range. In another aspect, the one or more viscosity modifiers may comprise from about 0.5% to about 3% of the matrix fill mass, including all integers within the specified range. In another aspect, the one or more viscosity modifiers may comprise from about 0.5% to about 2% of the matrix fill mass, including all integers within the specified range. In another aspect, the one or more viscosity modifiers may comprise about 0.5%, about 0.75%, about 1%, about 2%, about 3%, about 4%, about 5%, about 6%, about 7%, or about 8%, of the matrix fill mass. In another aspect, matrix fill mass may not have any viscosity modifier.

In another embodiment, the one or more surfactants may comprise from about 0.5% to about 10% of the matrix fill mass, including all integers within the specified range. In one aspect, the one or more surfactants may comprise from about 0.5% to about 5% of the matrix fill mass, including all integers within the specified range. In another aspect, the one or more surfactants may comprise from about 0.5% to about 3% of the matrix fill mass, including all integers within the specified range. In another aspect, the one or more surfactants may comprise from about 0.5% to about 2% of the matrix fill mass, including all integers within the specified range. In another aspect, the one or more surfactants may comprise about 0.5%, about 0.75%, about 1%, about 2%, about 3%, about 4%, about 5%, about 6%, about 7%, about 8%, about 9%, or about 10% of the matrix fill mass.

In another embodiment, one or more antioxidants may comprise from about 0.1% to about 0.5% of the matrix mass, including all integers within the specified range. In one aspect, the one or more antioxidants may comprise about 0.3%, 0.4%, or 0.5% of the matrix fill mass.

In another embodiment, the one or more hydrophilic polymers comprises from about 1% to about 50% by weight of the matrix fill mass, including all integers within the specified range. In one aspect, the one or more hydrophilic polymer s comprises from about 1% to about 30% of the matrix fill mass, including all integers within the specified range. In another aspect, the one or more hydrophilic polymers comprises from about 25% to about 40% of the matrix fill mass, including all integers within the specified range. In another aspect, the one or more hydrophilic polymers comprises from about 25% to about 35% of the matrix fill mass, including all integers within the specified range. In one aspect, the one or more hydrophilic polymer s comprises from about 1% to about 10% of the matrix fill mass, including all integers within the specified range. In another aspect, the one or more hydrophilic polymers comprises about 1%, about 5%, about 10% about, 20%, about 25%, about 30%, about 35%, about 40%, about 45%, or about 50% of the matrix fill mass.

In another embodiment, the one or more active pharmaceutical ingredient comprises from about 0.1% to about 50% of the matrix fill mass, including all integers within the specified range. In another embodiment, the one or more active pharmaceutical ingredient comprises from about 1% to about 50% of the matrix fill mass, including all integers within the specified range. In another embodiment, the one or more active pharmaceutical ingredient comprises from about 1% to about 25% of the matrix fill mass, including all integers within the specified range. In one aspect, the active pharmaceutical ingredient comprises about 5% of the matrix fill mass. In one aspect, the active pharmaceutical ingredient comprises about 7% of the matrix fill mass. In one aspect, the active pharmaceutical ingredient comprises about 10% of the matrix fill mass. In one aspect, the active pharmaceutical ingredient comprises about 20% of the matrix fill mass. In one aspect, the active pharmaceutical ingredient comprises about 25% of the matrix fill mass.

In another embodiment, the weight percentage ratio of release modifier to flowability enhancer ranges from about 0.2:1 to about 1:1.5, including all iterations of ratios within the specified range. In one aspect, the weight percentage ratio of release modifier to flowability enhancer ranges from about 0.2:1 to about 0.75:1, including all iterations of ratios within the specified range. In one aspect, the weight percentage ratio of release modifier to flowability enhancer ranges from about 0.2:1 to about 0.5:1, including all iterations of ratios within the specified range. In one aspect, the weight percentage ratio of release modifier to flowability enhancer ranges from about 0.2:1, about 0.3:1, about 0.4:1, about 0.5:1, about 0.6:1, about 0.7:1, about 0.9:1, about 1:1, about 1.1:1, or about 1.2:1.

In another embodiment, the weight percentage ratio of flowability enhancer to surfactant ranges from about 2:1 to about 35:1, including all iterations of ratios within the specified range. In one aspect, the weight percentage ratio of flowability enhancer to surfactant ranges from about 8:1 to about 25:1, including all iterations of ratios within the specified range. In one aspect, the weight percentage ratio of flowability enhancer to surfactant ranges from about 12:1 to about 22:1, including all iterations of ratios within the specified range. In one aspect, the weight percentage ratio of flowability enhancer to surfactant ranges from about 2:1, about 4:1, about 6:1, about 8:1, about 10:1, about 12:1, about 14:1, about 16:1, about 18:1, about 20:1, about 22:1, about 24:1, about 26:1, about 28:1, about 30:1, about 32:1, about 34:1, or about 36:1.

In another embodiment, the weight percentage ratio of release modifier to surfactant ranges from about 1:1 to about 20:1, including all iterations of ratios within the specified range. In one aspect, the weight percentage ratio of release modifier to surfactant ranges from about 2:1 to about 16:1, including all iterations of ratios within the specified range. In one aspect, the weight percentage ratio of release modifier to surfactant ranges from about 8:1 to about 12:1, including all iterations of ratios within the specified range. In one aspect, the weight percentage ratio of release modifier to surfactant ranges from about 2:1, about 4:1, about 6:1, about 8:1, about 10:1, about 12:1, about 14:1, about 16:1, about 18:1, or about 20:1.

In another embodiment, the weight percentage ratio of active pharmaceutical ingredient to the total matrix fill mass ranges from about 1:1000 to about 1:3, including all iterations of ratios within the specified range. In another embodiment, the weight percentage ratio of active pharmaceutical ingredient to the total matrix fill mass ranges from about 1:100 to about 1:2, including all iterations of ratios within the specified range. In another embodiment, the weight percentage ratio of active pharmaceutical ingredient to the total matrix fill mass ranges from about 1:15 to about 1:2, including all iterations of ratios within the specified range. In one aspect, the weight percentage ratio of active pharmaceutical ingredient to the total matrix fill mass is about 1:100. In another aspect, the weight percentage ratio of active pharmaceutical ingredient to the total matrix is about 1:10. In another aspect, the weight percentage ratio of active pharmaceutical ingredient to the total matrix fill mass is about 1:7.5. In another aspect, the weight percentage ratio of active pharmaceutical ingredient to the total matrix fill mass is about 1:5. In another aspect, the weight percentage ratio of active pharmaceutical ingredient to the total matrix fill mass is about 1:3. In another aspect, the weight percentage ratio of active pharmaceutical ingredient to the total matrix fill mass is about 1:2.

In one embodiment described herein, the abuse deterrent matrix may comprise one or more flowability enhancers, one or more release modifiers, one or more active pharmaceutical ingredients, one or more surfactants, optionally one or more viscosity modifiers, wherein the matrix comprises any one of the compositions of Tables 4-8.

It was found that the addition of one or more flowability enhancers such as mono- or di-glycerides (e.g., Capmul® MCM), oleic acid, and glyceryl monolinoleate (e.g., Maisine™ 35-1) increases the flowability of the one or more release modifiers (e.g., high molecular weight polyethylene oxide), and thus, provides for a flowable matrix suitable for encapsulation in the soft or hard capsule shells as described herein. For example, using a conventional hydrophilic vehicle, such as polyethylene glycol, it was demonstrated that a carrier comprising polyethylene glycol had a high degree of miscibility with the high molecular weight polyethylene oxide. The resulting mixtures of polyethylene oxide and polyethylene glycol became highly viscous at room temperature, which complicates further processing steps. Further, it was found that certain oils and lipophilic vehicles are not suitable as a flowability enhancer for the one or more release modifiers.

Thus, without being bound by any theory, it is believed that the flowable characteristics of the matrices described herein may be due to the limited miscibility of the one or more release modifiers and the one or more flowability enhancers described herein at room temperature. For example, it was found that mono- or di-glycerides (e.g., Capmul® MCM), oleic acid, and glyceryl monolinoleate (e.g., Maisine™ 35-1) allows adequate matrix flowability at room temperature due to limited solubilization of high molecular weight polyethylene oxide that allows standard encapsulation techniques to be employed. It was further found that matrix compositions comprising a flowability enhancer with surfactant-like properties, such as for example, mono- or di-glycerides (e.g., Capmul® MCM), oleic acid, or glyceryl monolinoleate (e.g., Maisine™ 35-1) and a high molecular weight polyethylene oxide had a fluid-like consistency at room temperature.

It was further demonstrated that the flowability enhancer and polyethylene oxide became more miscible after being heated to about 70° C. Surprisingly, it was discovered that these matrices having the flowability enhancers, such as mono- or di-glycerides (e.g., Capmul® MCM), oleic acid, or glyceryl monolinoleate (e.g., Maisine™ 35-1) when heated to an elevated temperature of about 70° C. and then cooled back to room temperature, became a semi-solid elastic material having an increased Young's modulus. In contrast, it was also unexpectedly demonstrated that this solidifying effect did not occur for compositions having soybean oil as a flowability enhancer. Furthermore, it was advantageously found that the process of heating and cooling the matrices comprising polyethylene oxide and a suitable flow ability enhancer further allow for reduced levels of polyethylene oxide to be used, while exhibiting effective abuse deterrent and controlled release properties, which has previously been unrealized.

Without being bound by any theory, it is thought that the release modifier is suspended in the flowability enhancer throughout the processing steps. During the annealing steps, the release modifier is believed to become molten. The two components, therefore, may be miscible at this point. When cooled, the release modifier subsequently recrystallizes and forms a semi-solid elastic matrix that encapsulates the flowability enhancer and an active pharmaceutical ingredient. For example, high molecular weight polyethylene oxide is a semi-crystalline polymer known to melt at about 70° C. and may be solubilized or more completely solubilized in a suitable flowability enhancer, such as mono- or di-glycerides (e.g., Capmul® MCM), oleic acid, and glyceryl monolinoleate (e.g., Maisine™ 35-1) at these elevated temperatures. After subsequent cooling, the polyethylene oxide and flowability enhancer mixture then partially solidify to form a semi-solid elastic matrix fill composition. Thus, this annealing process results in the formation of an elastic semi-solid matrix through melting and subsequent solidification of the release modifier and flowability enhancer mixture.

Thus, as described herein, the heated pharmaceutical compositions comprising the abuse deterrent matrix fills are in some embodiments annealed by heating the compositions. In some embodiments, the pharmaceutical compositions comprising a soft or hard capsule shell encapsulating a matrix fill as described herein may be annealed at a temperature of about 70° C. for about 1 hour or less. These annealed and semi-solid elastic matrices demonstrate abuse deterrent characteristics.

A common method for extracting abuse prone drugs is by boiling the composition. It was found that the abuse deterrent matrix fills described herein further provide for abuse deterrence by reducing the percentage of released active pharmaceutical ingredient released during boiling, suggesting that the matrices described herein maintain a semi-solid elastic material at high temperatures (e.g., in excess of 90-100° C.). Without wishing to be bound by any theory, it is thought that the lipophilic nature of the matrices in combination with a high molecular weight polyethylene oxide provide for some aspects of these abuse deterrent characteristics. Further, the semi-solid elastic characteristics of the abuse deterrent matrix fills described herein further prevent or reduce the likelihood for the extraction of active pharmaceutical ingredients through the additional means of crushing, grating, grinding, or cutting the dosage forms further described herein.

Another common method for extracting abuse prone drugs is through ethanol based extraction of the composition. It was found that the abuse deterrent matrices described herein further reduce the extraction of one or more active pharmaceutical ingredients in high percentage Ethanol solutions (e.g., 80%), while maintaining desired release rates in gastric-like environments. Thus, the presence of the components of the abuse deterrent matrix compositions described herein function to inhibit drug release from the pharmaceutical compositions described herein using common attempts of drug extraction. Thus, the matrix compositions described herein have abuse deterrent properties by preventing the liberation of the active ingredient for injection or insufflation and prevent solvation, dissolution, or extraction of the active pharmaceutical ingredient by use of aqueous or organic solutions. Furthermore, the matrix compositions also provide controlled release delivery of the active pharmaceutical ingredient after ingestion by a subject.

The inclusion of additional water soluble surfactants was found to provide for additional abuse deterrent controlled release properties. In some aspects, the inclusion of the surfactant mitigated the burst release of active pharmaceutical ingredients from the formulation (e.g., hydrocodone). It was found that once a critical concentration of SLS is reached within the matrix, the in vitro release rate of the active ingredient is substantially decreased. This reduced release rate is observed to continue throughout the duration of the in vitro dissolution test. These results are particularly surprising because it would be expected that the inclusion of a water soluble surfactant such as, for example, sodium lauryl sulfate, would defeat the controlled release properties of the dosage form, particularly when exposed to boiling aqueous conditions.

In addition to reducing the burst release effects and reducing active ingredient release under boiling conditions, the inclusion of suitable surfactants also may prevent abuse by eliciting an irritation response. For example, surfactants are known to produce a tissue irritation when applied to the nasal mucosa and will cause local irritation at injection sites. This irritant response occurs when the dosage forms are administered as is by nasal or injection routes. The irritant responses persist following extraction procedures using common aqueous and organic solvents because the irritant surfactant co-elutes with the drug. In addition, some surfactants such as sodium docusate, which is commonly used as a stool softener/laxative, can reduce opioid-induced constipation while also preventing abuse by inducing undesirable gastrointestinal effects if large quantities of the composition are ingested. Similar gastrointestinal effects can be obtained by the inclusion of other surfactants into the matrix. Thus, the surfactants described herein increase the controlled release properties of the matrices described herein while also causing discomfort to abusers when tampered.

In one embodiment, the matrix contains an active pharmaceutical ingredient in a suspended form, soluble form, insoluble form, or combinations thereof. The active pharmaceutical ingredient can be dispersed in the internal phase as a suspension form. A suspension as used herein means the API does not dissolve in one of the phases and remains as a solid.

In another embodiment, the matrix contains an active pharmaceutical ingredient useful for the treatment of pain. In one embodiment, the active pharmaceutical ingredient includes one or more of tapentadol, oxycodone, morphine, morphine analogues, or morphine antagonists, codeine, morphine, methadone, fentanyl and analogs, opioid pain relievers: oxycodone hydrochloride, hydrocodone bitartrate hydromorphone, oxymorphone, meperidine, propoxyphene, flunitrazepam, barbiturates, amytal, nembutal, seconal, phenobarbital; benzodiazepines, zolpidem, zaleplon, eszopiclone, amphetamines, methylphenidate, or combinations thereof.

In another embodiment, the matrix comprises one or more active pharmaceutical ingredients (API). In one aspect, the active pharmaceutical ingredient is useful in treating pain. In one aspect, the active pharmaceutical ingredient comprises tapentadol, oxycodone, hydrocodone, or codeine. In one aspect, the active pharmaceutical ingredient comprises oxycodone or hydrocodone. In one aspect the active pharmaceutical ingredient comprises oxycodone hydrochloride or hydrocodone bitartrate.

Examples of specific active drug substances suitable for use in the pharmaceutical compositions provided herein include: anti-inflammatory and antirheumatic active drug substances, such as, for example: butylpyrazolidine, phenylbutazone, mofebutazone, oxyphenbutazone, clofezone, kebuzone, acetic acid derivatives and related substances, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, oxicam, piroxicam, tenoxicam, droxicam, lornoxicam, meloxicam, methotrexate, propionic acid derivatives, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, fenamates, mefenamic acid, tolfenamic acid, flufenamic acid, meclofenamic acid, coxibs, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, feprazone, dipyrocetyl, acetylsalicylic acid, quinolines, oxycinchophen, gold preparations, sodium aurothiomalate, sodium aurotiosulfate, auranofin, aurothioglucose, aurotioprol, penicillamine or bucillamine.

In another embodiment, suitable active pharmaceutical ingredients can comprise analgesics, such as, for example: opioids, natural opium alkaloids, morphine, opium, hydromorphone, nicomorphine, oxycodone, dihydrocodone, diamorphine, tapentadol, papaveretum, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, difluni sal, potassium salicylate, guaceti sal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics, such as, for example: rimazolium, glafenine, floctafenine, viminol, nefopam, flupirtine, or ziconotide.

In another embodiment, suitable active pharmaceutical ingredients can comprise anaesthetics, such as, for example: ethers, diethyl ether, vinyl ether, halogenated hydrocarbons, halothane, chloroform, methoxyflurane, enflurane, trichloroethylene, isoflurane, desflurane, sevoflurane, barbiturates, methohexital, hexobarbital, thiopental, narcobarbital, opioid anaesthetics, fentanyl, alfentanil, sufentanil, phenoperidine, anileridine, remifentanil, other general anaesthetics, such as, for example: droperidol, ketamine, propanidid, alfaxalone, etomidate, propofol, hydroxybutyric acid, nitrous oxide, esketamine, xenon, esters of aminobenzoic acid, metabutethamine, procaine, tetracaine, chloroprocaine, benzocaine, amides, bupivacaine, lidocaine, mepivacaine, prilocaine, butanilicaine, cinchocaine, etidocaine, articaine, ropivacaine, levobupivacaine, esters of benzoic acid, cocaine, other local anaesthetics, such as, for example: ethyl chloride, dyclonine, phenol, or capsaicin.

In another embodiment, suitable active pharmaceutical ingredients can comprise antimigraine active drug substances, such as, for example: ergot alkaloids, dihydroergotamine, ergotamine, methysergide, lisuride, corticosteroid derivatives, flumedroxone, selective serotonin ($5HT^1$) agonists, sumatriptan, naratriptan, zolmitriptan, rizatriptan, almotriptan, eletriptan, frovatriptan, other antimigraine preparations, pizotifen, clonidine, iprazochrome, dimetotiazine, or oxetorone.

In another embodiment, suitable active pharmaceutical ingredients can comprise antiepileptic active drug substances, such as, for example: barbiturates and derivatives, methylphenobarbital, phenobarbital, primidone, barbexaclone, metharbital, hydantoin derivatives, ethotoin, phenytoin, amino(diphenylhydantoin) valeric acid, mephenytoin, fosphenytoin, oxazolidine derivatives, paramethadione, trimethadione, ethadione, succinimide derivatives, ethosuximide, phensuximide, mesuximide, benzodiazepine derivatives, clonazepam, carboxamide derivatives, carbamazepine, oxcarbazepine, rufinamide, fatty acid derivatives, valproic acid, valpromide, aminobutyric acid, vigabatrin, progabide, tiagabine, other antiepileptics, such as, for example: sultiame, phenacemide, lamotrigine, felbamate, topiramate, gabapentin, pheneturide, levetiracetam, zonisamide, pregabalin, stiripentol, lacosamide, or beclamide.

In another embodiment, suitable active pharmaceutical ingredients can comprise anticholinergic active drug substances, such as, for example: tertiary amines, trihexyphenidyl, biperiden, metixene, procyclidine, profenamine, dexetimide, phenglutarimide, mazaticol, bornaprine, tropatepine, ethers chemically close to antihistamines, etanautine, orphenadrine (chloride), ethers of tropine or tropine derivatives, benzatropine, or etybenzatropine.

In another embodiment, suitable active pharmaceutical ingredients can comprise dopaminergic active drug substances, such as, for example: dopa and dopa derivatives, levodopa, melevodopa, etilevodopa, adamantane derivatives, amantadine, dopamine agonists, bromocriptine, pergolide, dihydroergocryptine mesylate, ropinirole, pramipexole, cabergoline, apomorphine, piribedil, rotigotine, monoamine, oxidase B inhibitors, selegiline, rasagiline, other dopaminergic agents, such as, for example: tolcapone, entacapone, or budipine.

In another embodiment, suitable active pharmaceutical ingredients can comprise antipsychotic active drug substances, such as, for example: phenothiazines with aliphatic side-chain, chlorpromazine, levomepromazine, promazine, acepromazine, triflupromazine, cyamemazine, chlorproethazine, phenothiazines with piperazine structure, dixyrazine, fluphenazine, perphenazine, prochlorperazine, thiopropazate, trifluoperazine, acetophenazine, thioproperazine, butaperazine, perazine, phenothiazines with piperidine structure, periciazine, thioridazine, mesoridazine, pipotiazine, butyrophenone derivatives, haloperidol, trifluperidol, melperone, moperone, pipamperone, bromperidol, benperidol, droperidol, fluanisone, indole derivatives, oxypertine, molindone, sertindole, ziprasidone, thioxanthene derivatives, flupentixol, clopenthixol, chlorprothixene, tiotixene, zuclopenthixol, diphenylbutylpiperidine derivatives, fluspirilene, pimozide, penfluridol, diazepines, oxazepines, thiazepines, loxapine, clozapine, olanzapine, quetiapine, neuroleptics, tetrabenazine, benzamides, sulpiride, sultopride, tiapride, remoxipride, amisulpride, veralipride, levosulpiride, lithium, other antipsychotics, such as, for example prothipendyl, risperidone, clotiapine, mosapramine, zotepine, aripiprazole, or paliperidone.

In another embodiment, suitable active pharmaceutical ingredients can comprise anxiolytic active drug substances, such as, for example: benzodiazepine derivatives, diazepam, chlordiazepoxide, medazepam, oxazepam, potassium clorazepate, lorazepam, adinazolam, bromazepam, clobazam, ketazolam, prazepam, alprazolam, halazepam, pinazepam, camazepam, nordazepam, fludiazepam, ethyl loflazepate, etizolam, clotiazepam, cloxazolam, tofisopam, diphenylmethane derivatives, hydroxyzine, captodiame, carbamates, meprobamate, emylcamate, mebutamate, dibenzo-bicyclo-octadiene derivatives, benzoctamine, azaspirodecanedione derivatives, buspirone, other anxiolytics, such as, for example: mephenoxalone, gedocarnil, or etifoxine.

In another embodiment, suitable active pharmaceutical ingredients can comprise hypnotic and sedative active drug substances, such as, for example: barbiturates, pentobarbital, amobarbital, butobarbital, barbital, aprobarbital, secobarbital, talbutal, vinylbital, vinbarbital, cyclobarbital, heptabarbital, reposal, methohexital, hexobarbital, thiopental, ethallobarbital, allobarbital, proxibarbal, aldehydes and derivatives, chloral hydrate, chloralodol, acetylglycinamide chloral hydrate, dichloralphenazone, paraldehyde, benzodiazepine emepronium derivatives, flurazepam, nitrazepam, flunitrazepam, estazolam, triazolam, lormetazepam, temazepam, midazolam, brotizolam, quazepam, loprazolam, doxefazepam, cinolazepam, piperidinedione derivatives, glutethimide, methyprylon, pyrithyldione, benzodiazepine related drugs, zopiclone, zolpidem, zaleplon, ramelteon, other hypnotics and sedatives, such as, for example: methaqualone, clomethiazole, bromisoval, carbromal, scopolamine, propiomazine, triclofos, ethchlorvynol, valerian, hexapropymate, bromides, apronal, valnoctamide, methylpentynol, niaprazine, melatonin, dexmedetomidine, or dipiperonylaminoethanol.

In another embodiment, suitable active pharmaceutical ingredients can comprise antidepressant active drug substances, such as, for example: non-selective monoamine reuptake inhibitors, desipramine, imipramine, imipramine oxide, clomipramine, opipramol, trimipramine, lofepramine, dibenzepin, amitriptyline, nortriptyline, protriptyline, doxepin, iprindole, melitracen, butriptyline, dosulepin, amoxapine, dimetacrine, amineptine, maprotiline, quinupramine, selective serotonin reuptake inhibitors, zimeldine, fluoxetine, citalopram, paroxetine, sertraline, alaproclate, fluvoxamine, etoperidone, escitalopram, monoamine oxidase inhibitors, isocarboxazid, nialamide, phenelzine, tranylcypromine, iproniazide, iproclozide, monoamine oxidase A inhibitors, moclobemide, toloxatone, other antidepressants, such as, for example: oxitriptan, tryptophan, mianserin, nomifensine, trazodone, nefazodone, minaprine, bifemelane, viloxazine, oxaflozane, mirtazapine, medifoxamine, tianeptine, pivagabine, venlafaxine, milnacipran, reboxetine, gepirone, duloxetine, agomelatine, desvenlafaxine, centrally acting sympathomimetics, such as, for example: amfetamine, dexamfetamine, lis dexamfetamine, metamfetamine, methylphenidate, dexmethylphenidate, pemoline, fencamfamin, modafinil, fenozolone, atomoxetine, fenetylline, xanthine derivatives, caffeine, propentofylline, other psychostimulants and nootropics, such as, for example meclofenoxate, pyritinol, piracetam, deanol, fipexide, citicoline, oxiracetam, pirisudanol, linopirdine, nizofenone, aniracetam, acetylcarnitine, idebenone, prolintane, pipradrol, pramiracetam, adrafinil, or vinpocetine.

In another embodiment, suitable active pharmaceutical ingredients can comprise anti-dementia active drug substances, such as, for example: anticholinesterases, tacrine, donepezil, rivastigmine, galantamine, other anti-dementia drugs, memantine, or *ginkgo biloba*.

In another embodiment, suitable active pharmaceutical ingredients can comprise other nervous system active drug substances, such as, for example: parasympathomimetics, anticholinesterases, neostigmine, pyridostigmine, distigmine, ambenonium, choline esters, carbachol, bethanechol, and other parasympathomimetics, such as, for example, pilocarpine, or choline alfoscerate.

Active drug substances used in addictive disorders, such as, for example: nicotine, bupropion, varenicline, disulfiram, calcium carbimide, acamprosate, naltrexone, buprenorphine, methadone, levacetylmethadol, lofexidine, betahistine, cinnarizine, flunarizine, acetylleucine, gangliosides and ganglioside derivatives, tirilazad, riluzole, xaliproden, hydroxybutyric acid, or amifampridine.

In another embodiment, suitable active pharmaceutical ingredients can comprise opium alkaloids and derivatives, such as, for example: ethylmorphine, hydrocodone, codeine, opium alkaloids with morphine, normethadone, noscapine, pholcodine, dextromethorphan, thebacon, dimemorfan, acetyldihydrocodone, benzonatate, benproperine, clobutinol, isoaminile, pentoxyverine, oxolamine, oxeladin, clofedanol, pipazetate, bibenzonium bromide, butamirate, fedrilate, zipeprol, dibunate, droxypropine, prenoxdiazine, dropropizine, cloperastine, meprotixol, piperidione, tipepidine, morclofone, nepinalone, levodropropizine, or dimethoxanate.

In another embodiment, the active pharmaceutical ingredient may be a substance with abuse potential that presents a safety risk. Such active drug substance may include: 1-(1-phenylcyclohexyl)pyrrolidine, 1-(2-phenylethyl)-4-phenyl-4-acetoxypiperidine, 1-[1-(2-thienyl)-cyclohexylpiperidine, 1-[1-(2-thienyl)cyclohexyl]pyrrolidine, 1-methyl-4-phenyl-4-propionoxy-piperidine,
1-phenylcyclohexylamine, 1-piperidinocyclohexanecarbonitrile, 2,5-dimethoxy-4-ethylamphetamine, 2,5-dimethoxyamphetamine, 2C-B-(4-bromo-2,5-dimethoxypenethylamine), 2C-D (2,5-dimethoxy-4-methylphenethylamine), 2C-I (4-iodo-2,5-dimethoxy-phenethylamine), 2C-T-2 (2,5-dimethoxy-4-ethylthiophenethylamine), 2C-T-4 (2,5-dimethoxy-4-isopropyl thiophenethylamine), 2C-T-7 (2,5-dimethoxy-4-(n)-propylthiophenethylamine), 3,4-methylenedioxymethamphetamine, 3,4,5-trimethoxyamphetamine, 3,4-methylenedioxyamphetamine, 3,4-methylenedioxy-N-ethylamphetamine, 3-methylfentanyl, 3-methylthiofentanyl, 4-brorno-2,5-dimethoxyamphetamine, 4-bromo-2,5-dimethoxyphenethylamine, 4-methoxyamphetamine, 4-methyl-2,5-dimethoxyamphetamine, 4-methylaminorex (cis isomer), 5-MeO-DIPT (5-methoxy-N,N-diisopropyltryptamine), 5-MeO-DMT (5-methoxy-N,N-dimethyltryptamine), 5-methoxy-3,4-methylenedioxyamphetamine, acetorphine, acetorphine, acetyl-alpha-methylfentanyl, acetyl-alpha-methylfentanyl, acetyldihydrocodone, acetylmethadol, acetylmethadol, alfentanil, allobarbital, allylprodine, alphacetylmethadol except levo-alphacetylmethadol, alpha-ethyltryptamine, alphameprodine, alphamethadol, alphamethadol, alpha-methylfentanyl, alpha-methylthiofentanyl, alphaprodine, alprazolam, amfepramon, amfetaminil, amineptin, aminorex, amobarbital, amphetamine, dextroamphetamine, amilnitrite (all isomers of the amyl group), anabolic steroids, anileridine, aprobarbital, barbital, barbituric acid derivative, BDB (3,4-methylenedioxyphenyl)-2-butanamine), benzethidin, benzethidine, benzoylecgonine, benzphetamine, benzphetamine, benzylmethylcetone, benzylmorphine, betacetylmethadol, beta-hydroxy-3-methylfentanyl, beta-hydroxyfentanyl, betameprodine, betameprodine, betamethadol, betaprodine, bezitramide, bezitramide, boldenone, brolamfetamine, bromazepam, brotizolam, bufotenine, buprenorphine, butabarbital, butalbital, butobarbital, butorphanol, BZP (A2)(1-benzylpiperazin), camazepam, cannabis, carfentanil, catha edulis, cathine, cathinone, chloral betaine, chloral hydrate, chlordiazepoxide, chlorhexadol, chlorotestosterone (same as clostebol), chlorphentermine, clobazam, clonazepam, clonitazene, clonitazene, clorazepate, clortermine, clostebol, clotiazepam, cloxazolam, coca leaves, cocaine, codeine, codeine and isoquinoline alkaloid, codeine methylbromide, codeine-N-oxide, codoxime, cyclobarbital (hexemal NFN), cyprenorphine, dehydrochlormethyltestosterone, delorazepam, desomorphine, dexamfetamine, dexfenfluramine, dexmethylphenidate, dextromoramide, dextropropoxyphene, diacetylmorphine, diampromide, diazepam, dichloralphenazone, diethylpropion, diethylthiambutene, diethyltryptamine, difenoxin, dihydrocodone, dihydroetorphine, dihydromorphine, dihydrotestosterone, dimenoxadol, dimepheptanol, dimethylthiambutene, dimethyltryptamine, dioxaphetyl butyrate, diphenoxylate, dipipanone, diprenorphine, dronabinol, drostanolone, drotebanol, ecgonine, estazolam, ethchlorvynol, ethinamate, ethyl loflazepate, ethylestrenol, ethylmethylthiambutene, ethylmorphine, ethylmorphine, eticyclidine, etilamfetamine, etonitazene, etorphine, etoxeridine, etryptamine, fencamfamin, fenethylline, fenetylline, fenfluramine, fenproporex, fentanyl, fludiazepam, flunitrazepam, fluoxymesterone, flurazepam, formebolone, fungi and spores of the species psilocybe semilanceata, furethidine, gamma hydroxybutyric acid, glutethimide, halazepam, haloxazolam, heroine, hydrocodone, hydrocodone & isoquinoline alkaloid, hydromorphinol, hydromorphone, hydroxypethidine, ibogaine, isobutyl nitrite, isomethadone, ketamine, ketazolam, ketobemidone, levamfetamine, levo-alphacetylmethadol, levo-methamphetamine, levomethorphan, levomoramide, levophenacylmorphan, levorphanol, lis dexamfetamine, loprazolam, lorazepam, lormetazepam, lysergic acid, lysergic acid amide, lysergic acid diethylamide, marijuana, mazindol, MBDN (N-methyl-1-(3,4-methylenedioxyphenyl)-2-butanamine),
mCPP (1-(3-chlorphenyl)piperazine), mebutamate, mecloqualone, medazepam, mefenorex, MeOPP (1-(4-methoxyphenyl)piperazine), meperidine, meperidine intermediate, meprobamate, mescaline, mesocarb, mesterolone, metamfetamine, metazocine, methadone, methadone intermediate, methamphetamine, methandienone, methandrolone, methandriol, methandrostenolone, methaqualone, methcathinone, methenolone, methohexital, methyldesorphine, methyldihydromorphine, methylphenidate, methylphenobarbital (mephobarbital), methyltestosterone, methyprylone, metopone, mibolerone, midazolam, modafinil, moramide-intermediate, morpheridine, morphine, morphine methylbromide, morphine methylsulfonate, morphine-N-oxide, myrophine, N,N-dimethylamphetamine, nabilone, nalorphine, nandrolone, N-ethyl-1-phenylcyclohexylamine, N-ethyl-3-piperidyl benzilate, N-ethylamphetamine, N-hydroxy-3,4-methylenedioxyamphetamine, nicocodeine, nicocodine, nicodicodine, nicomorphine, nimetazepam, nitrazepam, N-methyl-3-piperidyl benzilate, noracymethadol, norcodeine, nordiazepam, norethandrolone, norlevorphanol, normethadone, normorphine, norpipanone, norpipanone, opium, oxandrolone, oxazepam, oxazolam, oxycodone, oxymesterone, oxymetholone, oxymorphone, para-fluorofentanyl, parahexyl, paraldehyde, pemoline, pentazocine, pentobarbital, petrichloral, peyote, phenadoxone, phenampromide, phenazocine, phencyclidine, phendimetrazine, phenmetrazine, phenobarbital, phenomorphan, phenoperidine, phentermine, phenylacetone, pholcodine, piminodine, pinazepam, pipradrole, piritramide, PMMA (paramethyxymethyl amphetamine), prazepam, proheptazine, properidine, propiram, psilocybine, psilocine, pyrovalerone, quazepam, racemethorphane, racemoramide, racemorphane, remifentanil, salvia divinorum, salvinorin A, secobarbital, secobarbital, sibutramine, SPA, stanolone, stanozolol, sufentanil, sulfondiethylmethane, sulfonethylmethane, sulfonmethane, talbutal, temazepam, tenamfetamine, testolactone, testosterone, tetrahydrocannabinols, tetrazepam, TFMPP (1-(3-triflourmethylphenyl)piperazine), thebacon, thebaine, thiamylal, thiofentanyl, thiopental, tiletamine and zolazepam in combination, tilidine, trenbolone, triazolam, trimeperidine, vinbarbital, zaleplon, zipeprol, zolpidem, or zopiclone.

Other suitable examples of active drug substances suitable for use in the pharmaceutical compositions described herein include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodone, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narcine, nicomorphine, norlevorphanol, normethadone, nalorphine, normorphine, norpipanone, opium, oxycodone, oxycodeine, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, thebaine, levo-alphacetylmethadol (LAAM), remifentanil, carfentanyl, ohmefentanyl, MPPP, prodine, PEPAP, levomethorphan, etorphine, lefetamine, loperamide, diphenoxylate, or pethidine.

Other examples of active drug substances suitable for use in the pharmaceutical compositions described herein include anabolic steroids, cannabis, cocaine, or diazepam.

In another embodiment, the active drug substance comprises the therapeutic classes including non-steroidal antiinflammatory substances or antirheumatic active drug substances. In other embodiments, the active drug substance comprises analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alfa-adrenergic, serotonin, H3 antagonists used for ADHD or nootropics agents used in addictive disorders.

In other embodiments, the active drug substance comprises therapeutic classes including anaesthetics, centrally acting analgesics, sedative-hypnotics, anxiolytics, appetite suppressants, decongestants, antitussives, antihistamines, antiemetics, antidiarrheals, and drugs used to treat narcolepsy, or attention deficit hyperactivity disorder.

In another embodiment, the active drug substance is associated with abuse syndromes and the active drug substance may, for example, be selected from opioids, CNS depressants, CNS stimulants, cannabinoids, nicotine-like compounds, glutamate antagonists, or N-methyl-D-aspartate (NMDA) antagonists.

In another embodiment, the active drug substance is an analgesic. Examples of analgesics suitable for use in the pharmaceutical compositions described herein include, for example, opioids, natural opium alkaloids, morphine, opium, hydromorphone, nicomorphine, oxycodone, dihydrocodone, diamorphine, tapentadol, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics such as, for example, rimazolium, glafenine, floctafenine, viminol, nefopam, flupirtine, or ziconotide.

In another embodiment, the active drug substance is an opioid. Where an opioid is included as an active drug substance, the opioid may comprise naturally occurring opioids, synthetic opioids, or semisynthetic opioids.

In other embodiment, the active drug substance comprises amfetamine, dexamfetamine, lisdexamfetamine, metamfetamine, methylphenidate, dexmethylphenidate, or combinations thereof.

In another embodiment, the pharmaceutical compositions disclosed herein includes an opioid, the opioid is selected from buprenorphine, codeine, dextromoramide, dihydrocodone, fentanyl, hydrocodone, hydromorphone, morphine, pentazocine, oxycodeine, oxycodone, oxymorphone, norhydrocodone, noroxycodone, morphine-6-glucuronode, tramadol, tapentadol, or dihydromorphine.

Where an opioid is used as an active drug substance, the opioid may be present in any of its crystalline, polymorphous, semi-crystalline, and amorphous or polyamorphous forms. Furthermore, in another embodiment, an opioid used as an active drug substance may be present in one or more forms selected from its crystalline, polymorphous, semicrystalline, or amorphous or polyamorphous forms.

Some embodiments of the pharmaceutical compositions disclosed herein include an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts thereof, including oxycodone hydrochloride, hydrocodone bitartrate, hydromorphone hydrochloride or morphine sulphate pentahydrate.

In other embodiments, the pharmaceutical compositions as described herein are suitable for use for water soluble as well as slightly soluble or insoluble active drug substances.

In another embodiment, all of the above mentioned active drug substances may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the pharmaceutical compositions described herein may comprise pharmaceutically acceptable salts of any of the above mentioned active drug substances.

In another embodiment, the active pharmaceutical ingredient is hydrocodone or oxycodone or a pharmaceutically acceptable salt form of either hydrocodone or oxycodone. Pharmaceutically acceptable salts forms are those formed by contacting hydrocodone or oxycodone free base with a suitable acid in a suitable solvent under suitable conditions that will form a form of hydrocodone or oxycodone acid addition salt. Suitable acids include hydrochloric acid, camphorsulfonic acid, hydrobromic acid, sulfuric acid, methanesulfonic acid, formic acid, acetic acid, oxalic acid, succinic acid, tartaric acid, mandelic acid, malic acid, salicylic acid, fumaric acid, lactic acid, citric acid, glutamic acid, and/or aspartic acid.

The term "pharmaceutically acceptable salts" of an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc. In another embodiment, pharmaceutically acceptable opioid salts can comprise sulphate salts, hydrochloride salts, and bitartrate salts.

In another embodiment, the active pharmaceutical ingredient may be in any of its crystalline, polymorphous, semicrystalline, amorphous or polyamorphous forms or mixtures thereof.

The concentration of the active drug substance in the pharmaceutical composition for use according to the disclosure depends on the specific active drug substance, the disease to be treated, the condition of the patient, the age, and gender of the patient, etc. The above-mentioned active drug substances may be known active drug substances and a person skilled in the art will be able to find information as to the dosage of each active drug substance and, accordingly, will know how to determine the amount of each active drug substance in the pharmaceutical composition.

The active pharmaceutical ingredient may be a new chemical entity for which the amount of information is limited. In such cases, the dosage has to be evaluated based on available preclinical and/or clinical data.

In some embodiments described herein, the pharmaceutical composition comprises soft capsule shell comprising a matrix comprising an active pharmaceutical ingredient.

In one embodiment described herein, the soft capsule shell has the composition of Table 2, including all possible iterations of the specified ranges that provide 100% for the total weight percentage, including or excluding the optional colorings, flavorings, or excipients.

TABLE 2

Exemplary Soft Gelatin Capsule Composition

| Component | Exemplary Component | Weight Percentage (%) |
| --- | --- | --- |
| Film-forming polymer | Gelatin | 20-36 (Gelatin) |
| Plasticizer | Glycerol | 10-30 |
| Solvent | Water | 20-70 |
| Opacifier (optional) | Titanium dioxide | 0.5-1.5 |
| Coloring agent (optional) | Various | 0.05-0.1 |
| TOTAL | | 100% |

Film-former polymers that are useful for creating soft capsules are gelatin, hydroxypropylmethylcellulose (HPMC) or carrageenan (e.g., iota carrageenan and kappa carrageenan). In one aspect of the enteric soft capsule shell described herein, the film-forming polymer is gelatin. In another aspect of the enteric soft capsule shell described herein, the film-forming polymer is carrageenan.

Plasticizers that are useful for creating soft capsules as described herein are glycerol, sorbitol, polyethylene glycols, or combinations thereof. The weight ratio between the film-forming polymer, plasticizer, and solvent is adjusted so that the gel mass is flowable and not too viscous, and can be made into soft capsules using rotary die encapsulation methods.

In one embodiment, the soft capsule shell has the exemplary composition shown in Table 3.

TABLE 3

Exemplary Soft Gelatin Capsule Shell Composition

| Component | Percent weight (%) |
| --- | --- |
| Gelatin | 43 |
| Glycerol | 20 |
| Titanium dioxide (optional) | 0.7 |
| Coloring agent (optional) | 0.1 |
| Water | 36.2 |
| TOTAL | 100% |
| Final pH | ~4-7 |
| Ratio total plasticizer to gelatin | 20:43 (0.46:1) |
| Water content in dried soft capsule shell: | 8-15% |

In one embodiment described herein, the soft capsule comprises about 43% of at least one film-forming polymer; about 20% of at least one plasticizer; about 36% water; optionally, about 0.7% titanium dioxide; and optionally, about 0.1% of at least one coloring agent.

In one embodiment described herein, the enteric soft capsule described herein comprises a composition of about 3% to about 10% film forming polymer (e.g., a composition of carrageenan); about 10% to about 30% filler; about 10% to about 30% plasticizer; and about 30% to about 70% solvent.

In one embodiment, the weight percentage range of film-forming polymer of the soft capsule described herein is about 35% to about 45%, including all integers within the specified range. In one aspect, the film-forming polymer weight percentage is about 38%. In another aspect, the film-forming 1 polymer weight percentage is about 42%. In another aspect, the film-forming polymer weight percentage is about 44%.

In one embodiment, the weight percentage range of film-forming polymer of the soft capsule described herein is about 3% to about 15%, including all integers within the specified range. In one aspect, the film-forming polymer weight percentage is about 3%. In one aspect, the film-forming polymer weight percentage is about 5%. In one aspect, the film-forming polymer weight percentage is about 7%. In one aspect, the film-forming polymer weight percentage is about 10%. In one aspect, the film-forming polymer weight percentage is about 12%.

In one embodiment, the weight percentage range of plasticizer is about 15% to about 22%, including all iterations of integers with the specified range. In one aspect, the plasticizer weight percentage is about 17%. In another aspect, the plasticizer weight percentage is about 18.5%. In another aspect, the plasticizer weight percentage is about 20%.

In one embodiment, the weight percentage ratio range of plasticizer to film-forming polymer is about 0.33:1 to about 0.56:1, including all iterations of iterations of ratios with the specified range. In one embodiment, the weight percentage ratio range of plasticizer to film-forming polymer is about 0.38:1. In one embodiment, the weight percentage ratio range of plasticizer to film-forming polymer is about 0.42:1. In one embodiment, the weight percentage ratio range of plasticizer to film-forming polymer is about 0.46:1. In one embodiment, the weight percentage ratio range of plasticizer to film-forming polymer is about 0.52:1.

In one aspect, soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing soft capsules comprising the pharmaceutical composition as described herein. The process includes preparing a gel mass composition comprising a film-forming, water-soluble polymer, an appropriate plasticizer, and solvent; casting the gel mass into films or ribbons using heat-controlled drums or surfaces; and manufacturing a soft capsule comprising a matrix fill using rotary die technology. The thickness of the films or ribbons that form the soft capsule shell is from about 0.010 inches (≈0.254 mm) to about 0.050 inches (≈1.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈1.02 mm), or about 0.05 in (≈1.27 mm). In one embodiment, the thickness is about 0.02 inches (≈0.508 mm) to about 0.040 inches (≈1.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

In one embodiment described herein, the soft capsule shell described herein, encapsulates a matrix fill as described herein. In another embodiment described herein, the soft capsule shell and encapsulated matrix fill comprises an outer dimension from about 2 oval to about 30 oval including all iterations of capsule size within the specified range (e.g., 2 oval, 3 oval, 4 oval, 5 oval, 6 oval, 7 oval, 8 oval, 10 oval, 12 oval, 16 oval, 20, or 30 oval). In another embodiment described herein, the soft capsule shell and encapsulated matrix fill comprises an outer dimension from about 2 round to about 28 round including all iterations of capsule size within the specified range (e.g., 2 round, 3 round, 4 round, 5 round, 6 round, 7 round, 8 round, 10 round, 12 round, 16 round, 20 round or 28 round). In another embodiment described herein, the soft capsule shell and encapsulated matrix fill comprises an outer dimension from about 2 oblong to about 22 oblong including all iterations of capsule size within the specified range (e.g., 2 oblong, 3 oblong, 4 oblong, 5 oblong, 6 oblong, 7 oblong, 8 oblong, 10 oblong, 11, oblong, 12 oblong, 14 oblong, 16 oblong, 20 oblong, or 22 oblong). Dimension specifications of soft capsules and tablets are known to those skilled in the art. *See Remington's Essentials of Pharmaceutics*, Pharmaceutical Press Publishing Company, London, UK, 1$^{st}$ Edition, 2013, which is incorporated by reference herein for such teachings.

In another embodiment described herein, the pharmaceutical composition comprises an enteric soft capsule shell comprising a matrix fill comprising an active pharmaceutical ingredient. Enteric soft capsules are described in International Patent Application Publication No. WO 2004/030658; U.S. Patent Application Publication No. US 2006/0165778; and U.S. Pat. No. 8,685,445, each of which is incorporated by reference herein for such teachings. The enteric soft capsule shell may comprise one or more film forming polymers, one or more enteric acid-insoluble polymers, one or more plasticizers, one or more alkali-neutralizing agents, one or more solvents, optionally one or more colorants, and optionally one or more flavorings or other conventionally accepted pharmaceutical excipients or additives.

In another embodiment, the capsule shell is a hard capsule shell. In one aspect, the hard capsule shell may comprise the abuse deterrent matrices described herein. Any hard capsule shell, for example hard capsule shells comprising gelatin, HPMC, or pullulan, including hard capsule shells exhibiting enteric properties, maybe used with the abuse deterrent matrix fills described herein. Hard capsule shells are known in the art and are described by Kathpalia et al., *J. Adv. Pharm. Edu. & Res.* 4(2): 165-177 (2014), which is incorporated by reference herein for its specific teachings thereof.

Additional pharmaceutical excipients useful in the abuse deterrent pharmaceutical compositions include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Alkalizing agents (ammonia solution, ammonium carbonate, diethanolamine, diisopropanolamine, potassium hydroxide, sodium bicarbonate, sodium borate, sodium carbonate, sodium hydroxide, trolamine); Antifoaming agents (dimethicone, simethicone); Antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celluloses, hydroxyalkyl, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (Bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in the abuse deterrent pharmaceutical compositions as described herein.

One embodiment described herein, is a pharmaceutical composition comprising a matrix fill formulation comprising any of the formulations shown in the Tables or Examples described herein. Any of the components of the formulations shown in the Tables or Examples can be increased, decreased, combined, recombined, switched, or removed to provide for a formulation comprising about 100% by weight.

Another embodiment described herein is a method for preparing abuse deterrent pharmaceutical compositions comprising the abuse deterrent controlled release matrix described herein comprising (a) mixing one or more optional viscosity modifiers, one or more release modifiers, one or more optional antioxidants, and one or more surfactants in one or more flowability enhancers to form a first mixture; (b) adding one or more active pharmaceutical ingredient to the first mixture to form a matrix fill mixture; (c) filling the matrix fill mixture into capsule shells using standard rotary die encapsulation techniques; and (d) annealing the capsules at an elevated temperature for a period of time. In one aspect, the flowability enhancer is heated to a first elevated temperature prior to mixing the one or more viscosity modifiers, release modifiers, and one or more surfactants. In another aspect, the flowability enhancer or mixture comprising the flowability enhancer is cooled to a second temperature. In another aspect, the flowability enhancer or mixture comprising the flowability enhancer is cooled to a third temperature. In another aspect, the one or more viscosity modifiers are added to the heated flowability enhancer before adding the one or more release modifiers. In another aspect, the heated mixture is cooled to a second elevated temperature prior to adding the active pharmaceutical ingredient, the one or more release modifiers, and the one or more surfactants. In another aspect, the active pharmaceutical ingredient is added prior to adding the one or more release modifiers. In another aspect, one or more antioxidants are added prior to adding the one or more release modifiers.

In another embodiment, the method for preparing the abuse deterrent pharmaceutical compositions described herein comprise (a) heating one or more flowability enhancers to a first temperature, (b) adding a first viscosity modifier to the heated flowability enhancer; (c) cooling the mixture of step b) to a second temperature; (d) adding one or more antioxidants to the mixture of step (c); (e) cooling the mixture of step (d) to a third temperature; (f) adding one or more release modifiers, one or more surfactants, and the active pharmaceutical ingredient to the cooled mixture of step (e); and (g) filling the matrix fill mixture into capsule shells using standard rotary die encapsulation techniques; and (h) annealing the capsules at an elevated temperature for a period of time.

In one embodiment, the methods for preparing the abuse deterrent pharmaceutical compositions described herein comprise heating the flowability enhancer or a mixture comprising the flowability enhancer to a first temperature. In one aspect, the first temperature is about 40° C. to about 170° C., including each integer within the specified range. In another aspect, the first temperature is about 120° C. to about 170° C., including each integer within the specified range. In another aspect, the first temperature is about 40° C. to about 90° C., including each integer within the specified range. In another aspect, the first temperature is about 40° C. to about 90° C., including each integer within the specified range. In another aspect, the first temperature is about 40° C., about 45° C., about 50° C., about 55° C., about 60° C., about 65° C., about 70° C., about 75° C., about 80° C., about 90° C., about 100° C., about 110° C., about 120° C., about 130° C., about 140° C., about 150° C., about 160° C., or about 170° C.

In another embodiment, the methods for preparing the abuse deterrent pharmaceutical compositions described herein comprise cooling the flowability enhancer or a mixture comprising the flowability enhancer to a second temperature. In one aspect, the second temperature is about 25° C. to about 100° C., including each integer within the specified range. In another aspect, the second temperature is about 25° C. to about 50° C., including each integer within the specified range. In another aspect, the second temperature is about 40° C. to about 90° C., including each integer within the specified range. In another aspect, the second temperature is about 40° C. to about 90° C., including each integer within the specified range. In another aspect, the second temperature is about 25° C., about 30° C., about 35° C., about 40° C., about 45° C., about 50° C., about 55° C., about 60° C., about 65° C., about 70° C., about 75° C., about 80° C., about 90° C., or about 100° C.

In another embodiment, the methods for preparing the abuse deterrent pharmaceutical compositions described herein comprise cooling the flowability enhancer or a mixture comprising the flowability enhancer to a third temperature. In one aspect, the third temperature is about 25° C. to about 100° C., including each integer within the specified range. In another aspect, the third temperature is about 25° C. to about 50° C., including each integer within the specified range. In another aspect, the third temperature is about 40° C. to about 90° C., including each integer within the specified range. In another aspect, the third temperature is about 40° C. to about 90° C., including each integer within the specified range. In another aspect, the third temperature is about 25° C., about 30° C., about 35° C., about 40° C., about 45° C., about 50° C., about 55° C., about 60° C., about 65° C., about 70° C., about 75° C., about 80° C., about 90° C., or about 100° C.

In another embodiment, the methods for preparing the abuse deterrent pharmaceutical compositions described herein comprise annealing the pharmaceutical composition comprising a soft or capsule shell and a matrix fill as described herein at specified temperature for a period of time. In one aspect, the temperature ranges from about 45° C. to about 120° C., including each integer within the specified range. In another aspect, the temperature ranges from about 55° C. to about 85° C., including each integer within the specified range. In another aspect, the temperature is about 45° C., about 50° C., about 55° C., about 60° C., about 65° C., about 70° C., about 75° C., about 80° C., about 90° C., about 100° C., about 110° C., or about 120° C. In another aspect, the annealing time ranges from about 10 minutes to about 160 minutes, including each integer within the specified range. In another aspect, the annealing time ranges from about 1 minute to about 80 minutes, including each integer within the specified range. In another aspect, the annealing time ranges from about 40 minutes to about 80 minutes, including each integer within the specified range. In another aspect, the annealing time is about 1 min, about 3 min, about 6 min, about 9 min, about 12 min, about 15 min, about 20 min, about 25 min, about 30 min, about 35 min, about 40 min, about 45 min, about 50 min, about 55 min, about 60 min, about 70 min, about 80 min, about 90 min, about 100 min, about 110 min, about 120 min, about 130 min, about 140 min, about 150 min, or about 160 min.

In another embodiment, the abuse deterrent pharmaceutical composition described herein provides a dosage of an active pharmaceutical ingredient described herein for administration to a subject. The dosage form can be administered, for example, to a subject, or a subject in need thereof. In one aspect, the subject is a mammal, or a mammal in need thereof. In one aspect, the subject is a human, or human in need thereof. In one aspect, the human or human in need thereof is a medical patient. In one aspect, the human subject is a child (~0-9 years old) or an adolescent (~10-17 years old). In one aspect, the subject is from 0 to 9 years of age. In another aspect, the human subject is from 10 to 17 years of age. In another aspect, the human subject is over 17 years of age. In another aspect, the human subject is an adult (≥18 years of age).

In one embodiment, the dosage may be administered to a human in need of management of moderate to severe chronic pain and neuropathic pain associated with diabetic peripheral neuropathy (DPN), when a continuous, persistent (around-the-clock) opioid analgesic is needed for an extended period of time.

The dosage form can be administered, for example, 1×, 2×, 3×, 4×, 5×, 6×, or even more times per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, 1 year, 2, years, 3 years, 4 years, 5 years, over 5 years, a decade, multiple decades, or even longer. One or more dosage forms can be administered at a regular interval until the subject or subject in need thereof, does not require treatment, prophylaxis, or amelioration of any disease or condition, including but not limited to, pain.

In one embodiment, the pharmaceutical composition described herein is administered in multiple dosages simultaneously. For example, two or more identical dosages are administered at one time. In another embodiment, two or more different dosages are administered at one time. Such dual or different simultaneous doses can be used to provide an effective amount of the pharmaceutical composition to a subject in need thereof.

In one embodiment, the abuse deterrent oral composition described herein, comprises one or more active pharmaceutical ingredients in an amount of about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, or even more.

In another embodiment, the abuse deterrent oral composition described herein, comprises one or more active pharmaceutical ingredients in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, about 240 mg to about 250 mg; about 250 mg to about 500 mg, about 260 mg to about 500 mg, about 270 mg to about 500 mg, about 280 mg to about 500 mg, about 290 mg to about 500 mg, about 300 mg to about 500 mg, about 310 mg to about 500 mg, about 320 mg to about 500 mg, about 330 mg to about 500 mg, about 340 mg to about 500 mg, about 350 mg to about 500 mg, about 360 mg to about 500 mg, about 370 mg to about 500 mg, about 380 mg to about 500 mg, about 390 mg to about 500 mg, about 400 mg to about 500 mg, about 410 mg to about 500 mg, about 420 mg to about 500 mg, about 430 mg to about 500 mg, about 440 mg to about 500 mg, about 450 mg to about 500 mg, about 460 mg to about 500 mg, about 470 mg to about 500 mg, about 480 mg to about 500 mg, or about 490 mg to about 500 mg.

In one embodiment described herein, the abuse deterrent oral composition described herein may comprise an active pharmaceutical ingredient load (e.g., a drug load of one or more active pharmaceutical ingredients) of about 1% to about 90%, including each integer within the specified range. In one embodiment, the drug load can comprise about 1%, about 2%, about 2.5%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or even higher. In one aspect, the drug load is about 5%. In one aspect, the drug load is about 10%. In one aspect, the drug load is about 20%. In one aspect, the drug load is about 25%. In one aspect, the drug load is about 30%. In one aspect, the drug load is about 35%. In one aspect, the drug load is about 40%. In one aspect, the drug load is about 50%. In one aspect, the drug load is about 60%. In one aspect, the drug load is about 28%. In one aspect, the drug load is about 32%. In one aspect, the drug load is about 44%. In one embodiment, the drug load is about 48%.

In one embodiment, the active pharmaceutical ingredient is oxycodone, hydrocodone or codeine, or a salt, ether, ester, variant, or derivative thereof. In one embodiment, the active pharmaceutical ingredient is oxycodone. In another embodiment, the active pharmaceutical ingredient is hydrocodone. See Prescribing Information for OxyContin® ER 04/2014 (Purdue Pharma LP; available at: www.purduepharma.com), Zohydro® ER 01/2015 (Zogenix® Inc.; available at: www.zogenix.com), or Hysingla® ER 02/2015 (Purdue Pharma LP; available at: www.hysinglaer.com), which are incorporated by reference herein for such teachings.

In another embodiment, the active pharmaceutical ingredient may comprise oxycodone, hydrocodone, or codeine and an additional active pharmaceutical ingredient. In one aspect, the additional active pharmaceutical ingredient prevents opioid abuse when an excess of opioid is used. In another aspect, the additional active pharmaceutical ingredient reduces or prevents opioid induced side effects.

In one embodiment, the abuse deterrent oral composition described herein comprises a dose of hydrocodone. In one aspect, the dose of hydrocodone is about 5 mg. In one aspect, the dose of hydrocodone is about 10 mg. In one aspect, the dose of hydrocodone is about 20 mg. In another aspect, the dose of hydrocodone is about 30 mg. In another aspect, the dose of hydrocodone is about 40 mg. In another aspect, the dose of hydrocodone is about 50 mg. In another aspect, the dose of hydrocodone is about 60 mg. In another aspect, the dose of hydrocodone is about 70 mg. In another aspect, the dose of hydrocodone is about 80 mg. In another aspect, the dose of hydrocodone is about 90 mg. In another aspect, the dose of hydrocodone is about 100 mg. In another aspect, the dose of hydrocodone is about 120 mg. In another aspect, the dose of hydrocodone is about 140 mg. In another aspect, the dose of hydrocodone is about 160 mg. In another aspect, the dose of hydrocodone is about 180 mg. In another aspect, the dose of hydrocodone is about 200 mg.

In one embodiment, the abuse deterrent oral composition described herein comprises a dose of oxycodone. In one aspect, the dose of oxycodone is about 5 mg. In another aspect, the dose of oxycodone is about 10 mg. In another aspect, the dose of oxycodone is about 15 mg. In another aspect, the dose of oxycodone is about 20 mg. In another aspect, the dose of oxycodone is about 30 mg. In another aspect, the dose of oxycodone is about 40 mg. In another aspect, the dose of oxycodone is about 50 mg. In another aspect, the dose of oxycodone is about 60 mg. In another aspect, the dose of oxycodone is about 70 mg. In another aspect, the dose of oxycodone is about 80 mg. In another aspect, the dose of oxycodone is about 100 mg. In another aspect, the dose of oxycodone is about 120 mg. In another aspect, the dose of oxycodone is about 140 mg. In another aspect, the dose of oxycodone is about 160 mg. In another aspect, the dose of oxycodone is about 180 mg. In another aspect, the dose of oxycodone is about 200 mg.

In another embodiment, the total dosage of oxycodone or hydrocodone administered in a 24-hour period is about 20 mg to about 600 mg per 24-hour period. In one aspect, the total dosage of oxycodone or hydrocodone administered in a 24-hour period is about 50 mg to about 250 mg per 24-hour period. The dosage can contain a total amount of oxycodone or hydrocodone effective for treatment, amelioration, prophylaxis, or reducing the onset of or symptoms of pain.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of hydrocodone is 10 mg to about 40 mg. In one aspect, an initial dose of about 10 mg to about 40 mg is suitable for a subject that not tolerant of an opioid. In one aspect, the initial dose is about 10 mg of hydrocodone. In another aspect, the initial dose is about 20 mg of hydrocodone. In another aspect, the initial dose is about 20 mg of hydrocodone. In another aspect, the initial dose is about 30 mg of hydrocodone. In another aspect, the initial dose is about 40 mg of hydrocodone. In another aspect, the dose of hydrocodone may be maintained and given every 8 to 12 hours. In another aspect, the dose of hydrocodone may be increased by about 10 mg to about 20 mg every 8 hrs to 12 hrs until relief of a painful condition or the perception of pain occurs.

In another embodiment, the initial dosage of hydrocodone is 40 mg to about 80 mg. In one aspect, an initial dose of about 40 mg to about 80 mg is suitable for a subject that has an opioid tolerant phenotype. In one aspect, the initial dose is about 40 mg of hydrocodone. In another aspect, the initial dose is about 50 mg of hydrocodone. In another aspect, the initial dose is about 60 mg of hydrocodone. In another aspect, the initial dose is about 70 mg of hydrocodone. In another aspect, the initial dose is about 80 mg of hydrocodone. In another aspect, the dose of hydrocodone may be maintained and given every 8 to 12 hours. In another aspect, the dose of hydrocodone may be increased by about 10 mg to about 20 mg every 8 hrs to 12 hrs until relief of a painful condition or the perception of pain occurs.

In one embodiment, the recommended dosage is based upon the condition of the subject in need thereof. The subject can comprise a human or mammal in need thereof. In one aspect, the need is defined as a painful condition or perception of pain. In one embodiment, the initial dosage of oxycodone is 10 mg to about 40 mg. In one aspect, an initial dose of about 10 mg to about 40 mg is suitable for a subject that not tolerant of an opioid and a dose. In one aspect, the initial dose is about 10 mg of oxycodone. In another aspect, the initial dose is about 20 mg of oxycodone. In another aspect, the initial dose is about 20 mg of oxycodone. In another aspect, the initial dose is about 30 mg of oxycodone. In another aspect, the initial dose is about 40 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until relief of a painful condition or the perception of pain occurs.

In another embodiment, the initial dosage of oxycodone is 40 mg to about 160 mg. In one aspect, an initial dose of about 40 mg to about 80 mg is suitable for a subject that has an opioid tolerant phenotype. In one aspect, the initial dose is about 40 mg of oxycodone. In another aspect, the initial dose is about 50 mg of oxycodone. In another aspect, the initial dose is about 60 mg of oxycodone. In another aspect, the initial dose is about 70 mg of oxycodone. In another aspect, the initial dose is about 80 mg of oxycodone. In another aspect, the initial dose is about 100 mg of oxycodone. In another aspect, the initial dose is about 120 mg of oxycodone. In another aspect, the initial dose is about 140 mg of oxycodone. In another aspect, the initial dose is about 160 mg of oxycodone. In another aspect, the dose of oxycodone may be maintained and given every 8 to 12 hours. In another aspect, the dose of oxycodone may be increased by about 10 mg to about 20 mg every 8 hrs to 12 hrs until relief of a painful condition or the perception of pain occurs.

Additionally, the abuse deterrent pharmaceutical compositions described herein may be useful for the treatment of pain stemming from, including but not limited to, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica, or granuloma annulare.

Another embodiment described herein is an abuse deterrent pharmaceutical composition as described herein for administration to a subject having pain, comprising a therapeutically effective amount of one or more active pharmaceutical ingredients exhibiting an in vitro dissolution rate at pH 6.8 comprising about 10% to about 95% dissolution after about 60 minutes to about 480 minutes including each integer within the specified ranges of dissolution and time. In one aspect, the in vitro dissolution rate at pH 1.2 is about 12% after about 60 min, about 20% after about 120 min, about 30% after about 240 min, and about 50% after about 480 min.

In another embodiment, the abuse deterrent pharmaceutical composition comprising an abuse deterrent matrix as described herein reduces the dissolution and extraction of an active pharmaceutical ingredient. Suitable non-limiting examples of extraction methods comprise incubating the abuse deterrent pharmaceutical composition in boiling conditions, in aqueous solutions of alcohol, and in distilled water. These methods may be used in conjunction with additional means of agitating, for example, with paddles, dipping, vigourous shaking, physical manipulations, and the like.

In another embodiment, the abuse deterrent pharmaceutical composition as described herein has an in vitro dissolution rate under boiling conditions in an aqueous media (e.g., a temperature of about 90° C. to about 120° C.) is less than about 10% to about 50% after about 10 minutes to about 120 minutes, including each integer within the specified ranges of dissolution and time. In one aspect, the in vitro dissolution rate of the controlled release pharmaceutical composition under boiling conditions in an aqueous media is less than about 10% after about 5 minutes. In another aspect, the in vitro dissolution rate of the controlled release pharmaceutical composition under boiling conditions in an aqueous media is less than about 20% after about 10 minutes. In another aspect, the in vitro dissolution rate of the controlled release pharmaceutical composition under boiling conditions in an aqueous media is less than about 20% after about 20 minutes. In another aspect, the in vitro dissolution rate of the controlled release pharmaceutical composition under boiling conditions in an aqueous media is less than about 30% after about 30 minutes. In another aspect, the in vitro dissolution rate of the controlled release pharmaceutical composition under boiling conditions in an aqueous media is less than about 40% after about 45 minutes. In another aspect, the in vitro dissolution rate of the controlled release pharmaceutical composition under boiling conditions in an aqueous media is less than about 40% after about 80 minutes. In another aspect, the in vitro dissolution rate of the controlled release pharmaceutical composition under boiling conditions in an aqueous media is less than about 40% after about 120 minutes. In another aspect, the in vitro dissolution rate of the controlled release pharmaceutical composition under boiling conditions in an aqueous media is less than about 50% after about 120 minutes.

In another embodiment, the abuse deterrent controlled release pharmaceutical composition as described herein has an in vitro dissolution rate in an aqueous alcohol solution (e.g., an aqueous solution of ethanol of 80%) of less than about 20% to about 50% after about 30 minutes to about 360 minutes, including each integer within the specified ranges of dissolution and time. In one aspect, the in vitro dissolution rate of the controlled release pharmaceutical composition in an aqueous alcohol solution is less than about 10% after about 30 minutes. In another aspect, the in vitro dissolution rate of the controlled release pharmaceutical composition in an aqueous alcohol solution is less than about 20% after about 60 minutes. In another aspect, the in vitro dissolution rate of the controlled release pharmaceutical composition in an aqueous alcohol solution is less than about 30% after about 90 minutes. In another aspect, the in vitro dissolution rate of the controlled release pharmaceutical composition in an aqueous alcohol solution is less than about 40% after about 120 minutes. In another aspect, the in vitro dissolution rate of the controlled release pharmaceutical composition in an aqueous alcohol solution is less than about 40% after about 180 minutes. In another aspect, the in vitro dissolution rate of the controlled release pharmaceutical composition in an aqueous alcohol solution is less than about 50% after about 360 minutes.

Another embodiment described herein is an abuse deterrent pharmaceutical composition as described herein comprising a therapeutically effective amount of one or more active pharmaceutical ingredients for administration to a subject having pain, exhibiting an in vitro dissolution rate at pH 6.8 of about 10% to about 95% after about 60 minutes to about 480 minutes, an in vitro dissolution rate under boiling conditions less than about 20% to about 30% after about 10 minutes to about 60 minutes, and an in vitro dissolution rate in an aqueous alcohol solution of less than about 20% to about 50% after about 30 minutes to about 360 minutes.

Another embodiment described herein is an abuse deterrent pharmaceutical composition as described herein comprising a therapeutically effective amount of one or more active pharmaceutical ingredients for administration to a subject having pain, exhibiting an in vitro dissolution rate as described herein in any one of FIGS. 2-12.

Another embodiment described herein is a method for orally administering a dosage form of an abuse deterrent pharmaceutical composition comprising an active pharmaceutical ingredient described herein for the treatment, amelioration, prophylaxis, or reducing the onset of or symptoms of pain.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, exhibiting an in vitro dissolution rate at pH 6.8 of about 10% to about 95% after about 60 minutes to about 480 minutes, an in vitro dissolution rate under boiling conditions less than about 20% to about 30% after about 10 minutes to about 60 minutes, and an in vitro dissolution rate in an aqueous alcohol solution of less than about 20% to about 50% after about 30 minutes to about 360 minutes.

Another embodiment described herein is a method for treating, retarding the progression of, delaying the onset of, prophylaxis of, amelioration of, or reducing the symptoms of pain, comprising administering to a subject in need thereof an oral pharmaceutical composition as described herein comprising a therapeutically effective amount of one or more active pharmaceutical ingredients for administration to a subject having pain, exhibiting an in vitro dissolution rate as described herein in any one of FIGS. 2-12.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibit a mean plasma oxycodone $C_{max}$ of about 10 ng/mL to about 150 ng/mL, including each integer within the specified range. In one aspect, the composition is provided in a dosage form containing a total amount of about 10 mg of oxycodone, wherein subjects administered a single dosage exhibit a mean plasma oxycodone $C_{max}$ of about 10 ng/mL. In another aspect, the composition is provided in a dosage form containing a total amount of about 20 mg of oxycodone, wherein subjects administered a single dosage exhibit a mean plasma oxycodone $C_{max}$ of about 20 ng/mL. In another aspect, the composition is provided in a dosage form containing a total amount of about 40 mg of oxycodone, wherein subjects administered a single dosage exhibit a mean plasma oxycodone $C_{max}$ of about 40 ng/mL. In another aspect, the composition is provided in a dosage form containing a total amount of about 80 mg of oxycodone, wherein subjects administered a single dosage exhibit a mean plasma oxycodone $C_{max}$ of about 100 ng/mL.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibit a mean plasma oxycodone $AUC_{0 \to \infty}$ of about 100 h·mg/L to about 1000 h·mg/L, including each integer within the specified range. In one aspect, the composition is provided in a dosage form containing a total amount of about 10 mg of oxycodone, wherein subjects administered a single dosage exhibit a mean plasma oxycodone $AUC_{0 \to \infty}$ of about 100 h·mg/L. In another aspect, the composition is provided in a dosage form containing a total amount of about 20 mg of oxycodone, wherein subjects administered a single dosage exhibit a mean plasma oxycodone $AUC_{0 \to \infty}$ of about 200 h·mg/L. In another aspect, the composition is provided in a dosage form containing a total amount of about 40 mg of oxycodone, wherein subjects administered a single dosage exhibit a mean plasma oxycodone $AUC_{0 \to \infty}$ of about 400 h·mg/L. In another aspect, the composition is provided in a dosage form containing a total amount of about 80 mg of oxycodone, wherein subjects administered a single dosage exhibit a mean plasma oxycodone $AUC_{0 \to \infty}$ of about 1000 h·mg/L.

Another embodiment described herein is a method for treating an individual having pain, with a pharmaceutical composition described herein comprising an abuse deterrent matrix described herein comprising a dosage of about 10 mg of oxycodone to about 80 mg of oxycodone, wherein subjects administered a single dosage exhibits a $T_{max}$ of about 1 hr to about 8 hrs, including each integer within the specified range. In one aspect, the composition is provided in a dosage form containing a total amount of about 10 mg to about 80 mg of oxycodone, wherein subjects administered a single dosage exhibit a $T_{max}$ of about 1 hr, about 1.5 hrs, about 2 hrs, about 2.5 hrs, about 3 hrs, about 3.5 hrs, about 4 hrs, 4.5 hrs, 5 hrs, 5.5 hrs, 6 hrs, 6.5 hrs, 7 hrs, 7.5 hrs, or about 8 hrs.

Another embodiment described herein is a method for treating an individual having pain, with a pharmaceutical composition described herein comprising an abuse deterrent matrix described herein comprising a dosage of about 10 mg of hydrocodone to about 80 mg of hydrocodone, wherein subjects administered a single dosage exhibit a mean plasma hydrocodone $C_{max}$ of about 10 ng/mL to about 120 ng/mL, including each integer within the specified range. In one aspect, the composition is provided in a dosage form containing a total amount of about 10 mg of a hydrocodone, wherein subjects administered a single dosage exhibit a mean plasma hydrocodone $C_{max}$ of about 20 ng/mL. In another aspect, the composition is provided in a dosage form containing a total amount of about 20 mg of hydrocodone, wherein subjects administered a single dosage exhibit a mean plasma hydrocodone $C_{max}$ of about 30 ng/mL. In another aspect, the composition is provided in a dosage form containing a total amount of about 30 mg of hydrocodone, wherein subjects administered a single dosage exhibit a mean plasma hydrocodone $C_{max}$ of about 40 ng/mL. In another aspect, the composition is provided in a dosage form containing a total amount of about 40 mg of hydrocodone, wherein subjects administered a single dosage exhibit a mean plasma hydrocodone $C_{max}$ of about 60 ng/mL. In another aspect, the composition is provided in a dosage form containing a total amount of about 80 mg of hydrocodone, wherein subjects administered a single dosage exhibit a mean plasma hydrocodone $C_{max}$ of about 120 ng/mL.

Another embodiment described herein is a method for treating an individual having pain, with a pharmaceutical composition described herein comprising an abuse deterrent matrix described herein comprising a dosage of about 10 mg of hydrocodone to about 80 mg of hydrocodone, wherein subjects administered a single dosage exhibit a mean plasma hydrocodone $AUC_{0\to\infty}$ of about 100 h·mg/L to about 1600 h·mg/L, including each integer within the specified range. In one aspect, the composition is provided in a dosage form containing a total amount of about 10 mg of a hydrocodone, wherein subjects administered a single dosage exhibit a mean plasma hydrocodone $AUC_{0\to\infty}$ of about 150 h·mg/L. In another aspect, the composition is provided in a dosage form containing a total amount of about 20 mg of hydrocodone, wherein subjects administered a single dosage exhibit a mean plasma hydrocodone $AUC_{0\to\infty}$ of about 400 h·mg/L. In another aspect, the composition is provided in a dosage form containing a total amount of about 40 mg of hydrocodone, wherein subjects administered a single dosage exhibit a mean plasma hydrocodone $AUC_{0\to\infty}$ of about 850 h·mg/L. In another aspect, the composition is provided in a dosage form containing a total amount of about 80 mg of hydrocodone, wherein subjects administered a single dosage exhibit a mean plasma hydrocodone $AUC_{0\to\infty}$ of about 1600 h·mg/L.

Another embodiment described herein is a method for treating an individual having pain, with a pharmaceutical composition described herein comprising an abuse deterrent matrix described herein comprising a dosage of about 10 mg of hydrocodone to about 80 mg of hydrocodone, wherein subjects administered a single dosage exhibits a $T_{max}$ of about 3 hrs to about 8 hrs, including each integer within the specified range. In one aspect, the composition is provided in a dosage form containing a total amount of about 10 mg to about 80 mg of hydrocodone, wherein subjects administered a single dosage exhibit a $T_{max}$ of about 3 hrs, about 4 hrs, about 5 hrs, about 6 hrs, about 7 hrs, or about 8 hrs.

In another embodiment, the pharmaceutical compositions described herein further comprise one or more active pharmaceutical ingredient(s) suitable for treating, ameliorating, or prophylactically treating a bowel dysfunction due to acute or chronic opioid use, often referred to as opioid induced bowel disfunction (OIBD) or opioid induced constipation. Symptoms of OIBD typically comprise constipation (e.g., opioid induced constipation; OIC), anorexia, nausea and vomiting, gastro-oesophageal reflux, delayed digestion, abdominal pain, flatulence, bloating, hard stools, incomplete evacuation or straining during bowel movements. Alternative or additional uses for the one or more active pharmaceutical ingredient(s) described herein may be to treat, reduce, inhibit, or prevent additional effects of acute or chronic opioid use including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of one or more active pharmaceutical ingredient(s) include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculoskeletal system such as osteoporosis, arthritis, osteitis, periostitis, myopathies, and treatment of autoimmune diseases, terminally ill patients receiving opioid therapy such as an AIDS patient, a cancer patient, a cardiovascular patient; subjects receiving opioid therapy for maintenance of opioid withdrawal. In one aspect, the subject is a subject using an opioid for chronic pain management. In another aspect, the subject is a subject using an acutely using an opioid for temporary pain management. In another aspect, the subject is a terminally ill patient. In another aspect, the subject is a person receiving opioid withdrawal maintenance therapy.

In another embodiment, suitable active pharmaceutical ingredients for treating a symptom or condition of opioid use comprise one or more active pharmaceutical ingredients for the treatment, amelioration, or prophylaxis of OIBD or OIC referred to herein as an anti-OIC agent. In some aspects, the anti-OIC agent comprises a peripherally acting mu-opioid receptor antagonist (PAMORA). In some aspects, the PAMORA comprises methylnaltrexone, naltrexone, naloxone, naloxegol, naldemadine, axelopran, alvimopan, or a combination thereof.

In another embodiment, suitable active pharmaceutical ingredients that function as an anti-OIC agent does not function as a PAMORA. Exemplary and non-limiting additional non-PAMORA anti-OIC agents comprise a CLC-2 chloride channel agonist, such as lubiprostone; a non-selective opioid antagonist, such as levallorphan (naloxiphan), etorphine, dihydroetorphine, or diprenorphine; a mixed agonist/antagonist, such as cyclazocine, nalorphine, or nalmexone; a guanylate cyclase agonist, such as linaclotide; or a laxative, such as docusate, magnesium citrate, or senna.

It is understood that activation of mu-opiod receptors along the gastro intestinal tract are responsible for decreased bowel function and constipation. Thus, without being bound by any theory, PAMORAs and other opioid receptor antagonists described herein are useful for preventing symptoms of OIBD, and specifically OIC, by inhibiting the action of the mu-opioid receptor peripherally along the gastro-intestinal tract without inhibiting the mu-opiod receptors of the central nervous system (CNS). Therefore, a combination of an opioid agonist (e.g., oxycodone or hydrocodone) activates the CNS receptors and the co-administration of a PAMORA or other opioid antagonist inhibits the peripheral gut mu-opioid receptors, which are believed to be responsible for the incurrence of OIC.

It is further understood that alternative non-opioid antagonists, such as linaclotide and lubiprostone also prevent OIC symptoms. For example, lubiprostone is known to activate the ClC-2 chloride channels. This activation results in chloride-rich secretions, which soften stool and increase bowel motility resulting in bowel movements. In addition, the guanylate cyclase agonist linaclotide is thought to activate clonic motor neurons, which results in the promotion of bowel movements. Therefore, a combination of an opioid agonist (e.g., oxycodone or hydrocodone) activates the CNS receptors and the co-administration of a non-opioid antagonist anti-OIC agent or laxative prevents OIC by promoting bowel movements.

In one embodiment, the pharmaceutical composition described herein comprises a dose of an anti-OIC agent and a dose of an opioid (e.g., hydrocodone or oxycodone). In one aspect, the dose of an anti-OIC agent ranges from about 50 mg to about 600 mg and the dose of the opioid is from about 5 mg to about 150 mg, including every integer within the specified ranges. In another aspect, the dose of an anti-OIC agent ranges from about 50 mg to about 550 mg and the dose of the opioid is from about 5 mg to about 150 mg, including every integer within the specified ranges. In another aspect, the dose of an anti-OIC agent ranges from about 5 mg to about 50 mg and the dose of the opioid is from about 5 mg to about 100 mg, including every integer within the specified ranges.

In another embodiment, the weight percentage ratio range of an anti-OIC agent to opioid (e.g., hydrocodone or oxycodone) in the pharmaceutical composition described herein ranges from about 15:1 to about 1:18, including each ratio within the specified range. In one aspect, the weight percentage ratio range of an anti-OIC agent to opioid is from about 13:1 to about 1:1, including each ratio within the specified range. In another aspect, the weight percentage ratio range of an anti-OIC agent to opioid is from about 1:16 to about 1:1, including each ratio within the specified range. In another aspect, the weight percentage ratio range of an anti-OIC agent to opioid is about 1:16, about 1:15, about 1:14, about 1:13, about 1:12, about 1:11, about 1:10, about 1:9, about 1:8, about 1:7, about 1:6, about 1:5, about 1:4, about 1:3, about 1:2, about 1:1, about 2:1, about 3:1, about 4:1, about 5:1, about 6:1, about 7:1, about 8:1, about 9:1, about 10:1, about 11:1, about 12:1, about 13:1, about 14:1, or about 15:1.

In one embodiment, the pharmaceutical compositions described herein comprise a dose of an opioid (e.g., oxycodone or hydrocodone) and a dose of a PAMORA. In one aspect, the pharmaceutical compositions described herein comprise a dose of an opioid and a dose of a PAMORA comprising naloxone or a pharmaceutically acceptable salt form thereof. In one aspect, the pharmaceutical compositions described herein comprise a dose of an opioid and a dose of a PAMORA comprising naltrexone or a pharmaceutically acceptable salt form thereof. In another aspect, the pharmaceutical compositions described herein comprise a dose of an opioid and a dose of a PAMORA comprising methylnaltrexone or a pharmaceutically acceptable salt form thereof. In another aspect, the pharmaceutical compositions described herein comprise a dose of an opioid and a dose of a PAMORA comprising naloxegol or a pharmaceutically acceptable salt form thereof.

In one embodiment, the pharmaceutical composition described herein comprises a dose of naloxone and a dose of an opioid comprising hydrocodone or oxycodone as described herein. In one aspect, the dose of the naloxone ranges from about 2.5 mg to about 100 mg, including each integer within the specified range. In another aspect, the dose of naloxone ranges from about 2.5 mg to about 50 mg, including each integer within the specified range. In another aspect, the dose of naloxone ranges from about 10 mg to about 50 mg, including each integer within the specified range. In another aspect, the dose of naloxone ranges from about 20 mg to about 40 mg, including each integer within the specified range. In another aspect, the dose of naloxone is about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In another embodiment, the weight percentage ratio range of naloxone to opioid comprising hydrocodone or oxycodone in the pharmaceutical composition described herein ranges from about 1:10 to about 5:1, including all iterations of ratios within the specified range. In one aspect, the weight percentage ratio range of naloxone to opioid comprising hydrocodone or oxycodone is from about 1:5 to about 1:1, including all iterations of ratios within the specified range. In another aspect, the weight percentage ratio range of naloxone to opioid comprising hydrocodone or oxycodone is from about 1:4 to about 1:2, including all iterations of ratios within the specified range. In another aspect, the weight percentage ratio range of naloxone to opioid comprising hydrocodone or oxycodone is about 1:10, about 1:9, about 1:8, about 1:7, about 1:6, about 1:5, about 1:4, about 1:3, about 1:2, about 1:1, about 2:1, about 3:1, about 4:1, or about 5:1. In another aspect, the weight percentage ratio range of naloxone to opioid comprising hydrocodone or oxycodone is about 1:2.

In another embodiment, the pharmaceutical composition described herein comprises a dose of about 5 mg of naloxone and a dose of about 10 mg of oxycodone. In another embodiment, the pharmaceutical composition described herein comprises a dose of about 10 mg of naloxone and a dose of about 20 mg of oxycodone. In another embodiment, the pharmaceutical composition described herein comprises a dose of about 20 mg of naloxone and a dose of about 40 mg of oxycodone. In another embodiment, the pharmaceutical composition described herein comprises a dose of about 40 mg of naloxone and a dose of about 80 mg of oxycodone. In another embodiment, the pharmaceutical composition described herein comprises a dose of about 80 mg of naloxone and a dose of about 160 mg of oxycodone.

In another embodiment, the pharmaceutical composition described herein comprises a dose of about 5 mg of naloxone and a dose of about 10 mg of hydrocodone. In another embodiment, the pharmaceutical composition described herein comprises a dose of about 10 mg of naloxone and a dose of about 20 mg of hydrocodone. In another embodiment, the pharmaceutical composition described herein comprises a dose of about 20 mg of naloxone and a dose of about 40 mg of hydrocodone. In another embodiment, the pharmaceutical composition described herein comprises a dose of about 40 mg of naloxone and a dose of about 80 mg of hydrocodone. In another embodiment, the pharmaceutical composition described herein comprises a dose of about 80 mg of naloxone and a dose of about 160 mg of hydrocodone.

In another embodiment, the pharmaceutical composition described herein comprises a dose of about 40 mg of oxycodone and a dose of about 20 mg of naloxone. In one aspect, the composition is provided in a dosage form containing a total amount of about 40 mg of oxycodone and about 20 mg of naloxone, wherein subjects administered a single dosage exhibit a mean plasma oxycodone $AUC_{0\to\infty}$ of about 400 h·mg/L to about 600 h·mg/L and a mean plasma naloxone $AUC_{0\to\infty}$ of about 500 h·mg/L to about 600 h·mg/L. In another aspect, the composition is provided in a dosage form containing a total amount of about 40 mg of oxycodone and about 20 mg of naloxone, wherein subjects administered a single dosage exhibit a mean plasma oxycodone $C_{max}$ of about 30 ng/mL to about 50 ng/mL and a mean plasma naloxone $C_{max}$ of about 50 ng/mL to about 70 ng/mL. In another aspect, the composition is provided in a dosage form containing a total amount of about 40 mg of oxycodone and about 20 mg of naloxone, wherein subjects administered a single dosage exhibit an oxycodone $T_{max}$ of about 1 hr to about 5 hrs and a naloxone $T_{max}$ of about 0.5 hr to about 3 hrs.

In one embodiment, the pharmaceutical composition described herein comprises a dose of methylnaltrexone or naltrexone and a dose of an opioid comprising hydrocodone or oxycodone as described herein. In one aspect, the dose of the methylnaltrexone or naltrexone ranges from about 2.5 mg to about 100 mg, including each integer within the specified range. In another aspect, the dose of methylnaltrexone or naltrexone ranges from about 50 mg to about 600 mg, including each integer within the specified range. In another aspect, the dose of methylnaltrexone or naltrexone ranges from about 100 mg to about 600 mg, including each integer within the specified range. In another aspect, the dose of methylnaltrexone or naltrexone ranges from about 300 mg to about 600 mg, including each integer within the specified range. In another aspect, the dose of methylnaltrexone or naltrexone ranges from about 400 mg to about 600 mg, including each integer within the specified range. In another aspect, the dose of methylnaltrexone or naltrexone is about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, or about 550 mg.

In another embodiment, the weight percentage ratio range of methylnaltrexone or naltrexone to opioid comprising hydrocodone or oxycodone in the pharmaceutical composition described herein ranges from about 13:1 to about 1:1, including all iterations of ratios within the specified range. In one aspect, the weight percentage ratio range of methylnaltrexone or naltrexone to opioid comprising hydrocodone or oxycodone is from about 10:1 to about 1:1, including all iterations of ratios within the specified range. In another aspect, the weight percentage ratio range of methylnaltrexone or naltrexone to opioid comprising hydrocodone or oxycodone is from about 5:1 to about 1:1, including all iterations of ratios within the specified range. In another aspect, the weight percentage ratio range of methylnaltrexone or naltrexone to opioid comprising hydrocodone or oxycodone is about 1:1, about 2:1, about 3:1, about 4:1, about 5:1, about 6:1, about 7:1, about 8:1, about 9:1, about 10:1, about 11:1, about 12:1, or about 13:1.

In one embodiment, the pharmaceutical composition described herein comprises a dose of naloxegol and a dose of an opioid comprising hydrocodone or oxycodone as described herein. In one aspect, the dose of the naloxegol ranges from about 2.5 mg to about 100 mg, including each integer within the specified range. In another aspect, the dose of naloxegol ranges from about 2.5 mg to about 50 mg, including each integer within the specified range. In another aspect, the dose of naloxegol ranges from about 10 mg to about 50 mg, including each integer within the specified range. In another aspect, the dose of naloxegol ranges from about 20 mg to about 40 mg, including each integer within the specified range. In another aspect, the dose of naloxegol is about 2.5 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg.

In another embodiment, the weight percentage ratio range of naloxegol to opioid comprising hydrocodone or oxycodone in the pharmaceutical composition described herein ranges from about 1:10 to about 5:1, including all iterations of ratios within the specified range. In one aspect, the weight percentage ratio range of naloxegol to opioid comprising hydrocodone or oxycodone is from about 1:5 to about 1:1, including all iterations of ratios within the specified range. In another aspect, the weight percentage ratio range of naloxegol to opioid comprising hydrocodone or oxycodone is from about 1:4 to about 1:2, including all iterations of ratios within the specified range. In another aspect, the weight percentage ratio range of naloxegol to opioid comprising hydrocodone or oxycodone is about 1:10, about 1:9, about 1:8, about 1:7, about 1:6, about 1:5, about 1:4, about 1:3, about 1:2, about 1:1, about 2:1, about 3:1, about 4:1, or about 5:1. In another aspect, the weight percentage ratio range of naloxegol to opioid comprising hydrocodone or oxycodone is about 1:2.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, headache, vertigo, somnolence, nausea, constipation, vomiting, xerostomia, fatigue, pruritus, eructation, heartburn, abdominal discomfort, or loss of appetite.

Another embodiment described herein is a method for treating, retarding the progression of, prophylaxis of, delaying the onset of, ameliorating, or reducing the symptoms of pain comprising the administration of a therapeutically effective amount of one or more abuse deterrent pharmaceutical compositions described herein to a subject with pain, wherein the administration is sufficient to achieve a reduction pain relative to baseline in the subject without substantially inducing one or more side effects including, but not limited to, opioid use, such as, for example, opioid induced bowel dysfunction, opioid induced constipation, gastrointestinal dysfunction (e.g., inhibition of intestinal motility, constipation, GI sphincter constriction), nausea, emesis (vomiting), biliary spasm, colic, dysphoria, pruritus, urinary retention, depression of respiration, papillary constriction, cardiovascular effects, chest wall rigidity and cough suppression, depression of stress response, and immune suppression associated with use of narcotic analgesia, etc, or combinations thereof.

Another embodiment described herein is a method for treating, retarding the progression of, prophylaxis of, delaying the onset of, ameliorating, or reducing the symptoms of, irritable bowel syndrome, colitis, post-operative or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (colectomy, e.g., right hemicolectomy, left hemicolectomy, transverse hemicolectomy, colectomy takedown, low anterior resection), and delayed absorption of orally administered medications or nutritive substances comprising the administration of a therapeutically effective amount of one or more abuse deterrent pharmaceutical compositions described herein.

Another embodiment described herein is a method for improving the quality of life of subjects receiving opioids, as well as to reduce complications arising from chronic constipation, such as hemorrhoids, appetite suppression, mucosal breakdown, sepsis, colon cancer risk, and myocardial infarction comprising the administration of a therapeutically effective amount of one or more abuse deterrent pharmaceutical compositions described herein.

In another embodiment, the pharmaceutical composition described herein provides a dosage form comprising an opioid and a PAMORA as described in, which in terms of efficacy, is ranked good or very good by more than 50% of patients, 60%, 70%, 80%, 90%, or more of patients. In aspect, the dosage form is provided which comprises an opioid and a PAMORA as described in, which in terms of tolerability, is ranked good or very good by more than 50% of patients, 60%, 70%, 80%, 90%, or more of patients.

In another embodiment, the pharmaceutical composition described herein provides a dosage form comprising an opioid and a PAMORA as described in, which provides a reduction of days with laxative intake by at least 10%, 20%, 30%, 40%, 50%, 60%, 70%, 80%, or even 90%. In one aspect, the dosage form completely reduces the need for any laxatives to be taken independently.

In some embodiments, bowel function is assessed by observing parameters that are associated with bowel function. In particular, bowel function may be determined based on parameters selected from ease or difficulty of defecation, feeling of incomplete bowel evacuation, and/or personal judgment of patient regarding constipation. Other parameters which may be observed alternatively or in addition in order to assess the bowel function of a patient include among other things stool frequency, stool consistency, cramping, and painful laxation. In addition, the measurement of spontaneous bowel movements indicates improved bowel function.

Bowel function may be assessed by measuring parameters, which are associated with bowel function using numerical analog scales (NAS) for these parameters because this may provide more accurate results. This approach is particularly advantageous when assessing the bowel function in patients receiving treatment with analgesics, because analgesic efficacy of drugs is usually assessed using a numeric analog scale.

In one embodiment, a reduction in OIC is assessed by measuring a change in the spontaneous bowel movements (SBMs) frequency rate (e.g., SBMs/week). Patients are typically classified as having OIC when having less than 3 SBMs per week for about 4 weeks while taking an opioid. A positive response to an OIC agent is assessed as an increase in SBMs over a period of time following the administration of the OIC agent.

In one embodiment, the administration of the pharmaceutical composition described herein provides an improvement of bowel function during pain therapy by increasing the number of spontaneous bowel movements per week over a time course of about 1 week to about 12 weeks, including each integer within the specified range. In one aspect, the time course is about 1 week to about 4 weeks, including each integer within the specified range. In another aspect, the time course is about 1 week, about 2 weeks, about 3 weeks, about 4 weeks, about 5 weeks, about 6 weeks, about 7 weeks, about 8 weeks, about 9 weeks, about 10 weeks, about 11 weeks, or about 12 weeks. In another aspect, the improvement in the number of spontaneous bowel movements per week comprises between about 1 and about 10 additional spontaneous bowel movements per week, including each integer within the specified range. In another aspect, the improvement in the number of spontaneous bowel movements per week comprises between about 1 and about 5 additional spontaneous bowel movements per week, including each integer within the specified range. In another aspect, the improvement in the number of spontaneous bowel movements per week comprises between about 1, about 2, about 3, about 4, about 5, about 6, about 7, about 8, about 9, or about 10 additional spontaneous bowel movements per week.

In another embodiment a reduction in OIC by an anti-OIC agent is assessed by measuring the time to first SBM following administration of the anti-OIC agent compared to a placebo agent.

In another embodiment, a reduction in OIC by an anti-OIC agent is assessed by measuring a change in stool consistency from baseline over a period of time. For example, the Bristol Stool Scale may be used to assess changes.

In some embodiments, the pharmaceutical compositions comprising an opioid and an anti-OIC agent as described herein provides improvement of the bowel function characterized by an increase of the mean bowel function score of at least 5, at least about 8, at least about 10 or at least about 15 after administration at steady state or of a single dose to human patients or healthy human subjects, wherein the mean bowel function score is measured with a numerical analog scale ranging from 0 to 100.

In one embodiment, the bowel function is assessed by the bowel function index (BFI), which is measured in patients. The mean bowel function score may be determined by a method for assessing bowel function in a patient comprising the steps of: providing the patient with a numeric analog scale for at least one parameter, which parameter is associated with bowel function; causing the patient to indicate on the numeric analog scale the amount and/or intensity of the parameter being experienced; and observing the amount and/or intensity of the at least one parameter indicated on the numeric analog scale in order to assess bowel function. In one aspect the patient indicates the amount and/or intensity of parameter being experienced during the last days or weeks, e.g. during the last 1, 2, 3, 4, 5, 6, 7, 10, or 14 days. In another aspect, the numerical analog scale on which the patient indicates his/her subjective experience of the observed parameter may have any size or form and may range from 0 or any other number to any number, such as from 0 to 10 or from 0 to 50 or from 0 to 300 or from 1 to 10.

In another embodiment, if more than one parameter is observed, a mean bowel function may be obtained in form of a numerical value. This numerical value is the mean of the parameters observed, e.g., the three numeric analog scale values for ease or difficulty of defecation, feeling of incomplete bowel evacuation and judgment of constipation. The parameters, which are measures of bowel function or which are associated with bowel function, may comprise opioid induced bowel dysfunctions (OIBD or OIC) as described herein.

In another embodiment, bowel function may be determined based on the following parameters: ease or difficulty of defecation, for example during the last 7 days according to the patient assessment, wherein 0 corresponds to no difficulties and 100 corresponds to severe difficulties; feeling of incomplete bowel evacuation, for example during the last 7 days according to the patient assessment, wherein 0 corresponds to no feeling of incomplete bowel evacuation and 100 corresponds to very strong feeling of incomplete bowel evacuation; personal judgment of patient regarding constipation, for example during the last 7 days, wherein 0 corresponds to no constipation at all and 100 corresponds to very heavy constipation.

In another embodiment, bowel function may be assessed with analogs scales as described in U.S. Pat. No. 6,258,042 and International Patent Application Publication No. WO 2003/073937, which may be adapted to devices or analog scales as described above as would be understood by one of ordinary skill in the art. The disclosures of these two references are hereby incorporated by reference for such teachings.

In another embodiment, the pharmaceutical compositions described herein further comprise one or more active pharmaceutical ingredient(s) comprising a PAMORA may also further limit or prevent drug abuse by inhibiting the action or effects of an opioid. The PAMORAs described herein, for example, methylnaltrexone, naltrexone, naloxone, naloxegol, or alvimopan can function to have an aversive effect. This aversive affect may include any unpleasant side effect comprising inducing opioid withdrawl symptoms, diarrhea, nausea, reduced euphoria or a mixture or combination thereof.

In another embodiment, the abuse deterrent pharmaceutical composition described herein is contained and dispensed from a tamper evident packaging. The term "tamper evident" or "tamper resistant" refers to a packaging of any kind that readily displays or allows for an individual to observe any physical interference or manipulation of said packaging. The tamper evident packaging provides reasonable evidence to consumers that tampering has occurred. The tamper evident packaging additionally contains appropriate labelling statements describing the features and evidences of the tamper evident packaging. In one aspect, the tamper evident packaging comprises: bottles, film wrappers, blister or strip packs, bubble packs, heat shrink bands or wrappers, foil, paper, or plastic pouches, container mouth inner seals, tape seals, breakable caps, sealed metal tubes or plastic heat-sealed tubes, sealed cartons, aerosol containers, cans including metal and composite materials, or any combination thereof. The packaging may also contain appropriate instructions for prescribing, instructions for use, warnings, or other appropriate information.

It will be apparent to one of ordinary skill in the relevant art that suitable modifications and adaptations to the compositions, formulations, methods, processes, and applications described herein can be made without departing from the scope of any embodiments or aspects thereof. The compositions and methods provided are exemplary and are not intended to limit the scope of any of the specified embodiments. All of the various embodiments, aspects, and options disclosed herein can be combined in any and all variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. Furthermore, the foregoing discussion discloses and describes merely exemplary embodiments. All patents and publications cited herein are incorporated by reference herein for the specific teachings thereof.

EXAMPLES

Example 1

Abuse deterrent matrices as described herein were prepared using the composition shown in Tables 4-6. The compositions were prepared according to the method of Example 2 and encapsulated in a hard capsule shell. Other suitable non-limiting capsule shells for the abuse deterrent matrices described herein comprise a soft capsule shell, enteric soft capsule shell, or an enteric hard capsule shell.

TABLE 4

Abuse Deterrent Non-Burst Releasing Controlled Release Matrix Compositions

| Ingredients | Weight Percentage (%) | | | | | |
|---|---|---|---|---|---|---|
| | F1 | F2 | F3 | F4 | F5 | F6 |
| Oleic Acid | 65.11 | 64.54 | 63.79 | 63.29 | 62.04 | 62.71 |
| Ethocel™ 20cP | 1 | 1 | 1 | 1 | 1 | 1 |
| Polyethylene oxide (301 FP) | 32 | 30 | 30 | 30 | 30 | 30 |
| BHA | 0.19 | 0.19 | 0.19 | 0.19 | 0.19 | 0.25 |
| BHT | 0.08 | 0.08 | 0.08 | 0.08 | 0.08 | 0.08 |
| Sodium lauryl sulfate | 0 | 2.5 | 3.25 | 3.75 | 5.0 | 3.75 |
| Hydrocodone bitartrate | 1.63 | 1.69 | 1.69 | 1.69 | 1.69 | 2.19 |
| TOTAL | 100 | 100 | 100 | 100 | 100 | 100 |
| Fill Weight | 650 mg | 650 mg | 650 mg | 650 mg | 650 mg | 502 mg |

TABLE 5

Abuse Deterrent Non-Burst Releasing Controlled Release Matrix Compositions

| Ingredients | Weight Percentage (%) F7 | Weight Percentage (%) F8 | Weight Percentage (%) F9 | Weight Percentage (%) F10 |
|---|---|---|---|---|
| Maisine™ 35-1 | 63.04 | 65.54 | 66.15 | 65.46 |
| Polyethylene oxide (WSR 301) | 30.0 | 30.0 | 32.0 | 32.0 |
| BHA | 0.19 | 0.19 | 0.19 | 0.25 |
| BHT | 0.08 | 0.08 | 0.08 | 0.10 |
| Sodium lauryl sulfate | 5.0 | 2.5 | — | — |
| Hydrocodone bitartrate | 1.69 | 1.69 | 1.58 | 2.19 |
| TOTAL | 100 | 100 | 100 | 100 |
| Fill Weight | 650 mg | 650 mg | 650 mg | 502 mg |

TABLE 6

Abuse Deterrent Non-Burst
Releasing Controlled Release Matrix Compositions

| Ingredients | Weight Percentage (%) | | | | |
|---|---|---|---|---|---|
| | F11 | F12 | F13 | F14 | F15 |
| Oleic Acid | 61.08 | 63.04 | 63.04 | 59.54 | 57.04 |
| Ethocel™ 20 cP | 1.0 | — | — | 1.0 | 1.0 |
| Ethocel™ 4 cP | — | 5.0 | — | — | — |
| Hydroxy ethyl cellulose | — | — | — | 2.50 | 5.0 |
| Eudragit® S100 | — | — | 5.0 | — | — |
| Polyethylene oxide (301 FP) | 30.0 | 30.0 | 30.0 | 30.0 | 30.0 |
| BHA | 0.30 | 0.19 | 0.19 | 0.19 | 0.19 |
| BHT | 0.13 | 0.08 | 0.08 | 0.08 | 0.08 |
| Sodium lauryl sulfate | 5.0 | — | — | 5.0 | 5.0 |
| Hydrocodone bitartrate | 2.49 | 1.69 | 1.69 | 1.69 | 1.69 |
| TOTAL | 100 | 100 | 100 | 100 | 100 |
| Fill Weight | 402 | 650 | 650 | 650 | 650 |

Example 2

Abuse deterrent non-burst releasing controlled release matrices according to compositions F1-F6 and F11-F15 of Tables 4 and 6 were prepared by heating the specified amount of oleic acid or Maisine™ 35-1 to 140° C. This mixture was then cooled to about 85° C. and BHA and BHT was added until completely dissolved. The resulting mixture was cooled to approximately 30° C. and the specified amount of the active pharmaceutical ingredient hydrocodone bitartrate and polyethylene oxide 301, and as indicated, sodium lauryl sulfate, hydroxy ethyl cellulose, or Eudragit® S100 was added and mixed until uniformly suspended in a dispersion. The resulting liquid mixture was encapsulated in hard shell capsules as a liquid suspension and was annealed at 60° C. to 70° C. for 0.5 hr to 1.5 hr.

The abuse deterrent non-burst releasing controlled release matrix according to composition F7-F10 of Table 5 was prepared by heating the specified amount of Maisine™ 35-1 to 65° C. BHA and BHT were added until completely dissolved. This mixture was then cooled to about 30° C. and the specified amount of the active pharmaceutical ingredient hydrocodone bitartrate was added and mixed until uniformly dispersed. Next the specified amount of polyethylene oxide 301, and as indicated, sodium lauryl sulfate was added and mixed uniformly to form a suspension mixture. The resulting liquid mixture was encapsulated as a liquid suspension into hard capsules and was dried and for 45±15 minutes at 70±2° C.

The abuse deterrent matrices prior to encapsulation and annealing had a viscous, yet flowable aspect. After the annealing step at 70° C., the matrices had a semi-solid elastic aspect.

The process for manufacturing a soft capsule comprising the non-burst releasing abuse deterrent matrices as described herein includes preparing a gel mass for a soft capsule; casting the gel mass into films or ribbons using heat-controlled drums or surfaces; and manufacturing a soft capsule comprising a matrix fill using rotary die technology. During this process, the abuse deterrent controlled release matrix is injected into the lumen as the soft capsule is formed by rotary die encapsulation. The soft capsule can be a typical soft capsule ("soft gel") or an enteric soft capsule.

Example 3

The melting point of PEO in different flowability enhancers including medium chain mono- and di-glyceride (e.g., Capmul® MCM), oleic acid, or glyceryl monolinoleate (e.g., Maisine™ 35-1) was tested. It is hypothesized that the PEO release modifier is suspended and not dissolved within the flowability enhancer throughout the processing steps. During the annealing steps, however, the release modifier is believed to become molten and the two components may be miscible. When cooled, the release modifier subsequently recrystallizes and forms a semi-solid elastic matrix that encapsulates the flowability enhancer and an active pharmaceutical ingredient. Thermograms show that PEO exhibits a significant melting point depression in the presence of Capmul® MCM, which impacts processability (FIG. 1). Other flowability enhancers, such as Maisine™ 35-1, oleic acid, Span® 80, and Tween® 20, also decreased the PEO melting point but to a lesser extent. An inert diluent powder, microcrystalline cellulose, was used as a control, which demonstrated no impact on the melting point.

Example 4

The dissolution and release profiles under different dissolution conditions for pharmaceutical compositions comprising the test abuse deterrent matrix compositions described in Tables 4-6 are shown in FIGS. 2-12.

Figure 2:
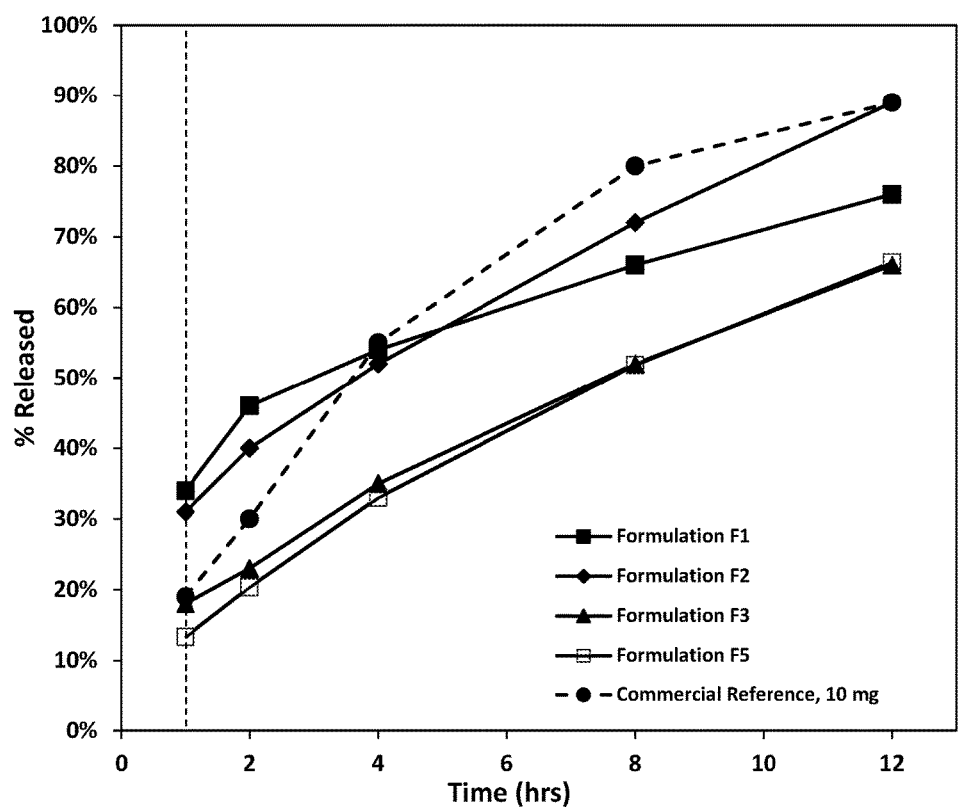
FIG. 2. Percent release of hydrocodone bitartrate (10 mg) from a test abuse deterrent pharmaceutical compositions (F1, F2, F3, and F5) compared to the percent release of hydrocodone from a reference extended release 10 mg formulation in fasted-state simulated gastric fluid (FASSGF) and fasted-state simulated intestinal fluid (FASSIF) buffer using Apparatus III at 30 dips per minute.
Figure 3:
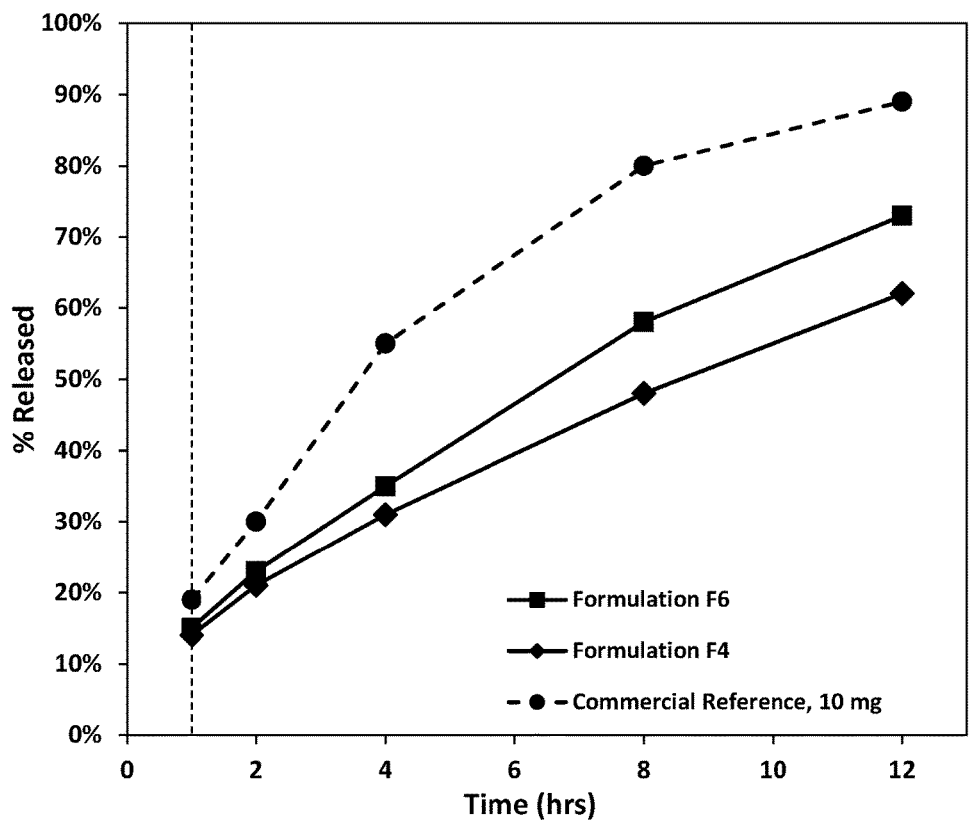
FIG. 3. Percent release of hydrocodone bitartrate (10 mg) from a test abuse deterrent pharmaceutical compositions (F4 and F6) having differing fill weights compared to the percent release of hydrocodone from a reference extended release 10 mg formulation in FASSGF and FASSIF buffer using Apparatus III at 30 dips per minute.
Figure 4:
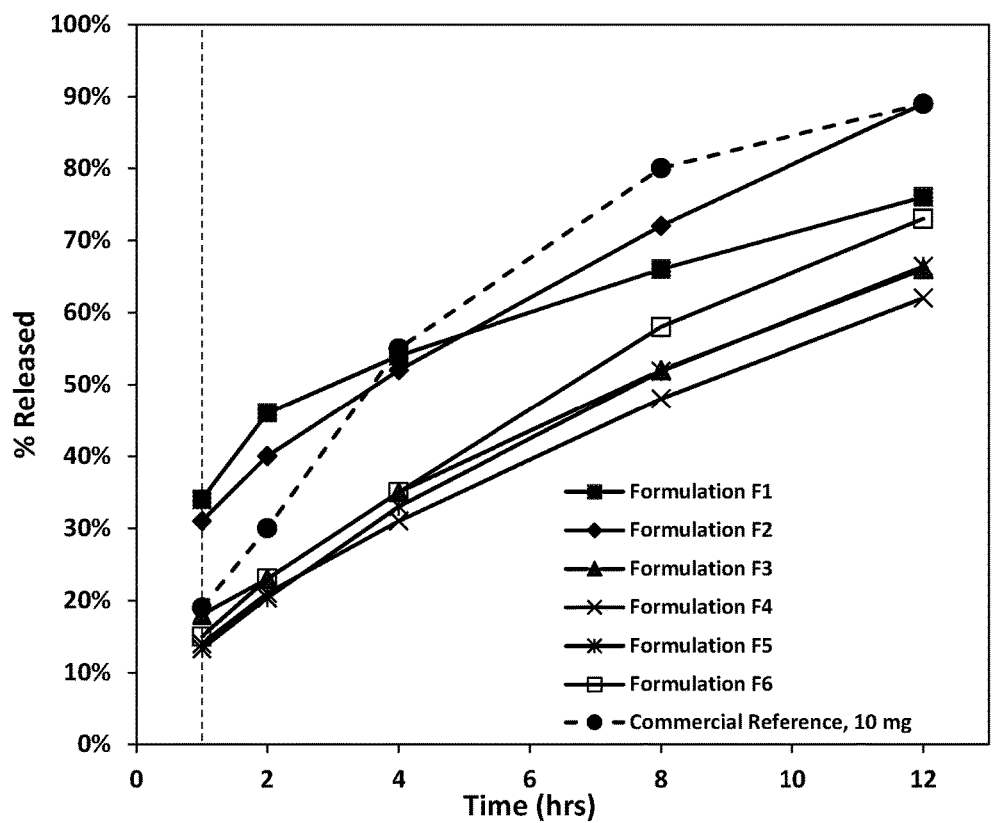
FIG. 4. Percent release of hydrocodone bitartrate (10 mg) from a test abuse deterrent pharmaceutical compositions (F1-F6) compared to the percent release of hydrocodone from a reference extended release 10 mg formulation in FASSGF and FASSIF buffer using Apparatus III at 30 dips per minute.
Figure 5:
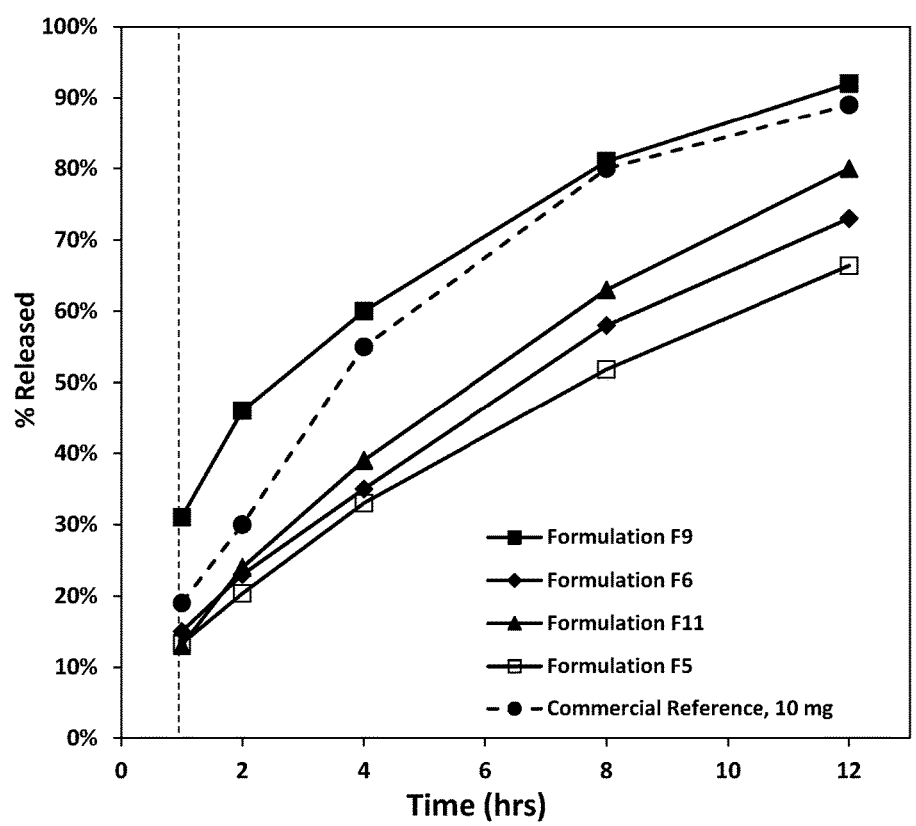
FIG. 5. Percent release of hydrocodone bitartrate (10 mg) from a test abuse deterrent pharmaceutical compositions (F5, F6, F9, and F11) having differing fill weights compared to the percent release of hydrocodone from a reference extended release 10 mg formulation in FASSGF and FASSIF buffer using Apparatus III at 30 dips per minute.
Figure 6:
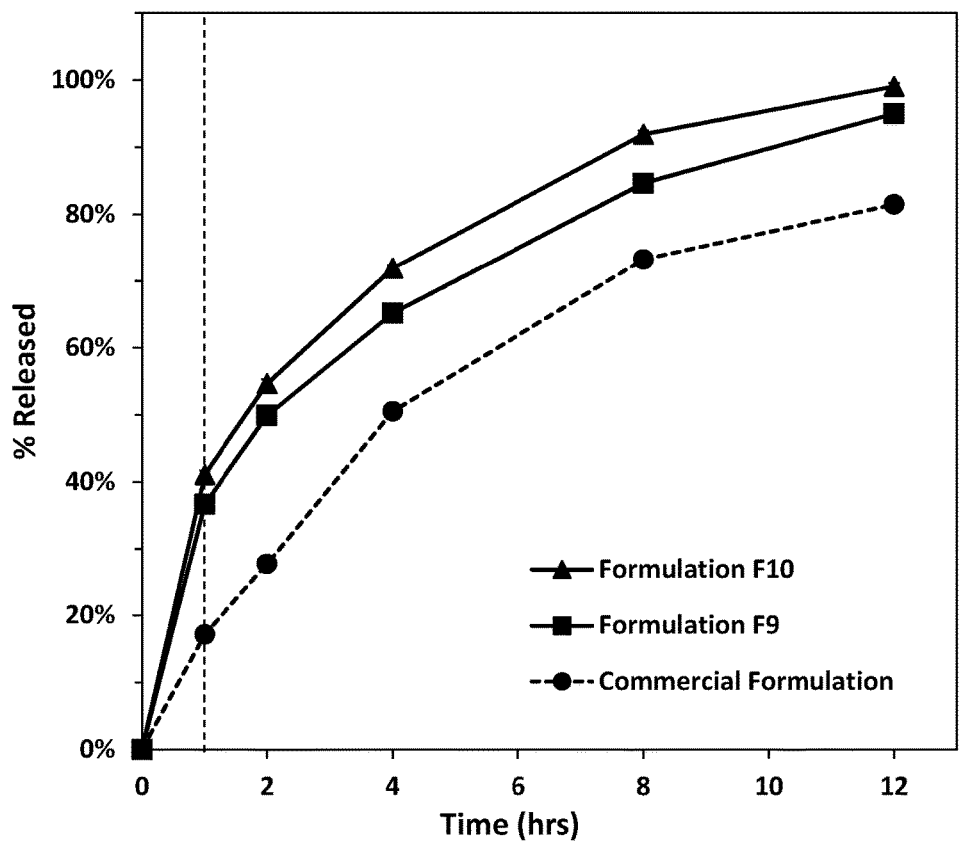
FIG. 6. Percent release of hydrocodone bitartrate (10 mg) from a test abuse deterrent pharmaceutical compositions not having SLS (F9 and F10) compared to the percent release of hydrocodone from a reference extended release 10 mg formulation in FASSGF and FASSIF buffer using Apparatus III at 30 dips per minute.
Figure 7:
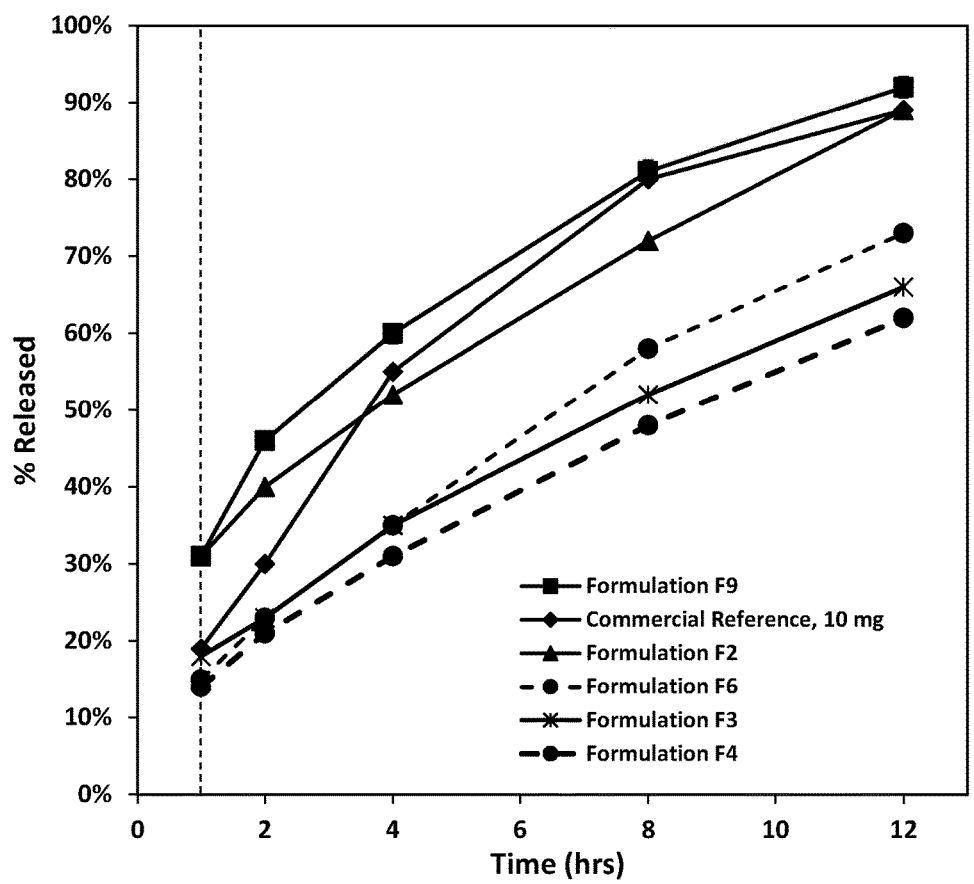
FIG. 7. Percent release of hydrocodone bitartrate (10 mg) from a test abuse deterrent pharmaceutical compositions having SLS (F2, F3, F4, and F6) or not having SLS (F9) compared to the percent release of hydrocodone from a reference extended release 10 mg formulation in FASSGF and FASSIF buffer using Apparatus III at 30 dips per minute.
Figure 8:
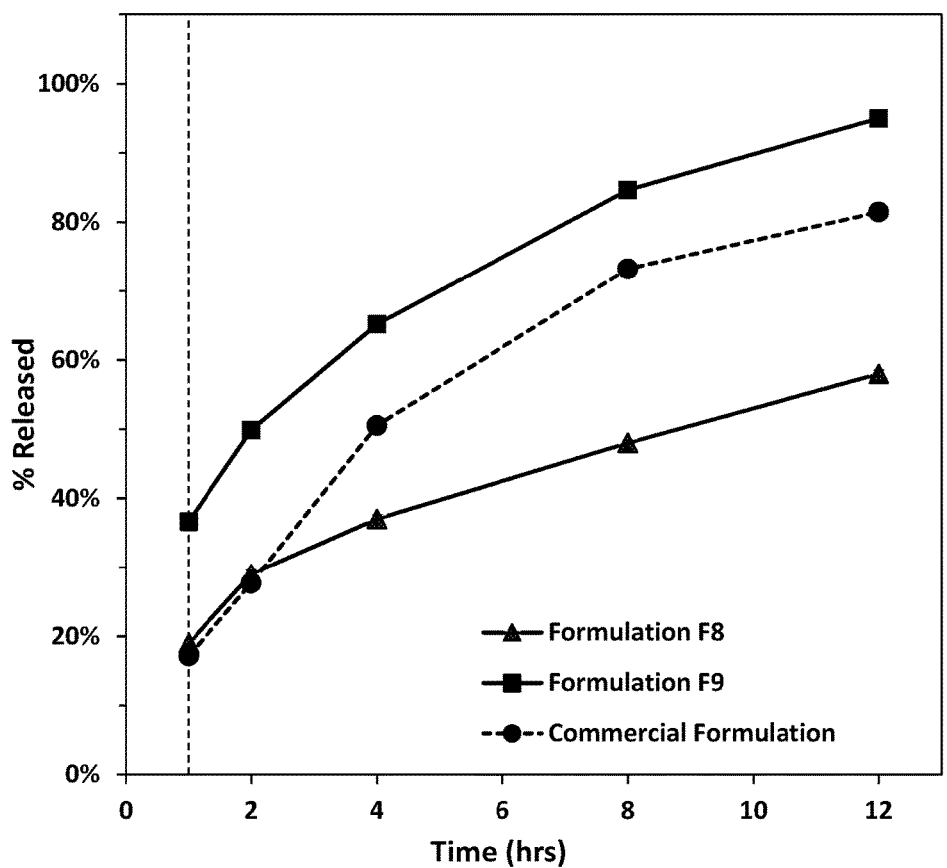
FIG. 8. Percent release of hydrocodone bitartrate (10 mg) from a test abuse deterrent pharmaceutical compositions having SLS (F8) or not having SLS (F9) compared to the percent release of hydrocodone from a reference extended release 10 mg formulation in FASSGF and FASSIF buffer using Apparatus III at 30 dips per minute.
Figure 9:
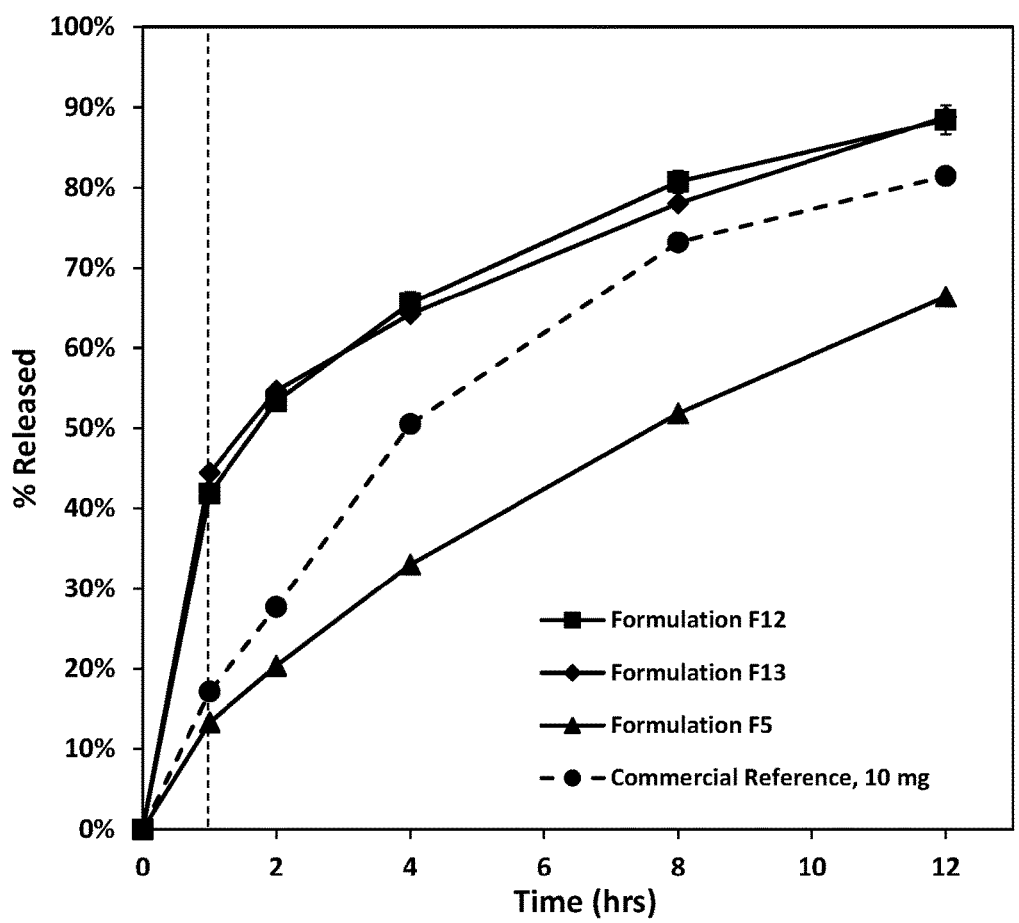
FIG. 9. Percent release of hydrocodone bitartrate (10 mg) from a test abuse deterrent pharmaceutical compositions (F5, F12, and F13) having different viscosity modifier or release modifier polymers compared to the percent release of hydrocodone from a reference extended release 10 mg formulation in FASSGF and FASSIF buffer using Apparatus III at 30 dips per minute.
Figure 10:
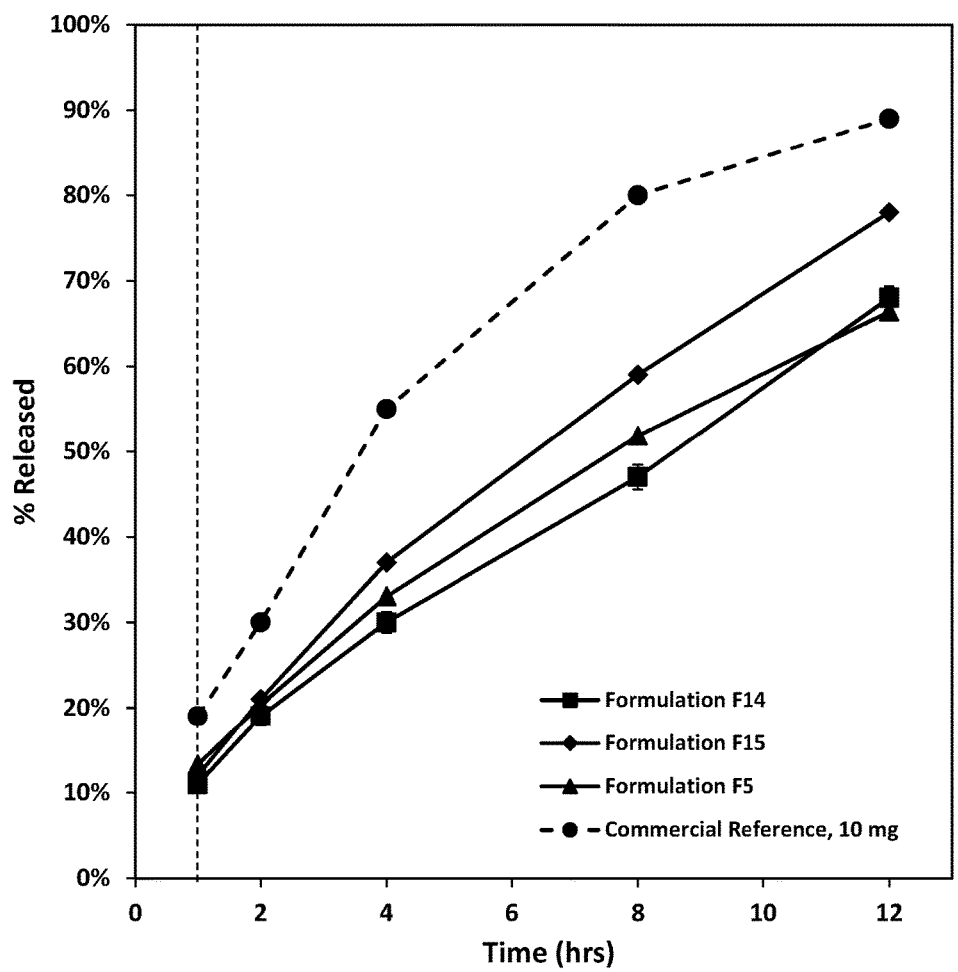
FIG. 10. Percent release of hydrocodone bitartrate (10 mg) from a test abuse deterrent pharmaceutical compositions (F5, F14, and F15) having different release modifier polymers compared to the percent release of hydrocodone from a reference extended release 10 mg formulation in FASSGF and FASSIF buffer using Apparatus III at 30 dips per minute.

The percent release of hydrocodone bitartrate (10 mg) from the abuse deterrent controlled release matrix compositions F1, F2, F3, and F5 shown in Table 4, generated by the method described in example 2 and encapsulated in a hard shell capsule, were tested and compared to a commercially available extended release formulation of hydrocodone bitartrate (FIG. 2). Formulation F3 having 3.25% sodium lauryl sulfate (SLS) demonstrated no burst release of hydrocodone when compared to formulation F1 (FIG. 2). Additional formulations having between 3.25% and 5.0% SLS that were tested with oleic acid also demonstrated no burst release and increasing the concentration of sodium lauryl sulfate generally extended the release rate of hydrocodone from the composition (FIGS. 3 and 4). Furthermore, as shown in FIG. 5, this reduced burst release was obtained with lower fill weights (F6, F11, 402 mg; F6, 502 mg; F5, 650 mg). Formulations having the flowability enhancer Maisine™ 35-1 also demonstrated a burst release (FIGS. 6 and 7). Consistent with the results obtained with oleic acid, the presence of sodium lauryl sulfate reduced this initial burst release of formulations having the flowability enhancer Maisine™ 35-1 (e.g., F8 vs. F9; FIG. 8). The use of additional or alternative release modifier polymers hydroxy ethyl cellulose or Eudragit® S100 and a less viscous viscosity modifier Ethocel™ 4 cP were tested and demonstrated similar results (FIGS. 9 and 10).

Figure 11:
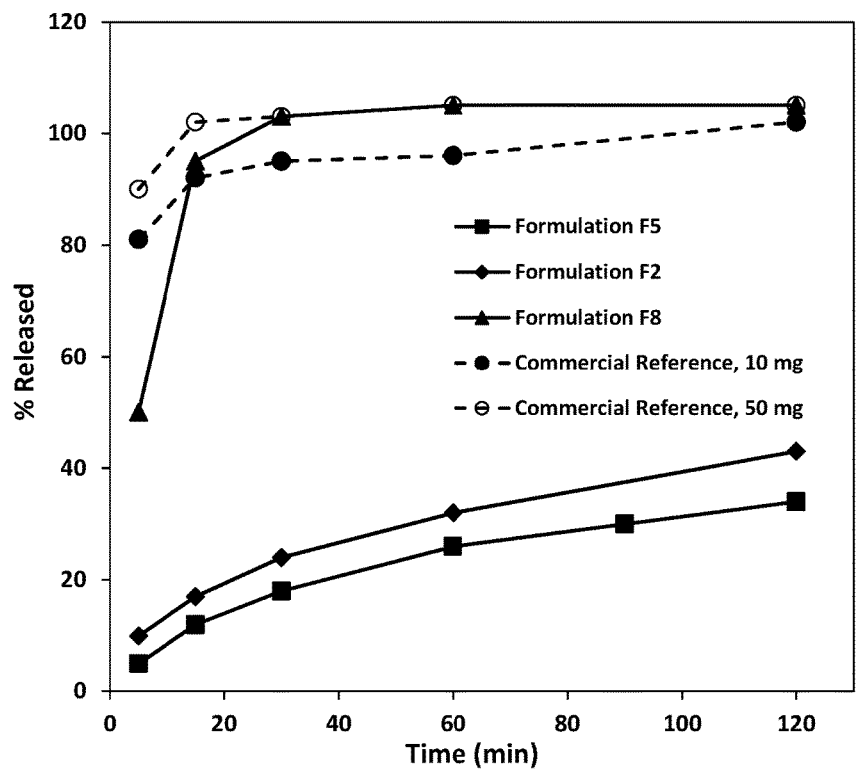
FIG. 11. Percent release of hydrocodone bitartrate (10 mg) from test abuse deterrent pharmaceutical compositions (F2, F5, and F7) compared to the percent release of hydrocodone from a reference extended release 10 mg and 50 mg formulations under aqueous boiling conditions.

Next, the extraction of hydrocodone (10 mg) from the test abuse deterrent formulations under boiling conditions was tested. Surprisingly, as shown in FIG. 11, formulations F2 and F5 when exposed to boiling water demonstrated a greatly reduced extraction of hydrocodone under boiling conditions when compared to the reference formulation or formulation F8. These formulations having oleic acid released approximately the same amount of hydrocodone as in the in vitro dissolution test that was performed at 37° C. Conversely, the Maisine™ 35-1 based formulation (F8) rapidly released hydrocodone when exposed to boiling water. These results are surprising and unexpected because sodium lauryl sulfate would be expected to solubilize the flowability enhancer and defeat the controlled release properties of the matrix.

Figure 12:
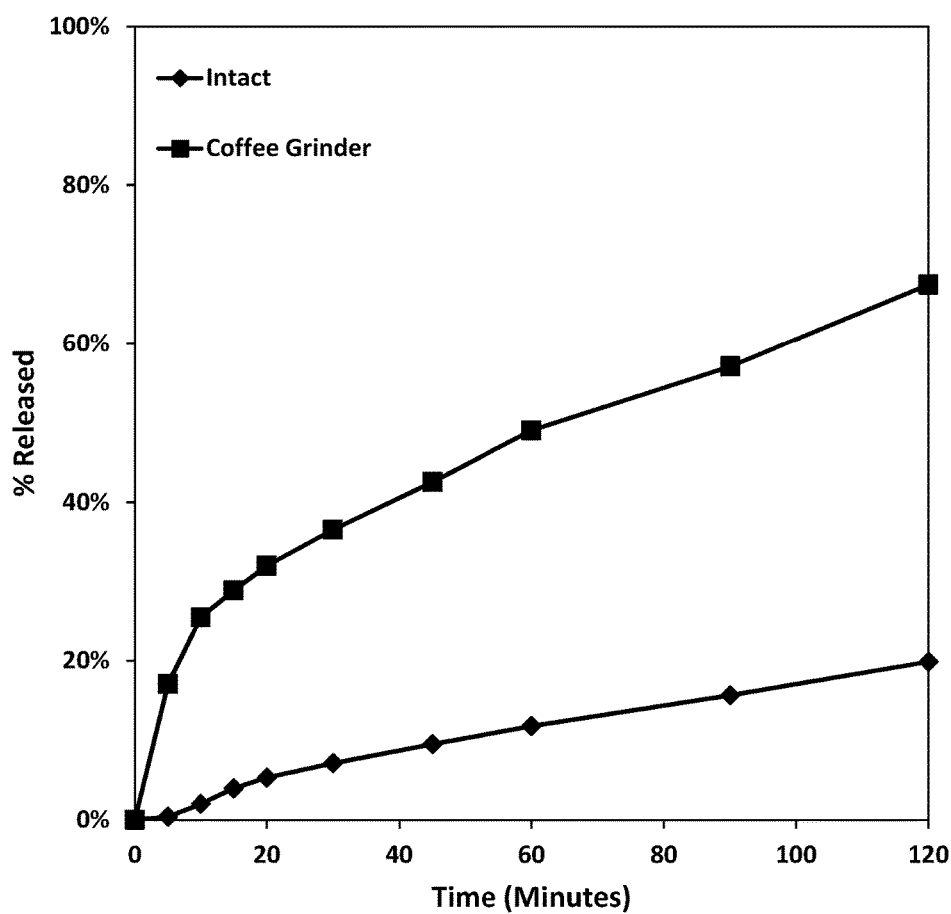
FIG. 12. Percent release of hydrocodone bitartrate from a test abuse deterrent pharmaceutical composition (F5) intact or manipulated by grinding with a coffee grinder under dissolution conditions in FASSGF using Apparatus III at 30 dips per minute.

The effects of physical manipulation on the dissolution of the test abuse deterrent formulation F5 of Table 4 containing hydrocodone were tested. The test formulation (F5) was manipulated by grinding with a coffee grinder. The intact or manipulated formulation was dissolved in an Apparatus III (reciprocating cylinder) at 30 dpm (most aggressive setting) in FASSGF media and evaluated for 2 hours (FIG. 12).

The percent release of hydrocodone in the above described experiments was determined by measuring the amount of hydrocodone released from the test and reference abuse deterrent compositions in FASSGF at pH 1.6 for one hour and in FASSIF at pH 6.5 for eleven hours according to USP specifications using Apparatus III at 30 dips per min (dpm). In these experiments, FASSGF comprised: 34.3 mM NaCl, 25.1 mM HCl, 80 µM sodium taurocholate, 20 µM lecithin, and optionally, 0.1 mg/mL pepsin. The FASSGF solution has a pH of 1.6 and an osmolality of 120±2.5 mOsm/kg. In these experiments, FASSIF comprised: 68.6 mM NaCl, 34.8 mM NaOH, 19.1 mM maleate, 3.0 mM sodium taurocholate, and 0.2 mM lecithin. The FASSIF solution has a pH of 6.5, an osmolality of 180±10 mOsm/kg, and a buffer capacity of 10 mM/ΔpH. Samples were removed from the apparatus at the indicated time points and the analyte was detected using high performance liquid chromatography (HPLC) with a UV detector.

Example 6

Additional exemplary abuse deterrent matrix compositions useful for producing abuse deterrent pharmaceutical compositions as described herein are shown in Tables 7-8. Composition components are set forth by weight percentage of the total weight of the matrix mass composition. Such compositions may be encapsulated in soft capsules, enteric soft capsules, hard capsules or enteric hard capsules.

TABLE 7

Exemplary Abuse Deterrent Non Burt Releasing Controlled Release Matrix Compositions

| Components | Weight Percentage (%) | | | | | |
|---|---|---|---|---|---|---|
| | EX 1 | EX 2 | EX 3 | EX 4 | EX 5 | EX 6 |
| Flowability Enhancer (e.g., Capmul ® MCM; Oleic Acid; and/or Maisine 35-1) | 59.65 | 65.65 | 56.65 | 64 | 61.65 | 54.65 |
| Release Modifier (e.g., Polyethylene oxide) | 30 | 30 | 35 | 23.15 | 30 | 40 |
| Viscosity Modifier (e.g., Ethocel ™ 20cP) | 1 | 1 | 4 | 1 | 1 | 1 |
| BHT | 0.1 | 0.1 | 0.1 | 0.1 | 0.1 | 0.1 |
| BHA | 0.25 | 0.25 | 0.25 | 0.25 | 0.25 | 0.25 |
| Surfactant (e.g., Sodium lauryl sulfate) | 7.5 | 2.5 | 2.5 | 10 | 2.5 | 2.5 |
| Active Pharmaceutical Ingredient(s); (e.g., hydrocodone, oxycodone, naloxone, methylnaltrexone, naltrexone) | 1.5 | 0.5 | 1.5 | 1.5 | 4.5 | 1.5 |
| TOTAL | 100 | 100 | 100 | 100 | 100 | 100 |

TABLE 8

Exemplary Abuse Deterrent Controlled Release Matrix Compositions

| Components | Weight Percentage (%) | | | | | |
|---|---|---|---|---|---|---|
| | EX 7 | EX 8 | EX 9 | EX 10 | EX 11 | EX 12 |
| Flowability Enhancer (e.g., Capmul ® MCM; Oleic Acid; and/or Maisine ™ 35-1) | 52.15 | 60.15 | 65.65 | 58.65 | 62.65 | 63.15 |
| Release Modifier (e.g., Polyethylene oxide) | 40 | 30 | 30 | 30 | 30 | 30 |
| Viscosity Modifier (e.g., Ethocel ™ 20cP) | 1 | 1 | 0 | 1 | 3 | 1 |
| BHT | 0.1 | 0.1 | 0.1 | 0.1 | 0.1 | 0.1 |
| BHA | 0.25 | 0.25 | 0.25 | 0.25 | 0.25 | 0.25 |
| Surfactant (e.g., Sodium lauryl sulfate) | 5 | 2.5 | 2.5 | 2.5 | 2.5 | 4 |
| Active Pharmaceutical Ingredient(s); (e.g., hydrocodone, oxycodone, naloxone, methylnaltrexone, naltrexone) | 1.5 | 6 | 1.5 | 7.5 | 1.5 | 1.5 |
| TOTAL | 100 | 100 | 100 | 100 | 100 | 100 |

What is claimed is:

1. An abuse deterrent oral pharmaceutical composition comprising a tamper resistant controlled release matrix comprising:
    (a) about 50% to about 65% by weight oleic acid or glyceryl monolinoleate;
    (b) about 25% to about 35% by weight polyethylene oxide;
    (c) 1% to about 5% by weight ethylcellulose having a viscosity of about 20 cP;
    (d) 1% to about 5% by weight sodium lauryl sulfate; and
    (e) 1.5% to about 10% by weight hydrocodone;
    wherein the matrix is resistant to tampering and prevents the burst release of the one or more active pharmaceutical ingredients and is encapsulated in a capsule shell.

2. The composition of claim 1, wherein the matrix further comprises one or more antioxidants.

3. The composition of claim 2, wherein the antioxidant comprises about 0.05% to about 0.5% by weight of the total matrix mass.

4. The composition of claim 1, wherein the polyethylene oxide comprises a polyethylene oxide having a molecular weight ($M_v$) of about 3,000,000, about 4,000,000, about 5,000,000; about 6,000,000, about 7,000,000, about 8,000,000, about 9,000,000, or about 10,000,000.

5. The composition of any one of claim 2, wherein the antioxidant comprises alpha tocopherol, beta tocopherol, gamma tocopherol, delta tocopherol, butylated hydroxytoluene (BHT), butylated hydroxyanisole (BHA), citric acid, ascorbic acid, carnosic acid, carnosol, rosmanol, epirosmanol, isorosmanol, methyl carnosate, rosmarinic acid, eugenol, eugenyl acetate, clove bud extract, methanolic extract, epigallocatechin gallate, epicatechin gallate, epigallocatechin, epicatechin, or a combination thereof.

6. The composition of claim 1, wherein the tamper resistant controlled release matrix forms a semisolid elastic composition after being heated at a temperature of about 50° C. to about 90° C. for a time period of about 0.1 hours to about 3 hours.

7. The composition of claim 1, wherein the capsule shell comprises a soft capsule shell.

8. A tamper resistant oral pharmaceutical composition comprising a tamper resistant controlled release matrix comprising:
    (a) about 50% to about 65% by weight of oleic acid;
    (b) about 25% to about 35% by weight polyethylene oxide having a molecular weight of from about 3,000,000 to about 7,000,000;
    (c) about 1% to about 5% by weight ethylcellulose having a viscosity of about 20 cP;
    (d) about 1% to about 5% by weight of sodium lauryl sulfate; and
    (e) about 1.5% to about 10% by weight of oxycodone or hydrocodone;
    wherein the matrix is resistant to tampering and has controlled release properties.

9. A method for treating, reducing the symptoms or onset of, or prophylaxis of pain stemming from diabetic neuropathy, chronic arthritis, osteoarthritis, rheumatoid arthritis, acute tendonitis, bursitis, headaches, migraines, chronic neuropathies, shingles, premenstrual symptoms, sports injuries, malignancy, radiculopathy, sciatica/sciatic pain, sarcoidosis, necrobiosis, lipoidica or granuloma annulare comprising administering to a subject in need thereof the pharmaceutical composition according to claim 1.

10. A method for reducing the burst release of one or more active ingredients from a pharmaceutical composition comprising providing the pharmaceutical composition according to claim 1.

11. An abuse deterrent oral pharmaceutical composition comprising a tamper resistant controlled release matrix, wherein the tamper resistant controlled release matrix comprises a means for preventing the crushing, grating, grinding, cutting, solvating, or dissolving of the tamper resistant controlled release matrix comprising:
    (a) about 50% to about 65% by weight of oleic acid;
    (b) about 25% to about 35% by weight polyethylene oxide having a molecular weight of from about 3,000,000 to about 7,000,000;
    (c) about 1% to about 5% by weight ethylcellulose having a viscosity of about 20 cP;
    (d) about 1% to about 5% by weight of sodium lauryl sulfate;
    (e) about 1.5% to about 10% by weight of hydrocodone; and
    (f) about 0.05% to about 0.5% by weight of one or more antioxidants.

12. The composition of claim 2, wherein the antioxidant comprises one or more of butylated hydroxytoluene (BHT), or butylated hydroxyanisole (BHA).

13. The composition of claim 8, further comprising:
    (f) about 0.25% by weight BHT; and
    (g) about 0.1% by weight BHA.

* * * * *